US012589112B2

(12) United States Patent
Yu et al.

(10) Patent No.: US 12,589,112 B2
(45) Date of Patent: Mar. 31, 2026

(54) ONCOLYTIC VIRUS COMPOSITIONS INCLUDING IL-15 COMPLEX AND METHODS FOR THE TREATMENT OF CANCER

(71) Applicant: CITY OF HOPE, Duarte, CA (US)

(72) Inventors: Jianhua Yu, Duarte, CA (US); Michael A. Caligiuri, Pasadena, CA (US)

(73) Assignee: CITY OF HOPE, Duarte, CA (US)

( * ) Notice: Subject to any disclaimer, the term of this patent is extended or adjusted under 35 U.S.C. 154(b) by 807 days.

(21) Appl. No.: 17/794,913

(22) PCT Filed: Jan. 22, 2021

(86) PCT No.: PCT/US2021/014683
§ 371 (c)(1),
(2) Date: Jul. 22, 2022

(87) PCT Pub. No.: WO2021/150936
PCT Pub. Date: Jul. 29, 2021

(65) Prior Publication Data

US 2023/0147832 A1 May 11, 2023

Related U.S. Application Data

(60) Provisional application No. 62/964,614, filed on Jan. 22, 2020.

(51) Int. Cl.

| | |
|---|---|
| ***C12N 15/869*** | (2006.01) |
| ***A61K 35/17*** | (2015.01) |
| ***A61P 35/00*** | (2006.01) |
| ***C07K 14/54*** | (2006.01) |
| ***C07K 14/715*** | (2006.01) |
| ***C12N 7/00*** | (2006.01) |
| ***C12N 15/62*** | (2006.01) |

(52) U.S. Cl.
CPC .............. *A61K 35/17* (2013.01); *A61P 35/00* (2018.01); *C07K 14/5443* (2013.01); *C07K 14/7155* (2013.01); *C12N 7/00* (2013.01); *C12N 15/62* (2013.01)

(58) Field of Classification Search
None
See application file for complete search history.

(56) References Cited

U.S. PATENT DOCUMENTS

| | | | | |
|---|---|---|---|---|
| 7,214,515 | B2 | 5/2007 | Chiocca et al. | |
| 9,862,932 | B2 | 1/2018 | Shah et al. | |
| 10,604,574 | B2 | 3/2020 | Evnin | |
| 2002/0187163 | A1 | 12/2002 | Johnson et al. | |
| 2015/0250837 | A1 | 9/2015 | Nolin et al. | |
| 2016/0244740 | A1 | 8/2016 | Kaur | |
| 2017/0210811 | A1 | 7/2017 | Wong et al. | |
| 2018/0117146 | A1* | 5/2018 | Yu | C07K 14/70521 |
| 2019/0048082 | A1 | 2/2019 | Evnin | |
| 2019/0169253 | A1* | 6/2019 | Jia | C07K 14/5443 |
| 2020/0236916 | A1* | 7/2020 | Shultz | A01K 67/0275 |
| 2023/0227549 | A1 | 7/2023 | Yu et al. | |

FOREIGN PATENT DOCUMENTS

| | | |
|---|---|---|
| WO | WO-2008/151182 A2 | 12/2008 |
| WO | WO-2008/151182 A3 | 12/2008 |
| WO | WO-2019/032866 A1 | 2/2019 |
| WO | WO-2019/129233 A1 | 7/2019 |
| WO | WO-2020/163721 A1 | 8/2020 |
| WO | WO-2021/159035 A1 | 8/2021 |

OTHER PUBLICATIONS

Chen et al. A combinational therapy of EGFR-CAR NK cells and oncolytic herpes simplex virus 1 for breast cancer brain metastases. Oncotarget. Apr. 1, 2016; 7(19): 27764-27777.*

Glorioso, J.C. et al. (2021, e-published Sep. 17, 2020). "Oncolytic HSV Vectors and Anti-Tumor Immunity," *Molecular Biology* 41:381-468.

International Search Report mailed on Apr. 27, 2021 for PCT Application No. PCT/US2021/016973, filed Feb. 6, 2021, 3 pages.

International Search Report mailed on Jun. 4, 2021 for PCT Application No. PCT/US2021/014683, filed Jan. 22, 2021, 5 pages.

Written Opinion mailed on Apr. 27, 2021 for PCT Application No. PCT/US2021/016973, filed Feb. 6, 2021, 7 pages.

Written Opinion mailed on Jun. 4, 2021 for PCT Application No. PCT/US2021/014683, filed Jan. 22, 2021, 5 pages.

Barclay, A.N. et al. (2014, e-published Nov. 6, 2013). "The interaction between signal regulatory protein alpha (SIRPα) and CD47: structure, function, and therapeutic target," *Annual Review Immunology* 32:25-50.

Extended European Search Report mailed on Feb. 27, 2024, for EP Patent Application No. 21750415.8, 11 pages.

Huang, Y. et al. (Mar. 2020, e-published Feb. 7, 2020). "A SIRPα-Fc fusion protein enhances the antitumor effect of oncolytic adenovirus against ovarian cancer," *Mol Oncol* 14(3):657-668.

Matlung, H.L. et al. (Mar. 4, 2017). "The CD47-SIRPα signaling axis as an innate immune checkpoint in cancer," *Immunological Reviews* 276(1):145-164.

Passaro, C. et al. (Oct. 2, 2018). "Arming an Oncolytic Herpes Simplex Virus Type 1 with a Single-chain Fragment Variable Antibody against PD-1 for Experimental Glioblastoma Therapy," *Clin Cancer Research* 25(1):290-299.

Sivanandam, V. et al. (Apr. 25, 2019). "Oncolytic Viruses and Immune Checkpoint Inhibition: The Best of Both Worlds," *Mol Ther Oncolytics* 13:93-106.

(Continued)

*Primary Examiner* — Nianxiang Zou
(74) *Attorney, Agent, or Firm* — Mintz, Levin, Cohn, Ferris, Glovsky and Popeo, P.C.

(57) ABSTRACT

Provided herein, inter alia, are compositions and methods including recombinant oncolytic viruses expressing human IL-15 and human IL-15Rα-sushi domain for the treatment of cancer and immune disorders. The recombinant oncolytic viruses may be used in combination with immune cells expressing chimeric antigen receptors (CAR) targeting EGFR and EGFR mutants.

20 Claims, 33 Drawing Sheets

Specification includes a Sequence Listing.

(56) References Cited

OTHER PUBLICATIONS

Xu, B. et al. (Oct. 8, 2021). "An oncolytic virus expressing a full-length antibody enhances antitumor innate immune response to glioblastoma," *Nature Communications* 12(1):5908.
Drean, et al. (Dec. 2016, e-published Oct. 31, 2016). "PARP inhibitor combination therapy," *Critical Reviews in Oncology/ Hematology* 108:73-85.
Lee, N. et al. (Nov. 2016). "Upregulation of CD47 in Regulatory T Cells in Atopic Dermatitis," *Yonsei Med J* 57(6):1435-1445.
Lai, P.-K. et al. (Jan.-Dec. 2021). "Differences in human IgG1 and IgG4 S228P monoclonal antibodies viscosity and self-interactions: Experimental assessment and computational predictions of domain interactions," *MAbs* 13(1):1991256.

* cited by examiner

SEQUENCE LISTING

<160> NUMBER OF SEQ ID NOS: 9

<210> SEQ ID NO 1
<211> LENGTH: 486
<212> TYPE: DNA
<213> ORGANISM: Artificial Sequence
<220> FEATURE:
<223> OTHER INFORMATION: Synthetic polynucleotide

<400> SEQUENCE: 1
atgagaattt cgaaaccaca tttgagaagt atttccatcc agtgctactt gtgtttactt 60
ctaaacagtc attttctaac tgaagctggc attcatgtct tcattttggg ctgtttcagt 120
gcagggcttc ctaaaacaga agccaactgg gtgaatgtaa taagtgattt gaaaaaaatt 180
gaagatctta ttcaatctat gcatattgat gctactttat atacggaaag tgatgttcac 240
cccagttgca aagtaacagc aatgaagtgc tttctcttgg agttacaagt tatttcactt 300
gagtccggag atgcaagtat tcatgataca gtagaaaatc tgatcatcct agcaaacaac 360
agtttgtctt ctaatgggaa tgtaacagaa tctggatgca aagaatgtga ggaactggag 420
gaaaaaaata ttaaagaatt tttgcagagt tttgtacata ttgtccaaat gttcatcaac 480
acttct 486

<210> SEQ ID NO 2
<211> LENGTH: 834
<212> TYPE: DNA
<213> ORGANISM: Artificial Sequence
<220> FEATURE:
<223> OTHER INFORMATION: Synthetic polynucleotide

<400> SEQUENCE: 2
atgaccgagg cttggagatg tctcgtcctg tccaatgtca ccgctagacc tgagaatctg 60
cacttgggag cttacagacc cggttctcag gcttcacttg agaccccaag aaagaaaaaa 120
acccaccagc caaagaggag gatggcagcc tggaagaacc taaggaagcg aggctcagag 180
tggggacacc ggaccgagtg cacactggag gtcccagagc acgacgagcg cggaggaccg 240
ggaggctccc gggcttgcgt gggcatcacg tgccctcccc ccatgtccgt ggaacacgca 300
gacatctggg tcaagagcta cagcttgtac tccagggagc ggtacatttg taactctggt 360
ttcaagcgta aagccggcac gtccagcctg acggagtgcg tgttgaacaa ggccacgaat 420
gtcgcccact ggacaacccc cagtctcaaa tgcattaagc ccgcagcttc atctcccagc 480
tcaaacaaca cagcggccac aacagcagct attgtcccgg gctcccagct gatgccttca 540
aaatcacctt ccacaggaac cacagagata agcagtcatg agtcctccca cggcaccccc 600
tctcagacaa cagccaagaa ctgggaactc acagcatccg cctcccacca gccgccaggt 660

-continued

```
gtgtatccac agggccacag cgacaccact gtggctatct ccacgtccac tgtcctgctg    720

tgtgggctga gcgctgtgtc tctcctggca tgctacctca agtcaagggc ctctgtctgc    780

tcctgccatc cccgcagtgc tggacataca tgctcagtgg gaagcgtctg ttga          834


<210> SEQ ID NO 3
<211> LENGTH: 867
<212> TYPE: DNA
<213> ORGANISM: Artificial Sequence
<220> FEATURE:
<223> OTHER INFORMATION: Synthetic polynucleotide

<400> SEQUENCE: 3

gctagcgcca ccatgtacag gatgcaactc ctgtcttgca ttgcactaag tcttgcactt     60

gtcacaaaca gtatgagaat ttcgaaacca catttgagaa gtatttccat ccagtgctac    120

ttgtgtttac ttctaaacag tcattttcta actgaagctg gcattcatgt cttcattttg    180

ggctgtttca gtgcagggct tcctaaaaca gaagccaact gggtgaatgt aataagtgat    240

ttgaaaaaaa ttgaagatct tattcaatct atgcatattg atgctacttt atatacggaa    300

agtgatgttc accccagttg caaagtaaca gcaatgaagt gctttctctt ggagttacaa    360

gttatttcac ttgagtccgg agatgcaagt attcatgata cagtagaaaa tctgatcatc    420

ctagcaaaca acagtttgtc ttctaatggg aatgtaacag aatctggatg caaagaatgt    480

gaggaactgg aggaaaaaaa tattaaagaa tttttgcaga gttttgtaca tattgtccaa    540

atgttcatca acacttctag cggcggtggc agcggcggtg gcggtagcgg cggtggcggt    600

agcggcggtg gcggtagcgg cggtggcagc ctgcagatca cctgccccc ccccatgagc    660

gtggagcacg ccgacatctg ggtgaagagc tacagcctgt acagcagaga gagatacatc    720

tgcaacagcg gcttcaagag aaaggccggc accagcagcc tgaccgagtg cgtgctgaac    780

aaggccacca acgtggccca ctggaccacc cccagcctga agtgcatcag atacccatac    840

gatgttccag attacgcttg agaattc                                        867


<210> SEQ ID NO 4
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 4

atgtacagga tgcaactcct gtcttgcatt gcactaagtc ttgcacttgt cacaaacagt     60


<210> SEQ ID NO 5
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 5

tacccatacg atgttccaga ttacgct                                         27


<210> SEQ ID NO 6
<211> LENGTH: 144
<212> TYPE: DNA
<213> ORGANISM: Artificial Sequence
<220> FEATURE:
<223> OTHER INFORMATION: Synthetic polynucleotide

<400> SEQUENCE: 6
```

-continued

```
ttcgcacttc gtcccaatat atatatatta ttagggcgaa gtgcgagcac tggcgccgtg     60

cccgactccg cgccggcccc gggggcgggc ccgggcggcg gggggcgggt ctctccggcg    120

cacataaagg cccggcgcga ccga                                           144


<210> SEQ ID NO 7
<211> LENGTH: 345
<212> TYPE: DNA
<213> ORGANISM: Artificial Sequence
<220> FEATURE:
<223> OTHER INFORMATION: Synthetic polynucleotide

<400> SEQUENCE: 7

gacattctaa tgacccaatc tccactctcc ctgcctgtca gtcttggaga tcaagcctcc     60

atctcttgca gatctagtca gaacattgta cataataatg gaatcaccta tttagaatgg    120

tacctgcaaa ggccaggcca gtctccaaag ctcctgatct acaaagtttc cgaccgattt    180

tctggggtcc cagacaggtt cagtggcagt ggatcaggga cagatttcac actcaagatc    240

agcagagtag aggctgagga tctgggaatt tattactgct ttcaaggttc acatattcct    300

cccacgttcg gagggggac caagctggaa atcaaacgtg cggcc                    345


<210> SEQ ID NO 8
<211> LENGTH: 354
<212> TYPE: DNA
<213> ORGANISM: Artificial Sequence
<220> FEATURE:
<223> OTHER INFORMATION: Synthetic polynucleotide

<400> SEQUENCE: 8

caggtccagc tgcagcagtc tgggtctgag atggcgaggc ctggagcttc agtgaagctg     60

ccctgcaagg cttctggcga cacattcacc agttactgga tgcactgggt gaagcagagg    120

catggacatg gccctgagtg gatcggaaat atttatccag gtagtggtgg tactaactac    180

gctgagaagt tcaagaacaa ggtcactctg actgtagaca ggtcctcccg cacagtctac    240

atgcacctca gcaggctgac atctgaggac tctgcggtct attattgtac aagatcgggg    300

ggtccctact tctttgacta ctggggccaa ggcaccactc tcacagtctc ctcc          354


<210> SEQ ID NO 9
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 9

ggcgggggcg gtagcggcgg tggcgggtcg ggcggtggcg gatcc                     45
```

ONCOLYTIC VIRUS COMPOSITIONS INCLUDING IL-15 COMPLEX AND METHODS FOR THE TREATMENT OF CANCER

CROSS-REFERENCE TO RELATED APPLICATIONS

This application is a National Stage Entry of PCT Application No. PCT/US2021/014683, filed Jan. 22, 2021, which claims priority to U.S. Provisional Application No. 62/964,614, filed Jan. 22, 2020, which are hereby incorporated by reference in their entirety and for all purposes.

STATEMENT AS TO RIGHTS TO INVENTIONS MADE UNDER FEDERALLY SPONSORED RESEARCH AND DEVELOPMENT

This invention was made with government support under NS106170 and CA163205 awarded by the National Institutes of Health. The government has certain rights in the invention.

REFERENCE TO A SEQUENCE LISTING, A TABLE OR A COMPUTER PROGRAM LISTING APPENDIX SUBMITTED AS AN ASCII TEXT FILE

The Sequence Listing written in file 048440-747001WO_ST25.TXT, created on Jan. 21, 2021, 5,725 bytes, machine format IBM-PC, MS Windows operating system, is hereby incorporated by reference.

BACKGROUND

Oncolytic viral (OV) therapy has been recognized as a promising approach for cancer treatment. It differs from traditional gene therapy where a viral vector serves for delivery of a specific gene. OV therapy utilizes the virus itself as an immune stimulatory agent that can also selectively replicate in tumor cells resulting in their lysis without harming normal tissues. The concept of OV therapy has existed for decades. In 1991, Martuza et al. demonstrated that OV therapy was effective at treating preclinical models of brain tumors with a genetically engineered herpes simplex virus type I (HSV-1) containing a mutation in the thymidine kinase (TK) gene. This encouraged researchers to further modify the viral genome to design an oncolytic HSV-1 (oHSV). Over the past two decades, it has been established that oHSV can boost systemic immunity and therefore the anti-tumor immune response. (See, for example Refs. 1-2).

Interleukin (IL)-15 is a pleiotropic cytokine playing multiple roles in improving immune responses to tumor cells. IL-15 or its complex with the interleukin-15 receptor alpha sushi domain (IL-15/IL-15Rα) is being tested in the clinic with good responses in patients. Interleukin (IL)-15 is a pleiotropic cytokine and plays a key role in the development, homeostasis, activation, and survival of T, natural killer (NK), and NK-T cells (3). IL-15 receptor alpha (IL-15Rα) is one of three receptors required to mediate IL-15 signaling (4). IL-15 cytokine agonists that include IL-15 and complete or partial IL-15Rα to improve in vivo anti-tumor activities (5, 6). Both IL-15 and the IL-15/IL-15Rα complex are actively being tested in phase I and II clinical trials with evidence of immune modulation in patients (7-9).

Another promising approach to control tumor progression is engineering immune cells with a chimeric antigen receptor (CAR), which is an artificially modified fusion protein including an extracellular antigen recognition domain fused to an intracellular signaling domain and designed to enhance the specificity of T cells, NK cells or other immune cells (15). CAR-modified T cells are currently being tested in patients with solid tumors including glioblastoma (GBM) (16, 17), and CAR-modified NK cells have also shown early success in lymphoid malignances (18). However, CAR T or CAR NK cells in combination with other therapies including OV have not yet been widely explored.

Moreover, engineering viruses to infect tumors and express transgenes, including immunostimulatory molecules such as cytokines, can improve the efficacy of oncolytic virotherapy (10-14). However, there remains the need for an effective combination of IL-15 or IL-15/IL-15Rα via a single agent delivered into the tumor microenvironment for the treatment of cancer. Provided herein, inter alia, are solutions to these and other problems in the art.

BRIEF SUMMARY OF THE INVENTION

In an aspect, provided herein is a recombinant oncolytic herpes simplex virus including an expression cassette encoding a human IL15 domain and a human IL-15Rα sushi domain.

In an aspect, provided herein is a pharmaceutical composition including a recombinant oncolytic herpes simplex virus that includes an expression cassette encoding a human IL15 domain and a human IL-15Rα sushi domain, and a pharmaceutically acceptable carrier.

In an aspect, provided herein is a combination therapy including a pharmaceutical composition that includes a recombinant oncolytic herpes simplex virus including an expression cassette encoding a human IL15 domain and a human IL-15Rα sushi domain and a checkpoint inhibitor.

In an aspect, provided herein is a method for killing tumor cells in a subject including administering to a subject an effective amount of a recombinant oncolytic herpes simplex virus including an expression cassette encoding a human IL15 domain and a human IL-15Rα sushi domain.

In an aspect, provided herein is a method of treating a patient having cancer including administering to the patient an effective amount of a pharmaceutical composition including a recombinant oncolytic herpes simplex virus including an expression cassette encoding a human IL15 domain and a human IL-15Rα sushi domain, and a pharmaceutically acceptable carrier. In an aspect, provided herein is a method of treating a patient having cancer including administering to the patient an effective amount of a recombinant oncolytic herpes simplex virus including an expression cassette encoding a human IL15 domain and a human IL-15Rα sushi domain.

In an aspect, provided herein is a method of treating a subject with an overactive immune system, including administering to the patient an effective amount of a pharmaceutical composition including a recombinant oncolytic herpes simplex virus including an expression cassette encoding a human IL15 domain and a human IL-15Rα sushi domain, and a pharmaceutically acceptable carrier. In an aspect, provided herein is a method of treating a subject with an overactive immune system, including administering to the patient an effective amount of a recombinant oncolytic herpes simplex virus including an expression cassette encoding a human IL15 domain and a human IL-15Rα sushi domain.

In an aspect, provided herein is a method for increasing cytotoxicity of natural killer (NK) cells and/or CD8 T cells in a subject, including administering to the patient an effective amount of a pharmaceutical composition including a recombinant oncolytic herpes simplex virus that includes an expression cassette encoding a human IL15 domain and a human IL-15Rα sushi domain, and a pharmaceutically acceptable carrier. In an aspect, provided herein is a method for increasing cytotoxicity of natural killer (NK) cells and/or CD8 T cells in a subject, including administering to the patient an effective amount of a recombinant oncolytic herpes simplex virus including an expression cassette encoding a human IL15 domain and a human IL-15Rα sushi domain.

In an aspect, provided herein is a method for increasing survival and/or proliferation of immune cells in a subject, including administering to the subject an effective amount of a pharmaceutical composition including a recombinant oncolytic herpes simplex virus that includes an expression cassette encoding a human IL15 domain and a human IL-15Rα sushi domain, and a pharmaceutically acceptable carrier. In an aspect, provided herein is a method for increasing survival and/or proliferation of immune cells in a subject, including administering to the patient recombinant oncolytic virus including an expression cassette encoding a human IL15 domain and a human IL-15Rα sushi domain.

In an aspect provided herein is a pharmaceutical composition including a first pharmaceutical dosage unit of the recombinant oncolytic virus provided herein including embodiments thereof, a second pharmaceutical dosage unit including Epidermal Growth Factor Receptor-Chimeric Antigen Receptor Natural Killer (EGFR-CAR NK) cells, and a pharmaceutically acceptable carrier.

In an aspect provided herein is combination therapy including a pharmaceutical composition provided herein including embodiments thereof and a checkpoint inhibitor.

In an aspect provided herein is a method for killing tumor cells in a subject comprising: administering to a subject an effective amount of a pharmaceutical composition provided herein including embodiments thereof.

In an aspect provided herein is a method method of treating a patient having cancer comprising administering to the patient an effective amount of a pharmaceutical composition provided herein including embodiments thereof.

BRIEF DESCRIPTION OF THE DRAWINGS

FIG. 1A shows schematic maps of oncolytic viruses used in this study. First (top): genetic map of wild type HSV-1. Second: genetic map of the parental oHSV control (OV-Q1) with deletion of γ34.5, dysfunction of ICP6, and insertion of the GFP gene. Third: genetic map of the new oHSV (OV-IL15C) showing the insertion of the human IL15 and IL-15Rα Sushi domain driven by the viral pIE4/5 promoter. FIG. 1B shows plaque forming assays. Vero cells were seeded in a 96-well plate and infected by parental oHSV control OV-Q1 or OV-IL15C at different dilutions of viral solutions. From Day 1 to Day 4, GFP-positive plaques were counted with a Zeiss fluorescence microscope. FIG. 1C shows immunoblotting performed to test the expression of the human IL-15/IL-15Rα complex at the protein level. 293T were uninfected, infected by parental oHSV control OV-Q1, or OV-IL15C. Two days later, supernatants were collected and used for the detection of the HA-tagged IL-15/IL-15Rα complex by immunoblotting with an expected size of 32 kDa. FIGS. 1D-1E show ELISA for the human IL-15/IL-15R complex. GBM cell lines (U251 and LN229) and 293T cells were uninfected, infected by parental oHSV control OV-Q1 or OV-IL15C. From Day 1 to Day 4, supernatants from different groups were collected for qualification of the IL-15/IL-15Rα complex. The assay was performed in three biological replicates (n=3).

FIGS. 2A-2B show $^{51}Cr$ cytotoxicity release assays. Primary human NK cells were pre-incubated with concentrated supernatants from uninfected, Q1-infected, OV-IL15C-infected U251 cells for 18 hours. K562 and GBM30 cells were used as target cells and labeled with $^{51}Cr$ for 1.5 hours, and then were co-cultured with the above pre-treated NK cells at different effector:target ratios (40:1, 20:1, 10:1, and 5:1) at 37° C. for 4 hours for cytotoxicity assays. The assays were performed in at least three technical replicates with human NK cells from four different donors. FIGS. 2C-2D show flow cytometry-based cytotoxicity assays. Enriched supernatants from uninfected, Q1-infected, OV-IL15C-infected U251 cells were co-cultured with primary human NK cells for 18 hours for NK cells and 48 hours for CD8 T cells (FIG. 2C). The pre-incubated NK cells were used as effector cells in 4-hour cytotoxicity assays in which APC-labeled K562 were used as target cells. The pre-incubated CD8 T cells were co-cultured with the target K562 cells, which had been labeled with an APC-dye, at various effector:target ratios (50:1, 25:1, 12.5:1, and 6.25:1) at 37° C. for 12 hr (FIG. 2D). The dead cells were stained by SYTOX™ Blue Dead Cell Stain and cell death percentages were shown on they axis (c, d). The assays were performed in at least three technical replicates with human NK cells from four different donors and CD8T cells from five different donors.

FIG. 3A is data showing primary human NK cells were cultured in supernatants from uninfected or OV-Q1 and OV-IL15C infected U251 GBM cells in absence of IL-2. On Day 0, $1\times10^6$ per well of NK cells were seeded in a round bottom 96-well plate. From Day 1 to Day 4, live NK cells in each group were counted using Trypan Blue exclusion assays. The experiment was performed in at least three technical replicates with human NK cells from four different donors. FIG. 3B is data showing flow based apoptosis assays.

FIG. 4A shows schematic maps of oncolytic viruses used in this study. First: genetic map of wild-type HSV-1 (wt HSV-1). Second: genetic map of the parental oHSV control (OV-Q1) with deletion of γ34.5, dysfunction of ICP6, and insertion of the GFP gene. Third: genetic map of the new oHSV (OV-IL15C) showing the insertion of the human IL-15 and IL-15Rα sushi domain driven by the viral pIE4/5 promoter (SEQ ID NO:6). FIG. 4B is an image of a gel from an immunoblotting experiment to test the expression of the human IL-15/IL-15Rα complex at the protein level. 293T cells were infected by OV-Q1 or OV-IL15C at a MOI of 2. Two days later, cell lysis was collected and used for detection of the HA-tagged IL-15/IL-15Rα complex by immunoblotting with an expected size of 32 kDa. β-actin was used as endogenous control. The experiment was repeated three times with similar results. FIG. 4C is ELISA data for the human IL-15/IL-15Rα complex quantification. GBM cell lines (human cell lines U251 and LN229, murine GBM cell line CT2A) and 293T cells were grouped for uninfected, infected by OV-Q1 or OV-IL15C with 0.05 MOI. Supernatants from different groups were collected for quantification of the IL-15/IL-15Rα complex. The experiment was repeated three times. P values correct for Ordinary one-way ANOVA using Holm-Sidak multiple comparisons test, **, P<0.0001. Values are presented as mean±SD. FIG. 4**D is data from a viral production capacity test. Human GBM cell lines U251 or LN229 were seeded in a 96-well plate and infected by OV-Q1 or OV-IL15C at different MOIs (MOI=0.005 unsaturated or 5 saturated). From 24 to 96 h post infection, GFP-positive plaques were counted with a Zeiss fluorescence microscope. The experiment was repeated three times. Values are presented as mean±SD.

FIG. 5A are graphs showing data from $^{51}Cr$-release assay. Primary human NK cells were pre-incubated with concentrated (1:10) supernatants from OV-Q1- or OV-IL15C-infected U251 cells for 18 h. GBM30 cells were used as target cells and labeled with $^{51}Cr$ for 1.5 h, and then were co-cultured with the above pre-treated NK cells at different E/T ratios (40:1, 20:1, 10:1, and 5:1) at 37° C. for 4 h. The results show the average of four different donors. P values correct for multiple comparisons using the Holm-Sidak method, *, P<0.05, , P<0.01, *, P<0.001. Values are presented as mean±SEM. FIG. 5B shows data from flow cytometry-based cytotoxicity assay. Primary human $CD8^+$ T cells were incubated with concentrated (1:10) supernatants for 48 h, followed by co-culturing with the APC-labelled target GBM30 cells at various E/T ratios (50:1, 25:1, 12.5:1, and 6.25:1) at 37° C. for 12 h. The dead cells were stained by SYTOX™ Blue Dead Cell. The results show the average of five different donors. P values correct for multiple comparisons using the Holm-Sidak method, *, P<0.05, , P<0.01, , P<0.0001. Values are presented as mean±SEM. FIGS. 5C and 5E show primary human NK or $CD8^+$ T cells cultured in supernatants from OV-Q1- or OV-IL15C-infected U251 GBM cells in the absence of hrIL-2, respectively. On day 0, $1\times10^6$ NK or $CD8^+$ T cells per well were seeded in a round bottom 96-well plate. From day 1 to day 4, live cells in each group were counted using Trypan Blue exclusion assays. The experiment was repeated with human NK or $CD8^+$ T cells from four different donors. P values correct for multiple comparisons using the Holm-Sidak method, , P<0.01, *, P<0.001, , P<0.0001. Values are presented as mean±SD. Proteins from NK or $CD8^+$ T cells cultured in supernatants as above were collected after 18 h or 48 h, respectively. 20 μg total proteins for each sample were loaded into the SDS gel. Immunoblotting assays for FIGS. 5D and 5**F were repeated with four different donors showing similar data.

FIG. 6A shows an experimental timeline for in vivo study. The xenograft GBM mouse model was established by intracranial injection of $1\times10^5$ GBM30-luci cells into NSG mice on day 0. On day 5, mice were intratumorally injected with $2\times10^5$ pfu of OV-Q1, OV-IL15C or saline as well as $1\times10^6$ activated $CD8^+$ T cells simultaneously. On day 12, a second time of intratumorally injected with $2\times10^5$ pfu of OV-Q1, OV-IL15C or saline as well as $1\times10^6$ activated $CD8^+$ T cells was performed again. FIG. 6B shows data from day 8, Luciferase imaging to check brain tumors growth. FIG. 6C shows quantification of luciferase expression in FIG. 6B. P values were generated by one-way ANOVA with Holm's multiple comparisons test. , P<0.01, , P<0.0001. Values are presented as mean±SD. FIG. 6D shows data from day 15, Luciferase imaging to check brain tumors growth. FIG. 6E shows quantification of luciferase expression in FIG. 6**D. P values were generated by one-way ANOVA with Holm's multiple comparisons test. *, P<0.05. *, P<0.001, , P<0.0001. Values are presented as mean±SD. FIG. 6F illustrates survival of GBM30-luci bearing mice treated with OV-Q1, OV-IL15C or saline with activated $CD8^+$ T cells. Log-rank test was used to compare survival curves. , P<0.01.

FIG. 7A illustrates efficiency of EGFR-CAR expression after 48 h retroviral transduction. Anti-mouse Fab' antibody was used to stain human anti-EGFR scFv on NK cells. FIG. 7B left panel shows unsorted EGFR-CAR NK cells cytotoxicity function against target EGFR-expressing GBM cell line LN229; right panel shows an eosinophilic leukemia cell line EOL-1 was used as a negative control. P values correct for multiple comparisons using the Holm-Sidak method, *, P<0.05, , P<0.01. Values are presented as mean±SEM. Experiment was repeated three times with NK cells isolated from different donors with similar results. FIG. 7**C shows degranulation and secretion of IFN-γ and TNF-α from untraduced (UT), unsorted EV-transduced or EGFR-CAR transduced NK cells co-cultured with GBM cell lines LN229 (EGFR positive) and U87vIII (EGFRvIII positive). Also, EOL-1 was performed as negative control. Experiment was repeated seven times with NK cells isolated from different donors with similar results. P values were calculated by one-way ANOVA with Holm's multiple comparisons test. *, P<0.05, , P<0.01, *, P<0.001, **, P<0.0001. Values are presented as mean±SD. FIG. 7**D is the experimental timeline. On day 0, a xenograft GBM mouse model was established by intracranial injection of $1\times10^5$ U87vIII-luci cells into NSG mice. On days 3, mice were intratumorally injected with $1\times10^6$ frozen EV-transduced NK cells, $1\times10^6$ frozen EGFR-CAR NK cells, or saline alone. All transduced cells were unsorted. n=5 animals for each group.

FIG. 7E is data showed luciferase imaging of U87vIII-luci brain tumors on day 8. FIG. 7F shows quantification of luciferase expression in FIG. 7E. P values were generated by one-way ANOVA with Holm's multiple comparisons test. *, P<0.05. Values are presented as mean±SD. FIG. 7G shows survival of U87vIII-luci bearing mice treated with EV-transduced NK cells, EGFR-CAR NK cells, or saline alone. Log-rank test was used to compare animal survival curves. **, P<0.01.

FIG. 8A is the experimental timeline for in vivo study. FIG. 8B shows representative images of luciferase imaging. On day 0, a xenograft GBM mouse model was established by intracranially injection of $1\times10^5$ GBM30-luci cells into NSG mice. On day 5, mice were intratumorally injected with $2\times10^5$ pfu of OV-Q1 plus $1\times10^6$ frozen EGFR-CAR NK cells, $2\times10^5$ pfu of OV-IL15C plus $1\times10^6$ frozen EGFR-CAR NK cells, or saline alone. All transduced cells were unsorted. On day 12, a second intracranial injection was performed same as day 5. n=5 animals for each group. Data showed luciferase imaging of GBM30-luci brain tumors on day 15. FIG. 8C shows quantification of luciferase expression in FIG. 8B. P values were generated by one-way ANOVA with Holm's multiple comparisons test. *, P<0.05, **, P<0.0001. Values are presented as mean±SD. FIG. 8D illustrates survival of GBM30-luci bearing mice treated with OV-Q1 or OV-IL15C combined with unsorted frozen EGFR-CAR NK cells or saline. Log-rank test was used to compare animal survival curves. , P<0.01. FIG. 8E shows representative images of luciferase imaging. The xenograft GBM mouse model was established by intracranially injection of $1\times10^5$ GBM30-luci cells into NSG mice on day 0. On days 5, mice were intratumorally injected with $1\times10^6$ EGFR-CAR NK cells alone, $2\times10^5$ pfu OV-IL15C alone, $2\times10^5$ pfu OV-IL15C combined with $1\times10^6$ EGFR-CAR NK cells or saline as control. n=6 animals for each group. On day 12, a second intratumorally injection was performed same as day 5. Luciferase imaging of GBM30-luci brain tumors on day 15. FIG. 8F shows quantification of luciferase expression in FIG. 8E. P values were generated by one-way ANOVA with Holm's multiple comparisons test. *, P<0.05, *, P<0.001, , P<0.0001. Values are presented as mean±SD. FIG. 8G shows survival of GBM30-luci bearing mice. Log-rank test was used to compare animal survival curves. , P<0.01, ***, P<0.001.

FIGS. 9A and 9B are bar graphs representative of NK and T cells infiltration in brain and spleen, respectively. An immunocompetent GBM mouse model was established by intracranially injecting $1\times10^5$ CT2A cells into C57BL/6 mice. n=6 animals for each group. Five days later, mice were intratumorally injected with $2\times10^5$ pfu of OV-Q1, OV-IL15C or saline as control. P values correct for multiple comparisons using the Holm-Sidak method, *, P<0.05, , P<0.01, *, P<0.001, **, P<0.0001. Values are presented as mean±SD. FIG. 9C upper panel shows the in vivo experiment schedule; bottom panel shows survival of CT2A bearing mice treated with $2\times10^5$ pfu of OV-Q1, OV-IL15C or saline as control. Log-rank test was used to compare animal survival curves. n=8 animals for each group. , P<0.01, *, P<0.001. FIG. 9D upper panel shows in vivo experiment schedule; bottom panel shows survival of CT2A-hEGFR bearing mice treated with $2\times10^5$ pfu of OV-IL15C alone, $1\times10^6$ EGFR-CAR NK cells alone, or combination of the two treatments as well as saline as control. Log-rank test was used to compare animal survival curves. n=6 animals for each group. , P<0.01, ***, P<0.001.

FIG. 10A show results from the cytotoxicity assay. Human primary NK and $CD8^+$ T cells were pre-treated with the enriched supernatants as FIG. 5. $^{51}Cr$-release assay to test the cytotoxicity ability of NK cells to target K562 cells. K562 is a classic MHC class 1 negative cell line sensitive to NK cell killing. The cytotoxicity assay was performed for 4 h at 37° C. at different E/T ratios (20:1, 10:1, and 5:1) and repeated with NK cells from four different donors. Flow cytometry-based cytotoxicity assay to test the cytotoxicity ability of $CD8^+$ T cells target to K562 cells. The cytotoxicity assay was performed for 12 h at 37° C. at different E/T ratios (50:1, 25:1, 12.5:1, and 6.25:1) and repeated with $CD8^+$ T from five different donors. P values correct for multiple comparisons using the Holm-Sidak method, *, P<0.05, , P<0.01, **, P<0.0001. Values are presented as mean±SEM. FIG. 10B illustrates the stimulation of $CD8^+$ T cells. Human primary $CD8^+$ T cells were labeled with an APC-dye on day 0 and cultured with enriched supernatants as above in presence of hrIL-2 and human anti-CD3CD28 beads. On day 2 and day 3, flow cytometry was used to test the stimulation of $CD8^+$ T cells. The experiment was repeated with three different donors with similar results.

FIG. 11A is a schematic of experimental timeline. GBM30-luci cells were intracranially implanted on day 0 and allowed to grow for five days. On day 5, a first time intratumoral injection with oHSV combined with $1\times10^6$ primary NK cells was performed. On day 12, a second time intratumoral injection was performed. n=5 animals for each group. FIG. 11B are representative images of luciferase imaging. Tumor size was determined by imaging to quantify the luciferase expression on day 15. FIG. 11C show quantification of luciferase expression in FIG. 11B. P values were generated by one-way ANOVA with Holm's multiple comparisons test. , P<0.01. Values are presented as mean±SD. FIG. 11D illustrate survival of GBM30-luci bearing mice treated with OV-Q1, OV-IL15C or saline simultaneously with primary NK cells. Log-rank test was used to compare animal survival curves. , P<0.01.

FIG. 13A are representative images from plaque forming assays. The assays were performed with four different types of human primary cells including oral fibroblasts (HOrF), pulmonary microvascular endothelial cells (HPMEC), and hepatic sinusoidal endothelial cells (HHSEC). The experiment was repeated three times with similar results. FIG. 13B show survival curves of BALB/c mice treated with wild-type HSV-1 (F strain) and OV-IL15C at the dose of $1\times10^6$ pfu via intracranial injection. n=5 animals for each group. Mice treated with wild-type HSV-1 survived for less than 12 d, while all mice treated with OV-Q1 or OV-IL15C survived until the end of the 4-week study. Log-rank test was used to compare animal survival curves. **, P<0.01.

DETAILED DESCRIPTION

Figure 1A:
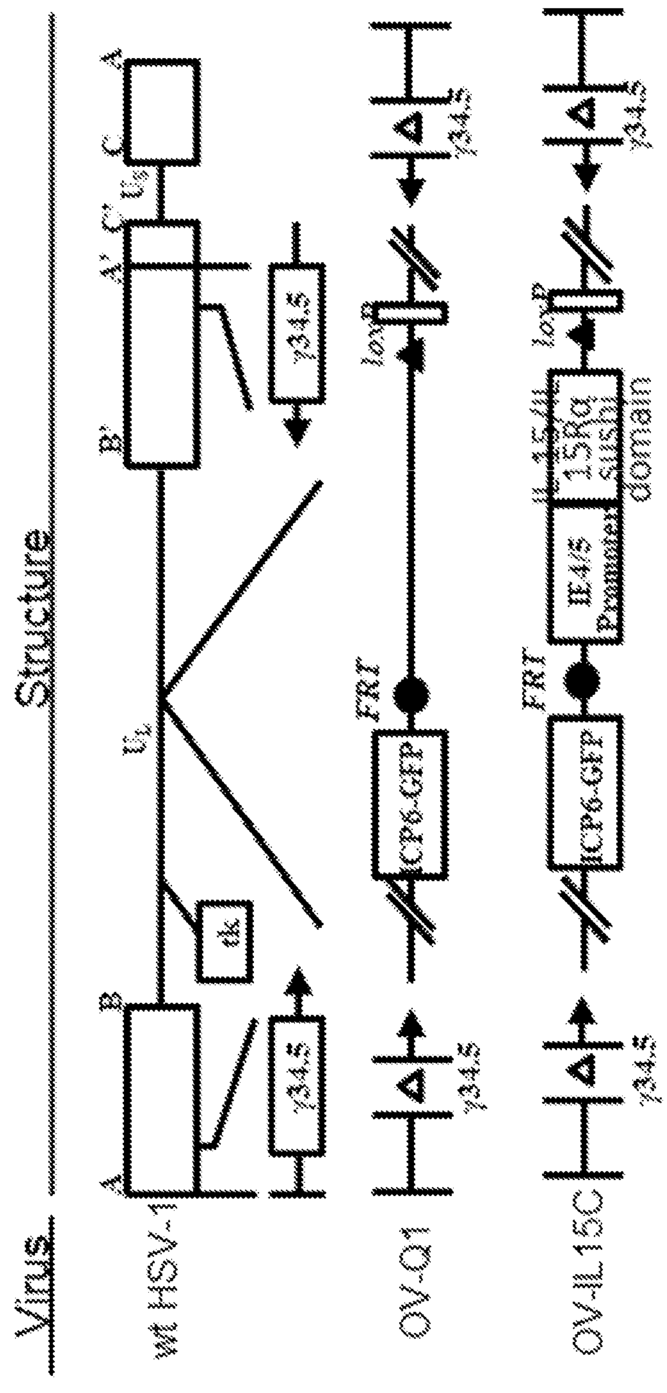
FIGS. 1A-1E demonstrates the generation of OV-IL15C and detection and quantification of the IL-15/IL-15Rα complex produced by OV-IL15C infection of GBM cells.

Provided herein are, inter alia, recombinant oncolytic herpes simplex viruses (HSV) expressing human IL-15 and human IL-15Rα-sushi domain and methods for the treatment of cancer and immune disorders. The recombinant oncolytic HSV can be used in combination with immune cells expressing chimeric antigen receptors (CAR) targeting EGFR and EGFR mutants for the treatment of cancer for synergistic anti-tumor effect.

I. Definitions

Before the present invention is further described, it is to be understood that this invention is not strictly limited to particular embodiments described, and as such may of course vary. It is also to be understood that the terminology used herein is for the purpose of describing particular embodiments only, and is not intended to be limiting, since the scope of the present invention will be limited only by the claims.

It must be noted that as used herein and in the appended claims, the singular forms "a," "an," and "the" include plural referents unless the context clearly dictates otherwise. It should further be understood that as used herein, the term "a" entity or "an" entity refers to one or more of that entity. For example, a nucleic acid molecule refers to one or more nucleic acid molecules. As such, the terms "a", "an", "one or more" and "at least one" can be used interchangeably. Similarly the terms "comprising", "including" and "having" can be used interchangeably.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +1-10% of the specified value. In embodiments, about means the specified value.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

For example, a vector may include a nucleic acid that encodes a protein (i.e. IL15, IL-15R Rα sushi domain). The vector may include an expression cassette. The term "expression cassette" is used according to its commonly known meaning in the art and refers to a polynucleotide encoding a gene. For example an expression cassette may include a nucleic acid encoding human IL15 and human IL-15Rα sushi domain. An expression cassette may include one or more regulatory sequences (i.e. a promoter) that increases gene expression in a cell.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism.

The term "complement," as used herein, refers to a nucleotide (e.g., RNA or DNA) or a sequence of nucleotides capable of base pairing with a complementary nucleotide or sequence of nucleotides. As described herein and commonly known in the art the complementary (matching) nucleotide of adenosine is thymidine and the complementary (matching) nucleotide of guanosine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and a non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

As described herein the complementarity of sequences may be partial, in which only some of the nucleic acids match according to base pairing, or complete, where all the nucleic acids match according to base pairing. Thus, two sequences that are complementary to each other, may have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region).

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and 0-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may In embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

The term "amino acid side chain" refers to the functional substituent contained on amino acids. For example, an amino acid side chain may be the side chain of a naturally occurring amino acid. Naturally occurring amino acids are those encoded by the genetic code (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine), as well as those amino acids that are later modified, e.g., hydroxyproline, γ-carboxyglutamate, and O-phosphoserine. In embodiments, the amino acid side chain may be a non-natural amino acid side chain. In embodiments, the amino acid side chain is H,

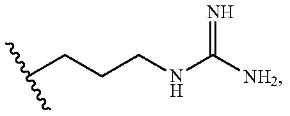 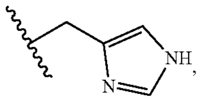

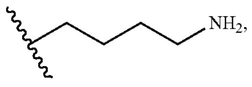 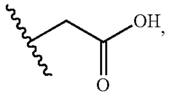

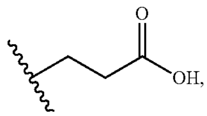 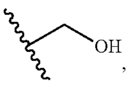 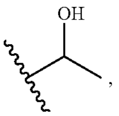

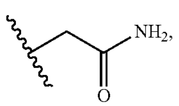 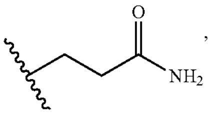 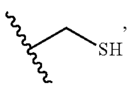

-continued

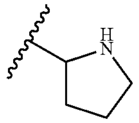 , 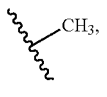 , 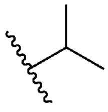 , 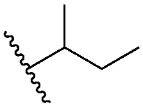 ,

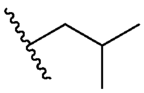 , 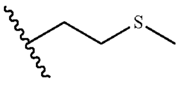 , 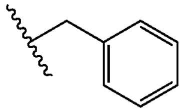 ,

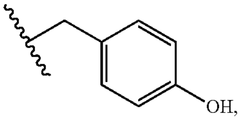 or 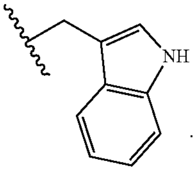 .

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

The terms "virus" or "virus particle" are used according to its plain ordinary meaning within virology and refers to a virion including the viral genome (e.g. DNA, RNA, single strand, double strand), viral capsid and associated proteins, and in the case of enveloped viruses (e.g. herpesvirus), an envelope including lipids and optionally components of host cell membranes, and/or viral proteins.

The term "plaque forming units" is used according to its plain ordinary meaning in Virology and refers to a unit of measurement based on the number of plaques per unit volume of a sample. In some embodiments the units are based on the number of plaques that could form when infecting a monolayer of susceptible cells. Plaque forming unit equivalents are units of measure of inactivated virus. In some embodiments, plaque forming unit equivalents are derived from plaque forming units for a sample prior to inactivation. In embodiments, plaque forming units are abbreviated "Pfu".

The terms "multiplicity of infection" or "MOI" are used according to its plain ordinary meaning in Virology and refers to the ratio of components (e.g., poxvirus) to the target (e.g., cell) in a given area. In embodiments, the area is assumed to be homogenous.

The term "replicate" is used in accordance with its plain ordinary meaning and refers to the ability of a cell or virus to produce progeny. A person of ordinary skill in the art will immediately understand that the term replicate when used in connection with DNA, refers to the biological process of producing two identical replicas of DNA from one original DNA molecule. In the context of a virus, the term "replicate" includes the ability of a virus to replicate (duplicate the viral genome and packaging said genome into viral particles) in a host cell and subsequently release progeny viruses from the host cell, which results in the lysis of the host cell. A "replication-competent" virus as provided herein refers to a virus (chimeric poxvirus) that is capable of replicating in a cell (e.g., a cancer cell).

As used herein, the term "oncolytic virus" is a virus that preferentially infects and kills cancer cells. As the infected cancer cells are destroyed by oncolysis, they release new infectious virus particles or virions to help destroy the remaining tumor. Oncolytic viruses are thought not only to cause direct destruction of the tumor cells, but also to stimulate host anti-tumor immune system responses. In embodiments, the oncolytic virus is able to replicate in a cancer cell. In embodiments, the oncolytic virus does not detectably replicate in a healthy cell relative to a standard control.

As used herein, the term "recombinant" refers to molecules formed by laboratory methods of genetic engineering (i.e. molecular cloning) to generate genetic material or proteins, creating sequences that may not otherwise be found in nature. For example, a recombinant protein may be a protein generated through combining two or more genes that originally encoded separate proteins. As used herein, the term "recombinant virus" or "recombinant oncolytic virus" is a virus produced by recombining pieces of DNA using recombinant DNA technology.

As used herein, the term "promoter" refers to a sequence of DNA which proteins bind to initiate gene expression. For example, transcription factors may bind a promoter region of a gene to transcribe RNA from DNA.

As used herein, the term "herpes simplex virus" or "HSV" refers to members of the Herpesviridae family. Herpes simplex virus 1 and 2 (HSV-1 and HSV-2), also known by their taxonomical names Human alphaherpesvirus 1 and Human alphaherpesvirus 2, are two members of the human Herpesviridae family, a set of viruses that produce viral infections in the majority of humans. Both HSV-1. (which produces most cold sores) and HSV-2 (which produces most genital herpes) are common and contagious.

As used herein, the term "γ34.5 gene" or "gamma-34.5 gene" refers to a herpes simplex virus gene whose function blocks the host cellular stress response to infection.

As used herein, the term "ICP6" or "ICP6 gene" refer to a gene that encodes a viral ribonucleotide reductase (vRR) function that allows replication of wild-type herpes simplex virus (HSV) to occur even in quiescent cells, such as the neurons. Without this function, HSV replication is severely curtailed in quiescent cells. However, cycling cells upregulate expression of S-phase specific genes such as mRR for their own nucleic acid metabolism, which complements the defective viral ICP6 function, thus allowing these mutant HSVs to replicate. This complementation provides a biologic rationale for employment of ICP6-defective 1-ISV in oncolytic therapy, rationale based on their preferential replication in cycling versus quiescent cells.

Antibodies are large, complex molecules (molecular weight of ~150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region, involved in binding the target antigen, and a constant ("C") region that interacts with other components of the immune system. The light and heavy chain variable regions (also referred to herein as light chain variable (VL) domain and heavy chain variable (VH) domain, respectively) come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site which docks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

An "antibody variant" as provided herein refers to a polypeptide capable of binding to an antigen and including one or more structural domains (e.g., light chain variable domain, heavy chain variable domain) of an antibody or fragment thereof. Non-limiting examples of antibody variants include single-domain antibodies or nanobodies, monospecific $Fab_2$, bispecific $Fab_2$, trispecific $Fab_3$, monovalent IgGs, scFv, bispecific antibodies, bispecific diabodies, trispecific triabodies, scFv-Fc, minibodies, IgNAR, V-NAR, hcIgG, VhH, or peptibodies. A "peptibody" as provided herein refers to a peptide moiety attached (through a covalent or non-covalent linker) to the Fc domain of an antibody. Further non-limiting examples of antibody variants known in the art include antibodies produced by cartilaginous fish or camelids. A general description of antibodies from camelids and the variable regions thereof and methods for their production, isolation, and use may be found in references WO97/49805 and WO 97/49805 which are incorporated by reference herein in their entirety and for all purposes. Likewise, antibodies from cartilaginous fish and the variable regions thereof and methods for their production, isolation, and use may be found in WO2005/118629, which is incorporated by reference herein in its entirety and for all purposes.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL), variable light chain (VL) domain or light chain variable region and variable heavy chain (VH), variable heavy chain (VH) domain or heavy chain variable region refer to these light and heavy chain regions, respectively. The terms variable light chain (VL), variable light chain (VL) domain and light chain variable region as referred to herein may be used interchangeably. The terms variable heavy chain (VH), variable heavy chain (VH) domain and heavy chain variable region as referred to herein may be used interchangeably. The Fc (i.e. fragment crystallizable region) is the "base" or "tail" of an immunoglobulin and is typically composed of two heavy chains that contribute two or three constant domains depending on the class of the antibody. By binding to specific proteins, the Fc region ensures that each antibody generates an appropriate immune response for a given antigen. The Fc region also binds to various cell receptors, such as Fc receptors, and other immune molecules, such as complement proteins.

The term "antibody" is used according to its commonly known meaning in the art. Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_{H1}$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)). The term "antibody" as referred to herein further includes antibody variants such as single domain antibodies. Thus, in embodiments an antibody includes a single monomeric variable antibody domain. Thus, in embodiments, the antibody, includes a variable light chain (VL) domain or a variable heavy chain (VH) domain. In embodiments, the antibody is a variable light chain (VL) domain or a variable heavy chain (VH) domain.

A single-chain variable fragment (scFv) is typically a fusion protein of the variable regions of the heavy (VH) and light chains (VL) of immunoglobulins, connected with a short linker peptide of 10 to about 25 amino acids. The linker may usually be rich in glycine for flexibility, as well as serine or threonine for solubility. The linker can either connect the N-terminus of the VH with the C-terminus of the VL, or vice versa.

The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

For preparation of suitable antibodies of the invention and for use according to the invention, e.g., recombinant, monoclonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633, 425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676, 980, WO 91/00360; WO 92/200373; and EP 03089).

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

As used herein, the term "cancer" is used in accordance with its plain ordinary meaning and refers to all types of cancer, neoplasm or malignant tumors found in mammals (e.g. humans), including leukemias, lymphomas, carcinomas and sarcomas. Examples of cancers that may be treated with a compound, composition, or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer. In embodiments, the cancer is glioblastoma, ovarian cancer, pancreatic cancer, myeloma, leukemia, or lymphoma.

The term "leukemia" is used in accordance with its plain ordinary meaning and refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3)

the increase or non-increase in the number abnormal cells in the blood-leukemic or aleukemic (subleukemic). Examples of leukemias that may be treated with a compound or method provided herein include, for example, acute non-lymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia. In embodiments, the cancer is acute myeloid leukemia.

The term "patient" or "subject in need thereof" is used in accordance with its plain ordinary meaning and refers to a living organism suffering from or prone to a disease or condition that can be treated by administration of a composition, compound, or method as provided herein. Non-limiting examples include humans, other mammals, bovines, rats, mice, dogs, monkeys, goat, sheep, cows, deer, and other non-mammalian animals. In some embodiments, a patient is human. In embodiments, the subject has, had, or is suspected of having cancer.

As used herein, the terms "control" or "control experiment" are used in accordance with its plain ordinary meaning and refer to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

As used herein, the terms "treating" or "treatment" are used in accordance with its plain ordinary meaning and refer to to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating includes preventing. In embodiments, treating does not include preventing.

As used herein, the term "prevent" is used in accordance with its plain ordinary meaning and refers to a decrease in the occurrence of disease symptoms in a patient. The prevention may be complete (no detectable symptoms) or partial, such that fewer symptoms are observed than would likely occur absent treatment.

By "therapeutically effective dose or amount" is intended an amount of cells, agents, or compounds described herein that brings about a positive therapeutic response in a subject in need of, such as an amount that restores function and/or results in the elimination and/or reduction of tumor and/or cancer cells. The exact amount (of cells or agents) required will vary from subject to subject, depending on the species, age, and general condition of the subject, the severity of the condition being treated, mode of administration, and the like. An appropriate "effective" amount in any individual case may be determined by one of ordinary skill in the art using routine experimentation, based upon the information provided herein. A "combined therapeutically effective dose or amount dose" refers a combination of therapies that together brings about a positive therapeutic response in a subject in need of, such as an amount that restores function and/or results in the elimination and/or reduction of tumor and/or cancer cells.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

A "synergistic amount" as used herein refers to the sum of a first amount (e.g., an amount of a compound provided herein) and a second amount (e.g., a therapeutic agent) that results in a synergistic effect (i.e. an effect greater than an additive effect). Therefore, the terms "synergy", "synergism", "synergistic", "combined synergistic amount", and "synergistic therapeutic effect" which are used herein interchangeably, refer to a measured effect of the compound administered in combination where the measured effect is greater than the sum of the individual effects of each of the compounds provided herein administered alone as a single agent.

In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the compound provided herein when used separately from the therapeutic agent. In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the therapeutic agent when used separately from the compound provided herein.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

As used herein, the term "immune response" is used in accordance with its plain ordinary meaning and refers to a response by an organism that protects against disease. The response can be mounted by the innate immune system or by the adaptive immune system, as well known in the art.

As used herein, the terms "natural killer cells" and "NK cells" are used in accordance with their plain ordinary meaning and refer to a type of cytotoxic lymphocyte involved in the innate immune system. The role NK cells play is typically analogous to that of cytotoxic T cells in the vertebrate adaptive immune response. NK cells may provide rapid responses to virus-infected cells, acting at around 3 days after infection, and respond to tumor formation. Typically, immune cells detect major histocompatibility complex (MHC) presented on infected cell surfaces, triggering cytokine release, causing lysis or apoptosis. NK cells typically have the ability to recognize stressed cells in the absence of antibodies and MHC, allowing for a much faster immune reaction.

As used herein, "Epidermal Growth Factor Receptor-chimeric antigen receptor natural killer cell" or "EGFR-CAR NK cell" refer to an NK cell that expresses a CAR targeting the EGFR antigen or an EGFR mutant. For example the EGFR-CAR NK cell may express a CAR including an scFv antibody domain that specifically binds the EGFR antigen or mutant.

As used herein, the term "T cells" or "T lymphocytes" are used in accordance with their plain ordinary meaning and refer to a type of lymphocyte (a subtype of white blood cell) involved in cell-mediated immunity. They can be distinguished from other lymphocytes, such as B cells and natural killer cells, by the presence of a T-cell receptor on the cell surface. T cells include, for example, natural killer T (NKT) cells, cytotoxic T lymphocytes (CTLs), regulatory T (Treg) cells, and T helper cells. Different types of T cells can be distinguished by use of T cell detection agents.

As used herein, the terms "tumor microenvironment", "TME", and "cancer microenvironment" are used in accordance with its plain ordinary meaning and refer to the non-neoplastic cellular environment of a tumor, including blood vessels, immune cells, fibroblasts, cytokines, chemokines, non-cancerous cells present in the tumor, and proteins produced.

As defined herein, the terms "activation", "activate", "activating", "activator" and the like are used in accordance with its plain ordinary meaning and refer to an interaction that positively affects (e.g. increasing) the activity or function of a protein or cell relative to the activity or function of the protein or cell in the absence of the activator. In embodiments activation means positively affecting (e.g. increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein that is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein As used herein, the terms "agonist," "activator," "upregulator," etc. are used in accordance with its plain ordinary meaning and refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As used herein, the terms "inhibition", "inhibit", "inhibiting" and the like are used in accordance with its plain ordinary meaning and refer to an interaction that negatively affecting (e.g. decreasing) the activity or function of the protein or cell relative to the activity or function of the protein or cell in the absence of the inhibitor. In embodiments, inhibition means negatively affecting (e.g. decreasing) the concentration or levels of the protein relative to the concentration or level of the protein in the absence of the inhibitor. In embodiments, inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein or cell from an indirect interaction (e.g. an inhibitor binds to a protein that activates the target protein, thereby preventing target protein activation or cell activations).

As used herein, the terms "inhibitor," "repressor" or "antagonist" or "downregulator" are used in accordance with its plain ordinary meaning and refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

As used herein, the term "expression" is used in accordance with its plain ordinary meaning and refers to any step involved in the production of a polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

As used herein, the term "cytokine" is used in accordance with its plain ordinary meaning and refers to a broad category of small proteins (~5-20 kDa) that are important in cell signaling. Cytokines are peptides, and cannot cross the lipid bilayer of cells to enter the cytoplasm. Cytokines are involved in autocrine signaling, paracrine signaling and endocrine signaling as immunomodulating agents.

Cytokines include chemokines, interferons, interleukins, lymphokines, and tumor necrosis factors. Cytokines are produced by a broad range of cells, including immune cells like macrophages, B lymphocytes, T lymphocytes and mast cells, as well as endothelial cells, fibroblasts, and various stromal cells; a given cytokine may be produced by more than one type of cell.

As used herein, the terms "IL-15", "interleukin-15" and "IL15" are used in accordance with their plain ordinary meaning and refer to a cytokine with structural similarity to interleukin-2 (IL-2). Like IL-2, IL-15 binds to and signals through a complex composed of IL-2/IL-15 receptor beta chain (CD122) and the common gamma chain (gamma-C, CD132). IL-15 is secreted by mononuclear phagocytes (and some other cells) following infection by virus(es). This cytokine induces cell proliferation of natural killer cells; cells of the innate immune system whose principal role is to kill virally infected cells. As a pleiotropic cytokine, it plays an important role in innate and adaptive immunity.

As used herein, the term "interleukin-15 receptor" refers to a type I cytokine receptor, binding interleukin-15. It consists of an interleukin 15 receptor, alpha subunit and shares common beta and gamma subunits with the IL-2 receptor.

As used herein, the term "interleukin 15 receptor, alpha subunit" or "IL-15-R alpha" or "IL-15-Rα" is a subunit of the interleukin 15 receptor.

As used herein, the term "sushi domain" refers to an evolutionarily conserved protein domain. Sushi domains exist in a wide variety of complement and adhesion proteins. The structure is known for this domain; it is based on a beta-sandwich arrangement—one face made up of three β-strands hydrogen-bonded to form a triple-stranded region at its center, and the other face formed. from two separate β-strands. For example, the IL-15-Rα sushi domain is a conserved portion of IL-15-Rα. The IL-15-Rα sushi domain is important for preserving binding function to IL-15.

For specific proteins described herein, the named protein includes any of the protein's naturally occurring forms, variants or homologs that maintain the protein transcription factor activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference, homolog or functional fragment thereof.

The term "IL-15Rα protein" or "IL-15Rα" as used herein includes any of the recombinant or naturally-occurring forms of Interleukin-15 receptor subunit alpha, CD215, or variants or homologs thereof that maintain IL-15Rα activity (e.g. within at least 50%, 80%, 90%, 95%, 96%, 97%, 98%, 99% or 100% activity compared to IL-15Rα). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring IL-15Rα protein. In embodiments, the IL-15Rα protein is substantially identical to the protein identified by the UniProt reference number Q13261 or a variant or homolog having substantial identity thereto.

The term "IL-15 protein" or "IL-15" as used herein includes any of the recombinant or naturally-occurring forms of Interleukin-15, or variants or homologs thereof that maintain IL-15 activity (e.g. within at least 50%, 80%, 90%, 95%, 96%, 97%, 98%, 99% or 100% activity compared to IL-15). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring IL-15 protein. In embodiments, the IL-15 protein is substantially identical to the protein identified by the UniProt reference number P40933 or a variant or homolog having substantial identity thereto.

The term "EGFR protein" or "EGFR" as used herein includes any of the recombinant or naturally-occurring forms of epidermal growth factor receptor (EGFR) also known as ErbB-1 or HER1 in humans, or variants or homologs thereof that maintain EGFR activity (e.g. within at least 50%, 80%, 90%, 95%, 96%, 97%, 98%, 99% or 100% activity compared to EGFR). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring EGFR protein. In embodiments, the EGFR protein is substantially identical to the protein identified by the UniProt reference number P00533 or a variant or homolog having substantial identity thereto.

As used herein, the term "immunotherapy" and "immunotherapeutic agent" are used in accordance with their plain ordinary meaning and refer to the treatment of disease by activating or suppressing the immune system. Immunotherapies designed to elicit or amplify an immune response are classified as activation immunotherapies, while immunotherapies that reduce or suppress are classified as suppression immunotherapies. Such immunotherapeutic agents include antibodies and cell therapy.

As used herein, the term "checkpoint inhibitor" is used in accordance with its plain ordinary meaning and refers to a drug, often made of antibodies, that unleashes an immune system attack on cancer cells. An important part of the immune system is its ability to tell between normal cells in the body and those it sees as "foreign." This lets the immune system attack the foreign cells while leaving the normal cells alone, To do this, it uses "checkpoints" which are molecules on certain immune cells that need to be activated (or inactivated) to start an immune response. Cancer cells sometimes find ways to use these checkpoints to avoid being attacked by the immune system. Drugs that target these checkpoints are known as checkpoint inhibitors.

As used herein, the term "PD-1" is used in accordance with its plain ordinary meaning and refers to a checkpoint protein on immune cells called T cells. It acts as a type of "off switch" that helps keep the T cells from attacking other cells in the body. It does this when it attaches to PD-L1, a protein on some normal (and cancer) cells. When PD-1 binds to PD-L1, the signal notifies the T cell to leave the other cell alone. Some cancer cells have large amounts of PD-L1, which helps them evade immune attack.

As used herein, the term "PD-L1" or "programmed death-ligand 1 (PD-L1)" refers to a 40 kDa type 1 transmembrane protein that plays a role in suppressing the adaptive arm of immune system during particular events such as pregnancy, tissue allografts, autoimmune disease and other disease states. It appears that upregulation of PD-L1 may allow cancers to evade the host immune system.

As used herein, the term "CLTA-4", "CTLA4" and "cytotoxic T-lymphocyte-associated protein 4)", also known as CD152 (cluster of differentiation 152), refer to a protein receptor that functions as an immune checkpoint and downregulates immune responses. CTLA4 is constitutively expressed in regulatory T cells but only upregulated in conventional T cells after activation—a phenomenon which is particularly notable in cancers. It acts as an "off" switch when bound to CD80 or CD86 on the surface of antigen-presenting cells.

As used herein, the term "anticancer agent" and "anticancer therapy" are used in accordance with their plain ordinary meaning and refer to a molecule or composition (e.g. compound, peptide, protein, nucleic acid, drug, antagonist, inhibitor, modulator) or regimen used to treat cancer through destruction or inhibition of cancer cells or tissues. Anticancer therapy includes chemotherapy, radiation therapy, surgery, targeted therapy, immunotherapy, and cell therapy Anticancer agents and/or anticancer therapy may be selective for certain cancers or certain tissues. In some embodiments, an anti-cancer therapy is an immunotherapy. In embodiments, anticancer agent or therapy may include a checkpoint inhibitor. In embodiments, the anti-cancer agent or therapy is a cell therapy.

In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclix-imab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta *Medica*), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta *Medica*), D-68144 (Asta *Medica*), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta *Medica*), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}In$, $^{90}Y$, or $^{131}I$, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, pembrolizumab nivolumab, atezolizumab, avelumab, durvalumab or the like.

As defined herein the terms “immune checkpoint”, “immune checkpoint protein” or “checkpoint protein” may be used interchangeably and referto molecules capable of modulating the duration and amplitude of physiological immune responses. Immune checkpoint molecules may stimulate (increase) an immune response. In embodiments, the checkpoint protein is a cellular receptor. Examples, of stimulatory checkpoint molecules include, but are not limited to, members of the tumor necrosis factor (TNF) receptor superfamily (e.g. CD27, CD40, OX40, glucocorticoid-induced TNFR family related gene (GITR), and CD137), members of the B7-CD28 superfamily (e.g. CD28 itself and Inducible T-cell costimulator (ICOS)). Alternatively, immune checkpoint molecules may inhibit (decrease) an immune response. Examples of inhibitory checkpoint molecules include, but are not limited to, adenosine A2A receptor (A2AR), B7-H3, B7-H4, BTLA, CTLA-4, indoleamine 2,3-dioxygenase (IDO), killer immunoglobulin-like receptors (KIR), LAG3, PD-1, TIM-3, and V-domain immunoglobulin suppressor of T-cell activation (VISTA) protein. Non-limiting examples of checkpoint inhibitors include, ipilimumab, pembrolizumab, nivolumab, talimogene laherparepvec, durvalumab, daclizumab, avelumab, and atezolizumab.

II. Oncolytic Virus Compositions

In an aspect, provided herein is a recombinant oncolytic virus including an expression cassette encoding a human IL15 domain and a human IL-15Rα sushi domain. In embodiments, the expression cassette includes the sequence of SEQ ID NO:3. In embodiments, expression cassette includes a sequence having 90% sequence identity to the sequence of SEQ ID NO:3. In embodiments, expression cassette includes a sequence having 91% sequence identity to the sequence of SEQ ID NO:3. In embodiments, expression cassette includes a sequence having 92% sequence identity to the sequence of SEQ ID NO:3. In embodiments, expression cassette includes a sequence having 93% sequence identity to the sequence of SEQ ID NO:3. In embodiments, expression cassette includes a sequence having 94% sequence identity to the sequence of SEQ ID NO:3. In embodiments, expression cassette includes a sequence having 95% sequence identity to the sequence of SEQ ID NO:3. In embodiments, expression cassette includes a sequence having 96% sequence identity to the sequence of SEQ ID NO:3. In embodiments, expression cassette includes a sequence having 97% sequence identity to the sequence of SEQ ID NO:3. In embodiments, expression cassette includes a sequence having 98% sequence identity to the sequence of SEQ ID NO:3. In embodiments, expression cassette includes a sequence having 99% sequence identity to the sequence of SEQ ID NO:3. In embodiments, expression cassette includes the sequence of SEQ ID NO:6. In embodiments, expression cassette includes a sequence having 90% sequence identity to the sequence of SEQ ID NO:6. In embodiments, expression cassette includes a sequence having 91% sequence identity to the sequence of SEQ ID NO:6. In embodiments, expression cassette includes a sequence having 92% sequence identity to the sequence of SEQ ID NO:6. In embodiments, expression cassette includes a sequence having 93% sequence identity to the sequence of SEQ ID NO:6. In embodiments, expression cassette includes a sequence having 94% sequence identity to the sequence of SEQ ID NO:6. In embodiments, expression cassette includes a sequence having 95% sequence identity to the sequence of SEQ ID NO:6. In embodiments, expression cassette includes a sequence having 96% sequence identity to the sequence of SEQ ID NO:6. In embodiments, expression cassette includes a sequence having 97% sequence identity to the sequence of SEQ ID NO:6. In embodiments, expression cassette includes a sequence having 98% sequence identity to the sequence of SEQ ID NO:6. In embodiments, expression cassette includes a sequence having 99% sequence identity to the sequence of SEQ ID NO:6. In embodiments, the expression cassette include the sequence of SEQ ID NO:3 and SEQ ID NO:6.

In embodiments, the recombinant oncolytic virus is selected from a recombinant adenovirus, reovirus, measles, herpes simplex, Newcastle disease virus, and vaccinia. In embodiments, the recombinant oncolytic virus is an adenovirus. In embodiments, the recombinant oncolytic virus is reovirus. In embodiments, the recombinant oncolytic virus is measles virus. In embodiments, the recombinant oncolytic virus is a Newcastle disease virus. In embodiments, the recombinant oncolytic virus is vaccinia virus. In embodiments, the recombinant oncolytic virus is an oncolytic herpes simplex virus (oHSV). In embodiments, the oHSV is a herpes simplex 1 virus. In embodiments, the oHSV is a herpes simplex 2 virus.

In embodiments, the recombinant oncolytic virus includes an expression cassette that further encodes a signal peptide sequence. In embodiments, the recombinant oncolytic virus includes an expression cassette that further encodes an IL-2 signal peptide sequence. In embodiments, the IL-2 signal peptide is encoded by a nucleic acid of SEQ ID NO:4.

In embodiments, the recombinant oncolytic virus does not include nucleic acid encoding a γ34.5 gene.

In embodiments, the recombinant oncolytic virus does not include nucleic acid encoding a functional ICP6 gene.

In embodiments, the recombinant oncolytic virus includes nucleic acid encoding an IL-15 domain and nucleic acid encoding an IL-15Rα sushi domain under the control of a viral or tumor specific gene promoter.

In embodiments, the recombinant oncolytic virus includes nucleic acid encoding the IL-15 domain and the nucleic acid encoding the IL-15Rαa sushi domain under the control of a herpes simplex virus (HSV) promoter. In embodiments, the HSV promoter is an immediate early (IE) promoter. In embodiments, the HSV IE promoter is an IE 4/5 promoter. In embodiments, the promoter includes the sequence of SEQ ID NO:6.

In embodiments, the recombinant oncolytic virus includes a nucleic acid encoding a marker within an ICP6 gene. In embodiments, the marker is a selectable marker.

In an aspect, provided herein is a pharmaceutical composition including a recombinant oncolytic virus as described above, and a pharmaceutically acceptable carrier.

In an aspect, provided herein is a combination therapy including a pharmaceutical composition that includes a recombinant oncolytic virus according to any embodiment described herein and a checkpoint inhibitor.

In embodiments, the checkpoint inhibitor is selected from a CTLA-4 inhibitor, a PD-1 inhibitor, and a PD-L1 inhibitor. In embodiments, the CTLA-4 inhibitor is ipilimumab. In embodiments, the checkpoint inhibitor is a PD-1 inhibitor. In embodiments, the PD-1 inhibitor is selected from pembrolizumab and nivolumab. In embodiments, the PD-1 inhibitor is pembrolizumab. In embodiments, the PD-1 inhibitor is nivolumab. In embodiments, the checkpoint inhibitor is a PD-L1 inhibitor. In embodiments, the PD-L1 inhibitor is selected from atezolizumab, avelumab, and durvalumab. In embodiments, the PD-L1 inhibitor is atezolizumab.

In embodiments, provided here is a combination therapy including a pharmaceutical composition that includes a recombinant oncolytic virus including an expression cassette encoding a human IL15 domain and a human IL-15Rα sushi domain and a checkpoint inhibitor. In embodiments, provided here is a combination therapy including a pharmaceutical composition that includes a recombinant oncolytic virus including an expression cassette encoding a human IL15 domain and a human IL-15Rα sushi domain and a PD-1 inhibitor. In embodiments, provided here is a combination therapy including a pharmaceutical composition that includes a recombinant oncolytic virus including an expression cassette encoding a human IL15 domain and a human IL-15Rα sushi domain and PD-L1 inhibitor. In embodiments, provided here is a combination therapy including a pharmaceutical composition that includes a recombinant oncolytic virus including an expression cassette encoding a human IL15 domain and a human IL-15Rα sushi domain and a CTLA-4 inhibitor.

In embodiments, provided here is a combination therapy including a pharmaceutical composition that includes a recombinant oncolytic herpes simplex virus including an expression cassette encoding a human IL15 domain and a human IL-15Rα sushi domain and a checkpoint inhibitor. In embodiments, provided here is a combination therapy including a pharmaceutical composition that includes a recombinant oncolytic herpes simplex virus including an expression cassette encoding a human IL15 domain and a human IL-15Rα sushi domain and a PD-1 inhibitor. In embodiments, provided here is a combination therapy including a pharmaceutical composition that includes a recombinant oncolytic herpes simplex virus including an expression cassette encoding a human IL15 domain and a human IL-15Rα sushi domain and PD-L1 inhibitor. In embodiments, provided here is a combination therapy including a pharmaceutical composition that includes a recombinant oncolytic herpes simplex virus including an expression cassette encoding a human IL15 domain and a human IL-15Rα sushi domain and a CTLA-4 inhibitor.

The compositions provided herein include pharmaceutical compositions including the recombinant oncolytic herpes simplex virus (HSV) provided herein including embodiments thereof and Epidermal Growth Factor Receptor-Chimeric Antigen Receptor Natural Killer (EGFR-CAR NK) cells. The compositions provided herein are contemplated to be effective for the treatment of cancers and inflammatory diseases. For example, compositions including the recombinant oncolytic HSV and EGFR-CAR NK cells may provide a synergistic effect in killing tumor cells compared to either treatment alone. Thus, in an aspect is provided a pharmaceutical composition including a first pharmaceutical dosage unit of the recombinant oncolytic virus provided herein including embodiments thereof, a second pharmaceutical dosage unit including EGFR-CAR NK cells, and a pharmaceutically acceptable carrier. In another aspect is provided a combination therapy including the pharmaceutical composition of provided herein including embodiments thereof and a checkpoint inhibitor.

III. Chimeric Antigen Receptors

In an aspect is provided a chimeric antigen receptor (CAR) that binds to wild-type and/or mutant EGFR including an extracellular and intracellular domain. The extracellular domain includes a target-specific binding element otherwise referred to as the antigen binding domain. In embodiments, the antigen binding domain includes an anti-EGFR antibody variable light chain domain. In embodiments, the anti-EGFR antibody variable light chain domain is a polypeptide encoded by the nucleic acid of SEQ ID NO:7. In embodiments, the antigen binding domain includes an anti-EGFR antibody variable heavy chain domain. In embodiments, the anti-EGFR antibody variable heavy chain domain is a polypeptide encoded by the nucleic acid of SEQ ID NO:8. In embodiments, the variable light chain domain and the variable heavy chain domain are connected by a linker. In embodiments, the linker is a polypeptide encoded by the nucleic acid of SEQ ID NO:9. The intracellular domain or cytoplasmic domain comprises a costimulatory signaling region and a zeta chain portion. In embodiments, the CAR includes a spacer domain of up to 300 amino acids, preferably 10 to 100 amino acids, more preferably 25 to 50 amino acids. For example, the chimeric antigen receptor may be the chimeric antigen receptor described in U.S. Patent. Pub No. 20180117146, which is incorporated herein by reference in its entirety for al purposes.

In an aspect is provided a chimeric antigen receptor (CAR) including: (a) an antigen binding domain of an anti-EGFR antibody that recognizes either or both wild type and/or mutant Epidermal Growth Factor Receptor (EGFR) ("wt EGFR and/or mutant EGFR"); (b) a hinge domain polypeptide; (c) a costimulatory molecule or polypeptide; and (d) a CD3 zeta signaling domain. In embodiments, the antigen binding domain includes an anti-EGFR antibody variable light chain domain. In embodiments, the anti-EGFR antibody variable light chain domain is a polypeptide encoded by the nucleic acid of SEQ ID NO:7. In embodiments, the antigen binding domain includes an anti-EGFR antibody variable heavy chain domain. In embodiments, the anti-EGFR antibody variable heavy chain domain is a polypeptide encoded by the nucleic acid of SEQ ID NO:8. In embodiments, the variable light chain domain and the variable heavy chain domain are connected by a linker. In embodiments, the linker is a polypeptide encoded by the nucleic acid of SEQ ID NO:9.

In embodiments, the CAR further includes a transmembrane domain. A "transmembrane domain" as provided herein refers to a polypeptide forming part of a biological membrane. The transmembrane domain provided herein is capable of spanning a biological membrane (e.g., a cellular membrane) from one side of the membrane through to the other side of the membrane. In embodiments, the transmembrane domain spans from the intracellular side to the extracellular side of a cellular membrane. Transmembrane domains may include non-polar, hydrophobic residues, which anchor the proteins provided herein including embodiments thereof in a biological membrane (e.g., cellular membrane of a T cell). Any transmembrane domain capable of anchoring the proteins provided herein including embodiments thereof are contemplated. Non-limiting examples of transmembrane domains include the transmembrane domains of CD28, CD8, CD4 or CD3-zeta. In embodiments, the transmembrane domain is a CD4 transmembrane domain. In embodiments, the transmembrane domain is a CD8 transmembrane domain that is linked to a CD8 hinge domain.

In embodiments, the transmembrane domain is a CD8 transmembrane domain. The term "CD8 transmembrane domain" as provided herein includes any of the recombinant or naturally-occurring forms of the transmembrane domain of CD8, or variants or homologs thereof that maintain CD8 transmembrane domain activity (e.g. within at least 50%, 80%, 90%, 95%, 96%, 97%, 98%, 99% or 100% activity compared to the CD8 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD8 transmembrane domain polypeptide. In embodiments, CD8 is the protein as identified by the NCBI sequence reference GI:225007534, homolog or functional fragment thereof.

In embodiments, the transmembrane domain is a CD28 transmembrane domain. The term "CD28 transmembrane domain" as provided herein includes any of the recombinant or naturally-occurring forms of the transmembrane domain of CD28, or variants or homologs thereof that maintain CD28 transmembrane domain activity (e.g. within at least 50%, 80%, 90%, 95%, 96%, 97%, 98%, 99% or 100% activity compared to the CD28 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD28 transmembrane domain polypeptide. In embodiments, CD28 is the protein as identified by the NCBI sequence reference GI:340545506, homolog or functional fragment thereof.

In embodiments, the transmembrane domain is a CD4 transmembrane domain. The term "CD4 transmembrane domain" as provided herein includes any of the recombinant or naturally-occurring forms of the transmembrane domain of CD4, or variants or homologs thereof that maintain CD4 transmembrane domain activity (e.g. within at least 50%, 80%, 90%, 95%, 96%, 97%, 98%, 99% or 100% activity compared to the CD4 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD4 transmembrane domain polypeptide. In embodiments, CD4 is the protein as identified by the NCBI sequence reference GI:303522473, homolog or functional fragment thereof.

In embodiments, the transmembrane domain is a CD3-zeta (also known as CD247) transmembrane domain. The term "CD3-zeta transmembrane domain" as provided herein includes any of the recombinant or naturally-occurring forms of the transmembrane domain of CD3-zeta, or variants or homologs thereof that maintain CD3-zeta transmembrane domain activity (e.g. within at least 50%, 80%, 90%, 95%, 96%, 97%, 98%, 99% or 100% activity compared to the CD3-zeta transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD3-zeta transmembrane domain polypeptide. In embodiments, CD3-zeta is the protein as identified by the NCBI sequence reference GI:166362721, homolog or functional fragment thereof.

In embodiments, the chimeric antigen receptor further includes an intracellular T-cell signaling domain. An "intracellular T-cell signaling domain" as provided herein includes amino acid sequences capable of providing primary signaling in response to binding of an antigen to the antibody region provided herein including embodiments thereof. In embodiments, the signaling of the intracellular T-cell signaling domain results in activation of the T cell expressing the same. In embodiments, the signaling of the intracellular T-cell signaling domain results in proliferation (cell division) of the T cell expressing the same. In embodiments, the signaling of the intracellular T-cell signaling domain results expression by said T cell of proteins known in the art to characteristic of activated T cell (e.g., CTLA-4, PD-1, CD28, CD69). In embodiments, the intracellular T-cell signaling domain is a CD3 ζ intracellular T-cell signaling domain.

In embodiments, the chimeric antigen receptor further includes an intracellular co-stimulatory T-cell signaling domain. An "intracellular co-stimulatory signaling domain" as provided herein includes amino acid sequences capable of providing co-stimulatory signaling in response to binding of an antigen to the antibody region provided herein including embodiments thereof. In embodiments, the signaling of the co-stimulatory signaling domain results in production of cytokines and proliferation of the T cell expressing the same. In embodiments, the intracellular co-stimulatory signaling domain is a CD28 intracellular co-stimulatory signaling domain, a 4-1BB intracellular co-stimulatory signaling domain, an ICOS intracellular co-stimulatory signaling domain, or an OX-40 intracellular co-stimulatory signaling domain. In embodiments, the intracellular co-stimulatory signaling domain is a CD28 intracellular co-stimulatory signaling domain. In embodiments, the intracellular co-stimulatory signaling domain is a 4-1BB intracellular co-stimulatory signaling domain. In embodiments, the intracellular co-stimulatory signaling domain is an ICOS intracellular co-stimulatory signaling domain. In embodiments, the intracellular co-stimulatory signaling domain is an OX-40 intracellular co-stimulatory signaling domain.

The term "CTLA-4" as referred to herein includes any of the recombinant or naturally-occurring forms of the cytotoxic T-lymphocyte-associated protein 4 protein, also known as CD152 (cluster of differentiation 152), or variants or homologs thereof that maintain CTLA-4 activity (e.g. within at least 50%, 80%, 90%, 95%, 96%, 97%, 98%, 99% or 100% activity compared to CTLA-4). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CTLA-4 protein. In embodiments, the CTLA-4 protein is substantially identical to the protein identified by the UniProt reference number P16410 or a variant or homolog having substantial identity thereto.

The term "CD28" as referred to herein includes any of the recombinant or naturally-occurring forms of the Cluster of Differentiation 28 protein, or variants or homologs thereof that maintain CD28 activity (e.g. within at least 50%, 80%, 90%, 95%, 96%, 97%, 98%, 99% or 100% activity compared to CD28). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD28 protein. In embodiments, the CD28 protein is substantially identical to the protein identified by the UniProt reference number P10747 or a variant or homolog having substantial identity thereto.

The term "CD69" as referred to herein includes any of the recombinant or naturally-occurring forms of the Cluster of Differentiation 69 protein, or variants or homologs thereof that maintain CD69 activity (e.g. within at least 50%, 80%, 90%, 95%, 96%, 97%, 98%, 99% or 100% activity compared to CD69). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD69 protein. In embodiments, the CD69 protein is substantially identical to the protein identified by the UniProt reference number Q07108 or a variant or homolog having substantial identity thereto.

The term "4-1BB" as referred to herein includes any of the recombinant or naturally-occurring forms of the 4-1BB protein, also known as tumor necrosis factor receptor superfamily member 9 (TNFRSF9), Cluster of Differentiation 137 (CD137) and induced by lymphocyte activation (ILA), or variants or homologs thereof that maintain 4-1BB activity (e.g. within at least 50%, 80%, 90%, 95%, 96%, 97%, 98%, 99% or 100% activity compared to 4-1BB). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring EGFR protein. In embodiments, the 4-1BB protein is substantially identical to the protein identified by the UniProt reference number Q07011 or a variant or homolog having substantial identity thereto.

IV. Methods of Use

In an aspect, provided herein is a method for killing tumor cells in a subject including administering to a subject an effective amount of the recombinant oncolytic virus according to any embodiment as described herein.

In an aspect, provided herein is a method of treating a patient having cancer including administering to the patient an effective amount of a pharmaceutical composition including a recombinant oncolytic virus as described above, and a pharmaceutically acceptable carrier as described herein or the recombinant oncolytic virus according to any embodiment as described herein.

In embodiments, the cancer is a chronic cancer. In embodiments, the cancer is a solid tumor. In embodiments, the cancer is selected an inflammatory chronic cancer. In embodiments, cancer is selected from glioblastoma, ovarian cancer, pancreatic cancer, leukemia, myeloma, and lymphoma. In embodiments, cancer is glioblastoma. In embodiments, cancer is ovarian cancer. In embodiments, cancer is pancreatic cancer. In embodiments, cancer is leukemia. In embodiments, cancer is myeloma. In embodiments, cancer is lymphoma.

In an aspect, provided herein is a method of treating a subject with an overactive immune system, including administering to the patient an effective amount of a pharmaceutical composition including a recombinant oncolytic virus as described above, and a pharmaceutically acceptable carrier as described herein or the recombinant oncolytic virus according to any embodiment as described herein.

In embodiments of methods of treating a subject with an overactive immune system, the subject has asthma or eczema. In embodiments, the subject has asthma. In embodiments, the subject has eczema. In embodiments of methods of treating a subject with an overactive immune system, the subject has allergic rhinitis.

In an aspect, provided herein is a method of treating a subject with an autoimmune disease, including administering to the patient an effective amount of a pharmaceutical composition including a recombinant oncolytic virus as described above, and a pharmaceutically acceptable carrier as described herein or the recombinant oncolytic virus according to any embodiment as described herein.

In embodiments, the autoimmune disease is selected from Type 1 diabetes, rheumatoid arthritis, and lupus. In embodiments, the autoimmune disease is Type 1 diabetes. In embodiments, the autoimmune disease is rheumatoid arthritis. In embodiments, the autoimmune disease is lupus.

In an aspect, provided herein is a method for increasing cytotoxicity of natural killer (NK) cells and/or CD8 T cells in a subject, including administering to the patient an effective amount of a pharmaceutical composition including a recombinant oncolytic virus as described above, and a pharmaceutically acceptable carrier as described herein or the recombinant oncolytic virus according to any embodiment as described herein.

In an aspect, provided herein is a method for increasing survival and/or proliferation of immune cells in a subject, including administering to the patient an effective amount of a pharmaceutical composition including a recombinant oncolytic virus as described above, and a pharmaceutically acceptable carrier as described herein or the recombinant oncolytic virus according to any embodiment as described herein.

In embodiments, the immune cell is a natural killer (NK) cell. In embodiments, the immune cell is a CD8 T cell.

In embodiments, the methods herein include administering to a subject the pharmaceutical composition provided herein including embodiments thereof. In embodiments, administering includes intratumoral, systemic, or intracavitary administration. In embodiments, administering is intratumoral administration. In embodiments, administering is systemic administration. In embodiments, administering is intracavitary administration.

In an aspect is provided a method for killing tumor cells in a subject including administering to a subject an effective amount of the pharmaceutical composition provided herein including embodiments thereof.

In an aspect is provided a method of treating a patient having cancer including administering to the patient an effective amount of the pharmaceutical composition provided herein including embodiments thereof.

For the methods provided herein, in embodiments, the cancer is a chronic cancer. In embodiments, the cancer is a solid tumor. In embodiments, the cancer is an inflammatory chronic cancer. In embodiments, the cancer is selected from glioblastoma, ovarian cancer, pancreatic cancer, leukemia, myeloma, and lymphoma. In embodiments, the cancer is glioblastoma. In embodiments, the cancer is ovarian cancer. In embodiments, the cancer is pancreatic cancer. In embodiments, the cancer is leukemia. In embodiments, the cancer is myeloma. In embodiments, the cancer is lymphoma.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

P EMBODIMENTS

P Embodiment 1. A recombinant oncolytic herpes simplex virus (HSV) comprising: an expression cassette encoding a human IL15 domain and a human IL-15Rα sushi domain.

P Embodiment 2. The recombinant oncolytic virus of P embodiment 1, wherein the expression cassette further encodes an IL-2 signal peptide sequence.

P Embodiment 3. The recombinant oncolytic virus of any of the preceding P embodiments, wherein the recombinant oncolytic virus does not comprise nucleic acid encoding a γ34.5 gene.

P Embodiment 4. The recombinant oncolytic virus of any of the preceding P embodiments, wherein the recombinant oncolytic virus does not comprise nucleic acid encoding a functional ICP6 gene.

P Embodiment 5. The recombinant oncolytic virus of any of the preceding P embodiments, wherein the nucleic acid encoding the IL-15 domain and the nucleic acid encoding the IL-15Rα sushi domain are under the control of a viral or tumor specific gene promoter.

P Embodiment 6. The recombinant oncolytic virus of any of one of the preceding P embodiments, wherein the nucleic acid encoding the IL-15 domain and the nucleic acid encoding the IL-15Rα sushi domain are under the control of herpes simplex virus (HSV) immediate early (IE) promoter.

P Embodiment 7. The recombinant oncolytic virus of P embodiment 6, wherein the HSV IE promoter is the IE 4/5 promoter.

P Embodiment 8. The recombinant oncolytic virus of any of the preceding P embodiments, wherein the recombinant oncolytic virus comprises a nucleic acid encoding a marker within an ICP6 gene.

P Embodiment 9. A pharmaceutical composition comprising: the recombinant oncolytic virus of any of the preceding P embodiments, and a pharmaceutically acceptable carrier.

P Embodiment 10. A combination therapy comprising the pharmaceutical composition of P embodiment 9 and a checkpoint inhibitor.

P Embodiment 11. A method for killing tumor cells in a subject comprising: administering to a subject an effective amount of the recombinant oncolytic virus of any of P embodiments 1-9.

P Embodiment 12. A method of treating a patient having cancer comprising administering to the patient an effective amount of the pharmaceutical composition of P embodiment 10 or the recombinant oncolytic virus of any of P embodiments 1-9.

P Embodiment 13. The method of P embodiment 12, wherein the cancer is a chronic cancer.

P Embodiment 14. The method of P embodiment 12, wherein the cancer is a solid tumor.

P Embodiment 15. The method of P embodiment 12, wherein the cancer is selected an inflammatory chronic cancer.

P Embodiment 16. The method of P embodiment 12, wherein the cancer is selected from glioblastoma, ovarian cancer, pancreatic cancer, leukemia, myeloma, and lymphoma.

P Embodiment 17. A method of treating a subject with an overactive immune system, comprising administering to the patient an effective amount of the pharmaceutical composition of P embodiment 10 or the recombinant oncolytic virus of any of P embodiments 1-9.

P Embodiment 18. The method of P embodiment 17, wherein the subject has asthma or eczema.

P Embodiment 19. The method of P embodiment 17, wherein the subject has allergic rhinitis.

P Embodiment 20. A method of treating a subject with an autoimmune disease, comprising administering to the patient an effective amount of the pharmaceutical composition of claim 10 or the recombinant oncolytic virus of any of P embodiments 1-9.

P Embodiment 21. The method of P embodiment 20, wherein the autoimmune disease is selected from Type 1 diabetes, rheumatoid arthritis, and lupus.

P Embodiment 22. A method for increasing cytotoxicity of natural killer (NK) cells and/or CD8 T cells in a subject, comprising administering an effective amount of the recombinant oncolytic virus of any of P embodiments 1-9.

P Embodiment 23. A method for increasing survival and/or proliferation of immune cells in a subject, comprising administering an effective amount the recombinant oncolytic virus of any of P embodiments 1-9.

P Embodiment 24. The method of P embodiment 23, wherein the immune cell is a natural killer (NK) cell.

P Embodiment 25. The method of P embodiment 23, wherein the immune cell is a CD8 T cell.

P Embodiment 26. The method of any of P embodiments 11-25, wherein administering is by intratumoral, systemic, or intracavitary administration.

EMBODIMENTS

Embodiment 1: A pharmaceutical composition comprising: a first pharmaceutical dosage unit of a recombinant oncolytic virus comprising an expression cassette encoding a human IL15 domain and a human IL-15Rα sushi domain, a second pharmaceutical dosage unit comprising Epidermal Growth Factor Receptor-Chimeric Antigen Receptor Natural Killer (EGFR-CAR NK) cells, and a pharmaceutically acceptable carrier.

Embodiment 2: A combination therapy comprising the pharmaceutical composition of embodiment 1 and a checkpoint inhibitor.

Embodiment 3: A method for killing tumor cells in a subject comprising: administering to a subject an effective amount of the pharmaceutical composition of embodiment 1 or 2.

Embodiment 4: A method of treating a patient having cancer comprising administering to the patient an effective amount of the pharmaceutical composition of embodiment 1 or 2.

Embodiment 5: The method of embodiment 4, wherein the cancer is a chronic cancer.

Embodiment 6: The method of embodiment 4 or 5, wherein the cancer is a solid tumor.

Embodiment 7: The method of any one of embodiments 4-6, wherein the cancer is an inflammatory chronic cancer.

Embodiment 8: The method of any one of embodiments 4-7, wherein the cancer is selected from glioblastoma, ovarian cancer, pancreatic cancer, leukemia, myeloma, and lymphoma.

EXAMPLES

Example 1: Experimental Background

Recent experiments produced an engineered oncolytic virus (oHSV-CDH1) to allow for the surface expression of CDH1, the gene encoding E-cadherin, on infected glioblastoma (GBM) cells. GBM infection with oHSV-CDH1 resulted in decreased clearance of the oHSV by immune cells in vivo thus allowing for viral spread and tumor lysis. This halting of viral clearance by immune cells is likely due to enhanced E-cadherin expression on oHSV-CDH1-infected GBM cells, which in turn acts as a ligand for the inhibitory receptor KLRG1 expressed on natural killer (NK) and T cells. Additionally and perhaps more importantly, oHSV-CDH1 enhanced the fusion of virus-infected GBM cells with non-infected GBM cells allowing for increased virus production and viral spread. (See, for example, Ref 3).

Scientists have recognized the ability of virus to kill tumor cells for nearly a century, yet clinical trials documenting a therapeutic benefit of oncolytic virus (OV) in patients with cancer has only occurred approximately over the past fifteen years. To date, only two genetically engineered oncolytic viruses have been approved as drugs. One is Oncorine (an E1B-deleted adenovirus) approved in China for head and neck cancer and esophagus cancer in 2005. The other one is T-Vec (talimogene laherparepvec, IMLYGIC, formerly OncoVEX$^{GM-CSF}$), which was approved by the FDA in the U.S. for melanoma in 2015 and was subsequently approved in Europe and Australia in 2016. Other oncolytic viruses that are tested in phase II/III clinical trials include G47Δ, which is a triple-mutated oncolytic HSV-1, JX-594 (pexastimogene devacirepvec, Pexa-Vec), which is a genetically engineered vaccinia virus carrying a mutated TK gene and a human GM-CSF gene, and CG0070, which is an oncolytic adenovirus targeting non-muscle invasive bladder cancer after *Bacillus* Calmette-Guerin (BCG) failure. (See, for example, Refs. 4-19).

The preclinical and clinical evidence noted above does support the notion that engineering viruses to infect tumors and express transgenes, including cytokines, can improve the efficacy of oncolytic virotherapy. Cytokines are key molecules involved in a wide variety of lymphocyte functions, such as survival, differentiation, proliferation, and activation. Interleukin (IL)-15 is a pleiotropic cytokine and was first identified in 1994 as a T lymphocyte growth factor and later was found to play a key role in the development, homeostasis, activation, and/or survival of T, NK, and NK-T cells as well as to have some functional importance in B cells, dendritic cells (DC), macrophages, and mast cells. Murine IL-15 shares about 70% amino acid sequence with human IL-15 and both human and murine IL-15 have similar properties of trans-presentation, signal transduction, and biological consequences of the ligand binding to its receptor. Three receptors, IL-15 receptor alpha (IL-15Rα), IL-2/15Rβ (also known as CD122), and the common gamma subunit (γc, also known as CD132) are required to mediate IL-15 signaling. While IL-15 is able to interact with its receptors in cis- and trans-manner, the trans-presentation is the primary mechanism for delivering the IL-15 signal. The extra cellular domain of both murine and human IL-15Rα contains a Sushi domain, a motif important for protein-protein interaction, while the cytoplasmic domain of IL-15Rα is not necessary for IL-15 trans-presentation. The mature IL-15Rα also contains other 4 domains, a linker/hinge region, the Pro/Thr-rich domain, the transmembrane domain and cytoplasmic tail. IL-15 and its IL-15/IL-15Rα complex are both actively being tested in phase I and II clinical trials with evidence of immune modulation in patients. (See, for example, Refs. 20-36).

In experiments herein, a novel herpes simplex 1-based new oncolytic virus secreting soluble IL-15/IL-15Rα (encoded by the nucleic acid of SEQ ID NO:3), named OV-IL15C, was constructed and tested for the treatment of glioblastoma (GBM). In vitro, data showed that soluble OV-IL15C was successfully secreted from virally infected GBM cells at the level of hundreds of pg per ml. IL-15/IL-15Rα secreted from virally infected GBM cells promoted proliferation, cytotoxicity, and cytokine production of natural killer (NK) cells and/or CD8 T cells. In vivo, OV-IL15C improved virotherapy in GBM in comparison to OV without IL-15 secretion. In vitro and in vivo studies also suggested that OV-IL15C is a safe approach for cancer treatment. Collectively, OV-IL15C may be an effective and safe approach for the treatment of cancer including GBM with a great potential to be translated into the clinic.

In the experiments described herein, a novel oncolytic herpes simplex virus (oHSV) expressing a soluble complex of human IL-15 interacting with the IL-15a Sushi domain (OV-IL15C) was generated. Intratumoral administration of OV-IL15C to mice bearing fatal GBM resulted in a significant prolongation of survival as well as enhancement of NK cell and CD8 T cell function when compared to administration of oHSV alone. The in vivo studies provide proof-of-concept that OV-IL15C can be an effective and safe approach to improve outcomes of GBM treatment.

Example 2: Methods

Cell Culture

Vero cells (derived from monkey kidney epithelial cells) were used for viral production and plaque assay-based viral titration. Human embryonic kidney 293 cells (derived from human embryonic kidney cells) were used for IL-15/IL-15Rα complex production. Human GBM cell lines (U251, LN229, Gli36, and U87) and mouse GBM cell line (G1261N4), as well as Vero and 293T cells, were cultured in DMEM media (Gibco) supplemented with 10% fetal bovine serum (FBS), penicillin (100 U/ml) and streptomycin (100 μg/ml). G1261N4 cells were modified from G1261 to express human nectin-1 to allow permissiveness to oHSV infection. GBM30 spheroid cells derived from a GBM patient and modified to express luciferase (named GBM30-luci) were used for in vivo imaging[3, 37]. GBM30 and GBM30-luci cells were maintained with neurobasal media (DMEM/F12) supplemented with 2% B27 (Gibco), human epidermal growth factor (Stemcell), basic fibroblast growth factor (Stemcell), heparin (Stemcell) and Glutamax (Gibco) in low-attachment cell culture flasks. All cell lines were routinely tested for the presence of *mycoplasma* using MycoAlert™ PLUS *Mycoplasma* Detection Kit (VWR #75866-212). Human primary cells used for tropism test were purchased from ScienCell and cultured following manufacturer's instructions. These cells including human oral fibroblasts, pulmonary microvascular endothelial cells (HPMEC), hepatic sinusoidal endothelial cells (HHSEC), pulmonary alveolar epithelial cells (HPAEpiC), neurons (HN), and neurons-midbrain (HN-mb).

Virus Production and Titration

In the experiments herein, the sequence of human IL-15/IL-15Rα complex contained an IL-2 signal peptide to enhance secretion of the product into the supernatant. The IL-2 signal peptide is encoded by a nucleic acid of SEQ ID NO:4. An HA tag was fused to the sequence of IL-15/IL-15Rα complex at the 3' end to detect the secreted complex after its production. The HA tag may be encoded by a nucleic acid of SEQ ID NO:5. The new virus was named OV-IL15C, which was created using the fHsvQuik-1 system as previously described[3]. Briefly, the full-length human IL15 and IL-15Rα Sushi domain DNA sequence was cloned into pT-oriSIE4/5 following the HSV pIE4/5 promoter (SEQ ID NO:6) to construct the pT-oriSIE4/5-IL-15/IL-15Rα complex. Then, pT-oriSIE4/5-IL-15/IL-15Rα complex was used to recombine with fHsvQuik-1 to engineer OV-IL15C. The new virus was propagated and titrated using Vero cells. Virus titration was performed using plaque assay. Briefly, one day before infection, Vero cells were seeded at a concentration of $2\times10^4$/well in a 96-well plate. The next day, the confluency of Vero cells reached 70%-80% at which time the cells were infected with gradient diluted parental oHSV control OV-Q1 or OV-IL15C viral solutions (1:10/1:100/1:1000/1:10000). Four hours after infection, the media were replaced with fresh DMEM media. GFP-positive plaques were counted with a Zeiss fluorescence microscope (AXIO observer) 2 days after infection in order to determine the virus titration.

Plaque Forming Assay

To evaluate the viral production and infection behavior of OV-IL15C, plaque forming assays were undertaken with GBM cell lines U251 and LN229 infected with OV-Q1 or OV-IL15C at a MOI of 0.005 or 5. Four hours after infection, the media were replaced with fresh media. The plaques in each group were imaged by using the Zeiss fluorescent microscopy at 24, 48, 72 and 96 hpi (hours post infection).

Detection and Quantification of OV-IL15C

One day before infection, 293T cells were seeded $0.5\times10^6$/well in a 24-well plate. On the second day when the confluency of 293T cells reached 70%-80%, the cells were infected with parental oHSV control OV-Q1 or OV-IL15C at a MOI of 2 and uninfected cells were used as negative control. Two days later, cell lysates were prepared with RIPA Lysis and Extraction Buffer (Thermo Fisher #89900) containing Protease/Phosphatase inhibitor cocktail (Halt™

#78440). Protein concentration was assessed using a Rapid Gold BCA Protein Assay Kit (Pierce™ #A53226). Samples were loaded for sodium dodecyl sulfate (SDS)-polyacrylamide gel electrophoresis and separated proteins were transferred onto the PVDF membranes (BIO-RAD #100-26933). After blocking the membrane with 5% bovine serum albumin (BSA, Sigma-Aldrich #A3294-10G), the primary anti-HA-tag antibody (Cell Signaling Technology (CST), clone: C29F4, #3724) was added for an overnight incubation at 4° C., followed by an incubation with anti-rabbit secondary antibody (CST #7074) for one hour at room temperature.

Human GBM cell lines U251 and LN229 were used to infect with parental oHSV control OV-Q1 or OV-IL15C at a MOI of 2 and uninfected cells served as control. Supernatants were collected 24 hr, 48 hr, 72 hr, and 96 hpi, followed by quantifying the IL-15/IL-15Rα complex using a DuoSet enzyme-linked immunosorbent assay (ELISA) kit (R&D, DY6924). The assays were performed in at least three biological replicates.

Cytotoxicity Assays

Human primary NK cells and CD8 T cells were isolated from peripheral blood mononuclear cells (PBMCs) from normal donors by using an EasySep™ Human NK Cell Isolation Kit (#17955) and Human CD8 Selection Kit II (#17853) from StemCell. The centrifugal filter (Millipore Sigma #UFC901024) was used to enrich the IL-15/IL-15Rα complex in the supernatants from uninfected or parental oHSV control OV-Q1- or OV-IL15C-infected U251 cells at a ratio of 5:1. The enriched supernatants were used to pre-incubate primary NK cells for 18 hours or CD8 T cells for 48 hours at 37° C., followed by cytotoxicity assays with K562 myeloid leukemia cell line or the GBM30 GBM cell line as target cells. Two methods were used to test the cytotoxicity function: one was a flow cytometry-based assay and another one was a $^{51}$Cr-release cytotoxicity assay. For the flow cytometry-based assay, target cells were labeled with an APC-dye (BD, #565082) for 20 minutes at 37° C. and were co-cultured with effector cells, which were primary human NK cells that had been pre-incubated with supernatants from uninfected or virus-infected U251 GBM cells for 18 hours in a round bottom 96-well plate at 37° C. for 4 hours for NK cells or 12 hours for CD8 T cells. The target cells in each well were $5\times10^3$. Effector and target cells ratios were 20:1, 10:1, 5:1, and 2.5:1 for NK cells and 50:1, 25:1, 12.5:1, and 6.25:1 for CD8 T cells. The dead cells were stained by SYTOX™ Blue Dead Cell Stain (Thermo Fisher #S34857). For the $^{51}$Cr release assay, effector cells were NK cells that had been pre-incubated with supernatants from uninfected or virus-infected U251 GBM cells for 18 hr and target cells were K562 and GBM30 cells that were labeled with $^{51}$Cr for 1.5 hr. The effector cells and target cells were co-incubated in a round bottom 96-well plate at 37° C. for 4 hours at different effector:target ratios (40:1, 20:1, 10:1, and 5:1). The assays were performed in at least three technical replicates with human NK cells and CD8 T cells from different donors (n=4 for NK cells and n=5 for T cells). Only flow cytometry-based assay was undertaken for CD8 T cells as $^{51}$Cr-labeled target cells died in the 12-hour culture even in the absence of effector cells.

Assessment of NK Cell Survival and Proliferation

Supernatants from uninfected or OV-Q1- and OV-IL15C-infected U251 cells were used as media to culture NK cells in absence of IL-2. From Day 1 to Day 4, the numbers of NK cells in each group were counted after cells were stained with TypeBlue (Thermo Fisher). The assays were performed in at least three technical replicates with human NK cells from different donors (n=3).

Example 3: Results

Generation and Titration of Recombinant OV-IL15C

Figure 1B:
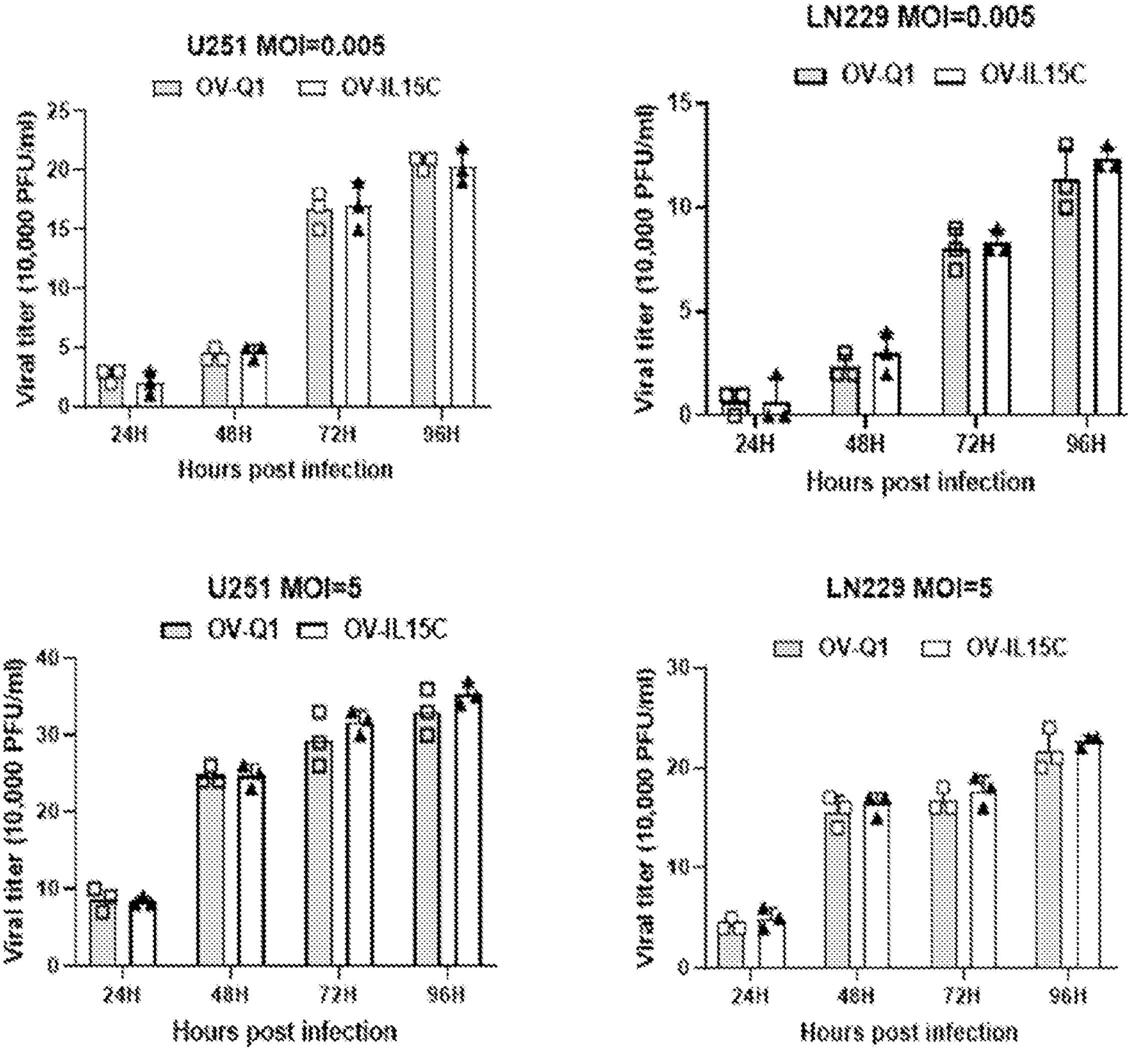

A new oHSV was successfully engineered and named OV-IL15C. It expressed a fusion protein containing human IL-15 and IL-15Rα Sushi domain. The expression of the fusion protein was driven by the HSV-1 immediate early gene promoter pIE4/5 (SEQ ID NO:6). The genetic maps of wild-type human HSV-1, parental oHSV control OV-Q1 and OV-IL15C) are shown in FIG. 1A. Next, the viral production capacity of OV-IL15C was evaluated at an unsaturated (MOI=0.005) or saturated (MOI=S) level. Results proved that OV-IL15C-infected U251 and LN229 human GBM cell lines produced similar amounts of corresponding viruses compared to parental oHSV control OV-Q1-infected cells (FIG. 1B). Therefore, the OV-IL15C engineered to secrete the IL-15/IL-15Rα complex did not affect its viral production capacity.

Figure 1C:
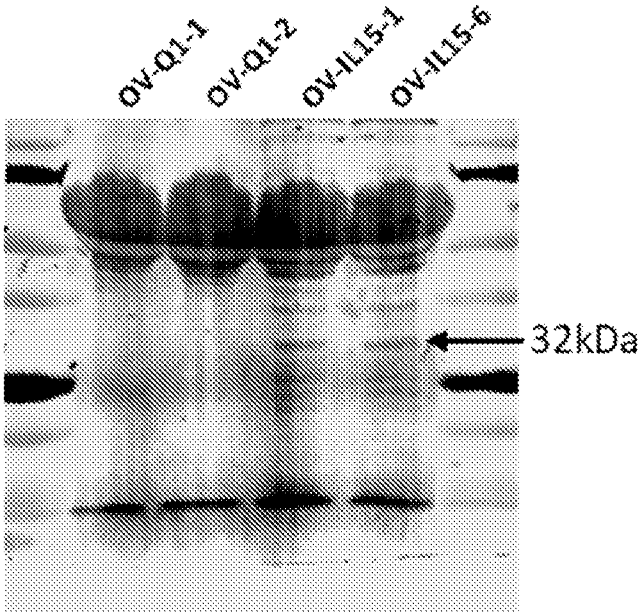
Figure 1D:
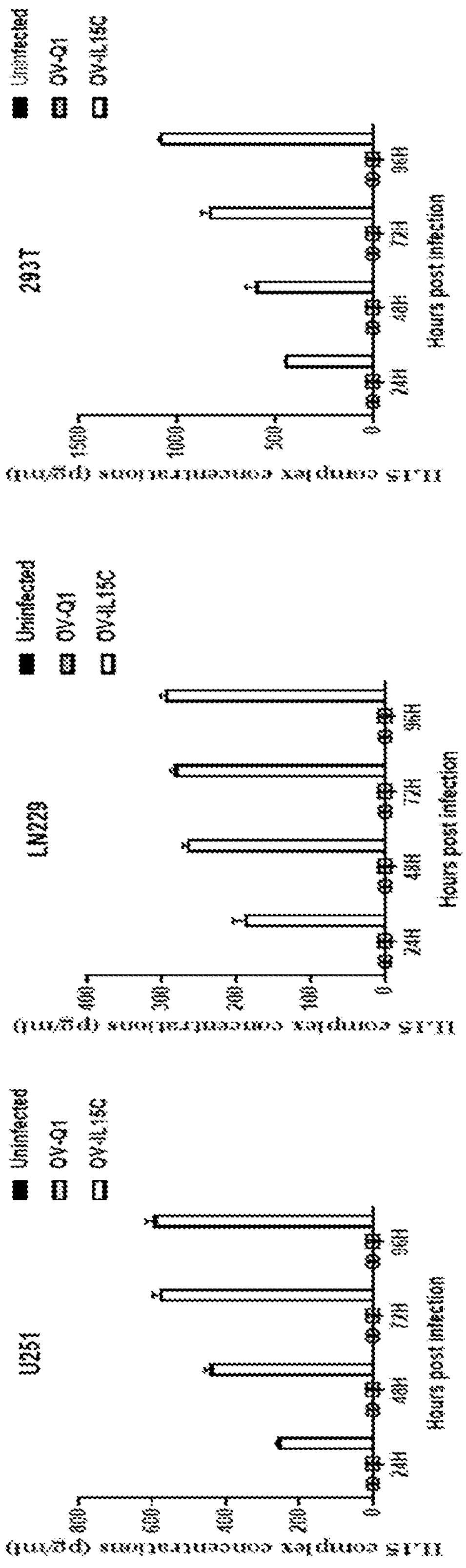
Figure 1E:
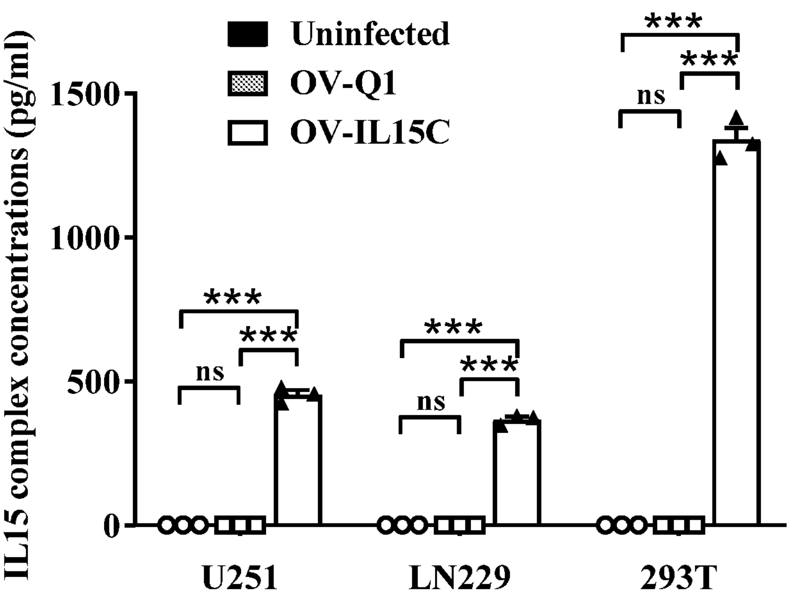

Detection and Quantification of IL-15/IL-15Rα Complex after OV-IL15C Infection of GBM Immunoblotting and specific ELISA test were used to identify and quantify the expression of the IL-15/IL-15Rα complex. For this, 293T cells were first infected by the parental oHSV control OV-Q1 or OV-IL15C at a MOI of 2. Uninfected 293T cells were also used as control group. Cells were harvested 48 hours post infection (hpi) for sodium dodecyl sulfate (SDS)-polyacrylamide gel electrophoresis. Immunoblotting with an HA-tag antibody showed the IL15/IL-15Rα complex with a correct size of 32 kDa (FIG. 1C). Next, U251 and LN229 GBM cells were infected with the parental oHSV control OV-Q1- and OV-IL15C. The supernatants of these infected cells were assessed for quantification of the IL-15/IL-15Rα complex by ELISA, which was present only in the supernatants of cells infected with OV-IL15C. The concentration of the complex increased in a time-dependent manner with approximately 600 pg/ml, 300 pg/ml, 1,000 pg/ml in OV-IL15C-infected U251 GBM cells, LN229 GBM cells and 293T cells at the MOI of 0.05 at 96 hpi, respectively (FIG. 1D). The complex was undetectable in uninfected and parental oHSV control OV-Q1-infected GBM cells (FIG. 1E). These results demonstrated that OV-IL15C-infected cells can continuously produce the IL-15/IL-15Rα until OV-infected cells are lysed by the oncolytic virus itself.

Figure 2A:
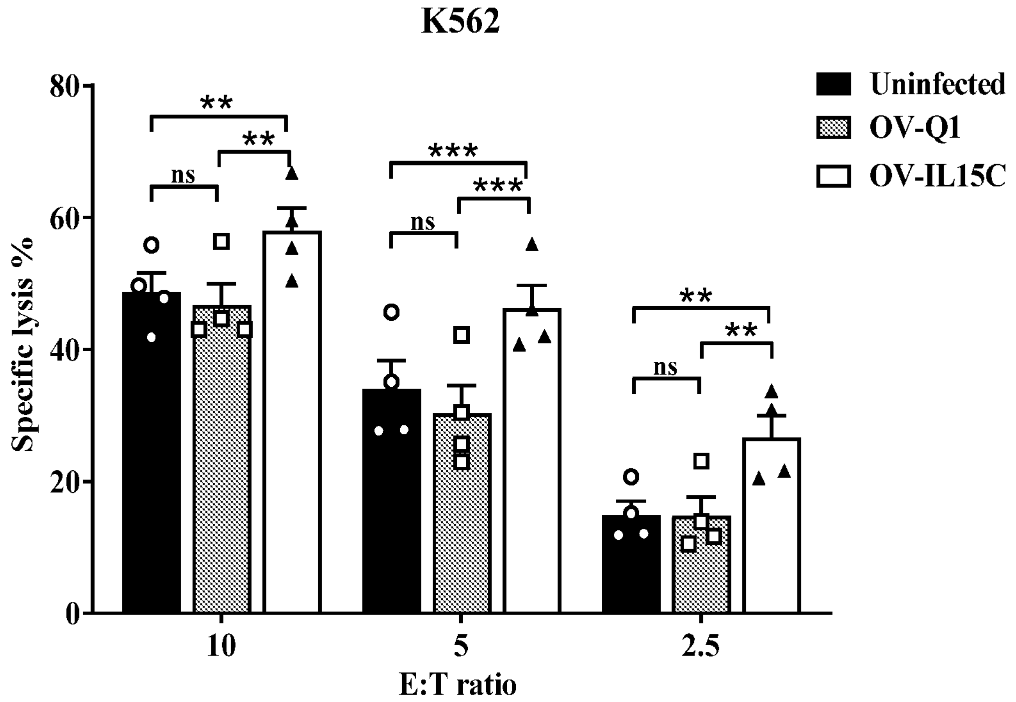
FIGS. 2A-2D demonstrates that IL-15/IL-15Rα complex secreted by OV-IL15C-infected GBM cells enhances NK cell cytotoxicity in vitro.
Figure 2B:
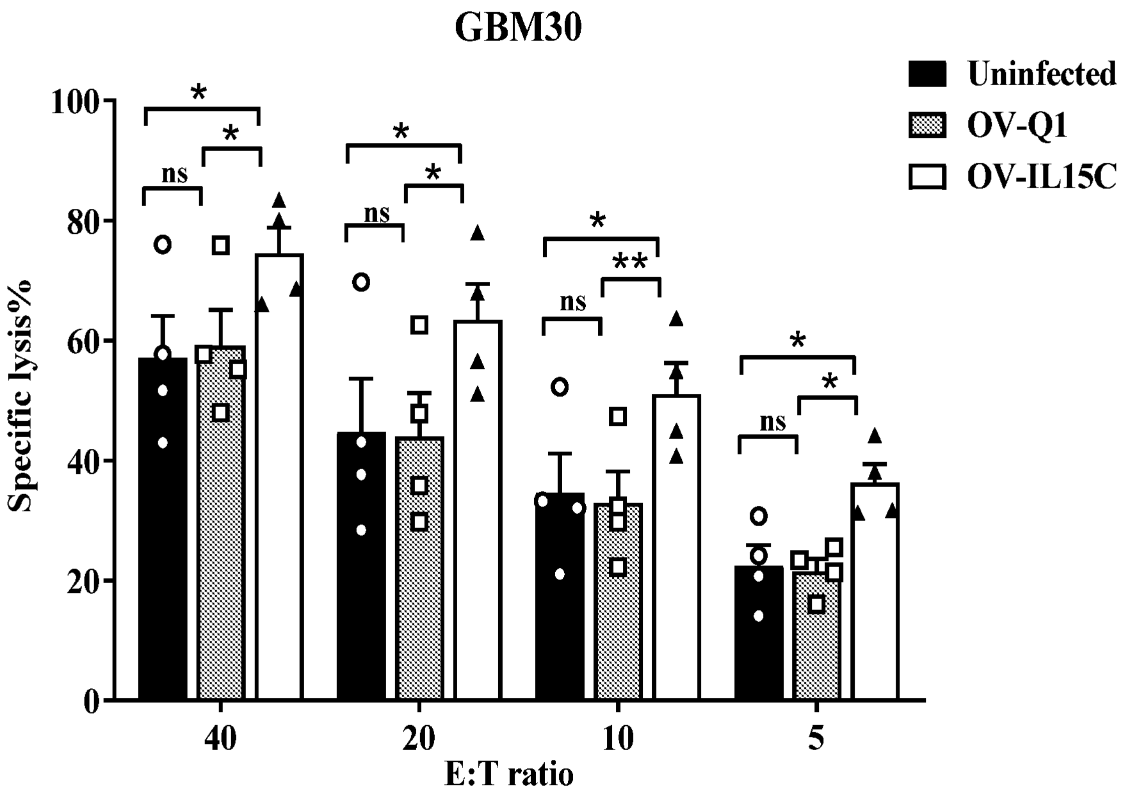
Figure 2C:
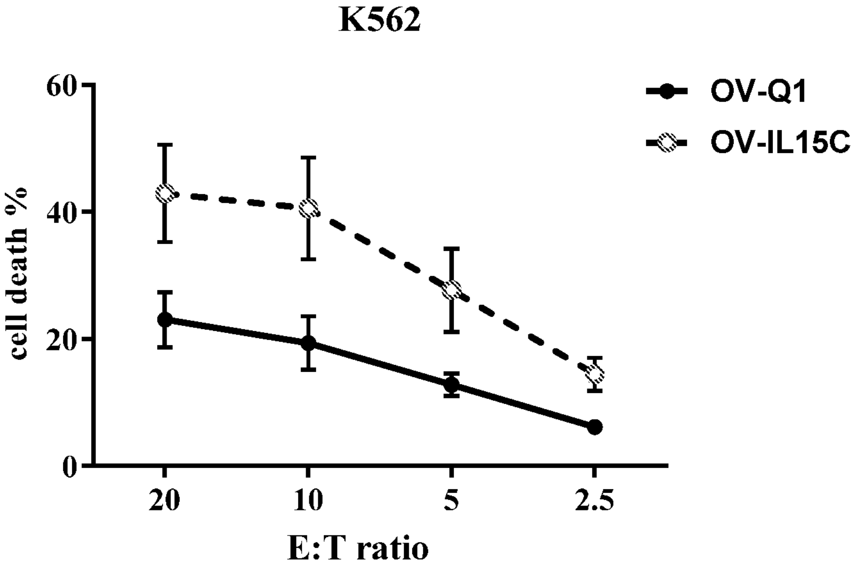
Figure 2D:
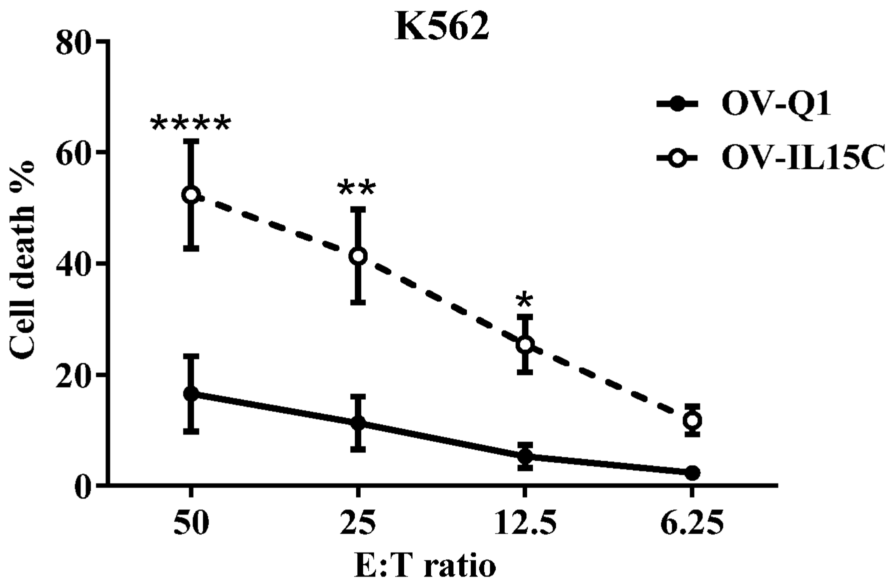
Figure 3A:
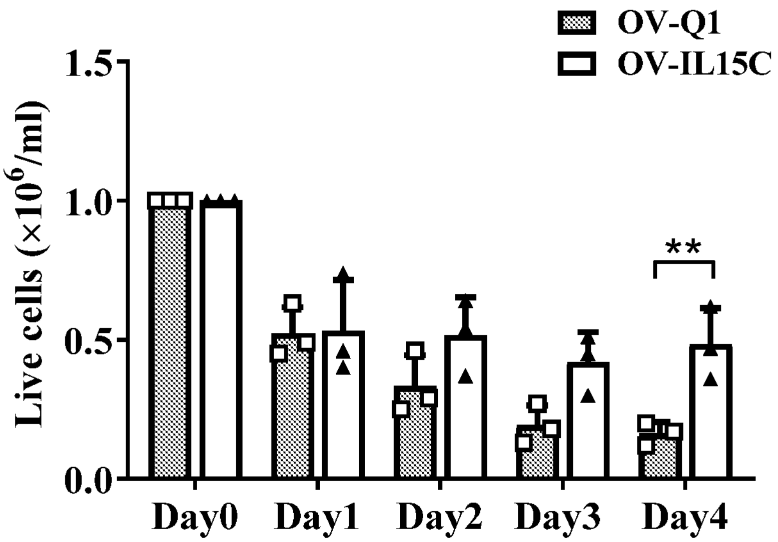
FIGS. 3A and 3B demonstrate that IL-15/IL-15Rα complex secreted from OV-IL15CNK cells improves survival and proliferation of NK cells.
Figure 3B:
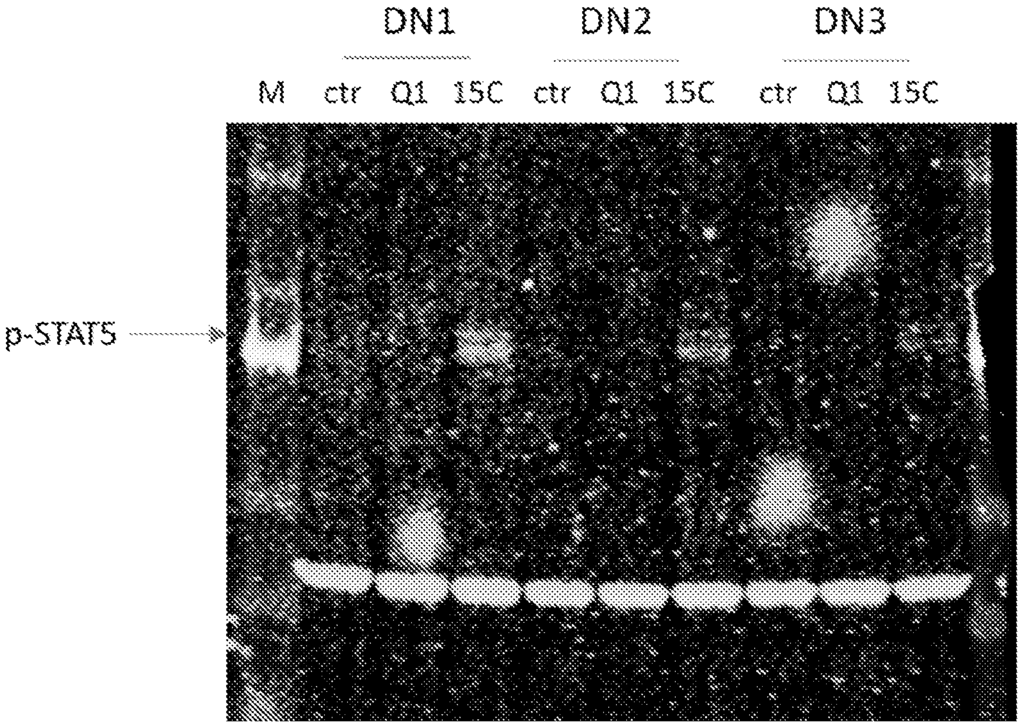

The IL-15/IL-15Rα Complex Secreted by OV-IL15C-Infected GBM Cells Enhances Cytotoxicity of NK Cells and CD8T Cells In Vitro A classic $^{51}$Cr release cytotoxicity was used to determine whether the IL-15/IL-15Rα complex secreted by OV-IL15C-infected GBM cells could enhance cytotoxicity of NK cells in vitro. For this, K562 cells, a classic MHC class 1 negative cell line sensitive to NK cell killing, were included as target cells. Results showed that the cytotoxicity of NK cells against K562 leukemia cells and GBM30 GBM cells in the presence of supernatants from OV-IL15C-infected U251 cells significantly increased compared to supernatants from uninfected or parental oHSV control OV-Q1-infected U251 GBM cells. (FIGS. 2A and 2B). Flow cytometry-based cytotoxicity assays were conducted to confirm the cytotoxicity data of NK cells collected from the $^{51}$Cr release cytotoxicity and similar results were observed (FIG. 2C). Flow cytometry-based cytotoxicity assays were also used to assess cytotoxicity of CD8 T effector cells against K562 or GBM30 target cells in the presence of concentrated supernatants of OV-Q1- or V-IL15C-infected U251 GBM cells. Similarly, data showed that the level of cytotoxicity of CD8 T cells against K562 or GBM30 cells in the presence of concentrated supernatants of OV-IL15C-infected U251 GBM cells was significantly increased when compared to CD8 T cells incubated with concentrated supernatants of Q1-infected U251 GBM cells (FIG. 2D).

The IL-15/IL-15Rα Complex Secreted by OV-IL15C-Infected GBM Cells Prolongs NK Cell Survive In Vitro In the absence of IL2 or other cytokines, primary NK cells do not survive for several days. However, data showed that the IL-15/IL-15Rα complex secreted by OV-IL15C-infected U251 GBM cells could increase NK cell survive compared to oHSV control OV-Q1-infected U251 GBM cells (p value will show here after adjust).

Example 4: An oHSV Expressing Soluble Human IL-15/IL-15Rα in Combination with EGFR-CAR NK Cells Improves Glioblastoma Treatment Interleukin (IL)-15 is a pleiotropic cytokine with multiple roles that improve immune responses to tumor cells. Oncolytic viruses can both specifically lyse tumors and activate the innate and adaptive immune response. The systemic administration of IL-15 alone or as a complex with the IL-15 receptor alpha is currently being tested in the clinic. Presented herein is a novel oncolytic herpes simplex virus (oHSV) that encodes and secretes a soluble human IL-15/IL-15Rα complex (encoded by the nucleic acid of SEQ ID NO:3), named OV-IL15C, to test its function for treatment of glioblastoma (GBM). In vitro, soluble IL-15/IL-15Rα complex was successfully secreted from OV-IL15C-infected GBM cells and promoted activation, cytotoxicity, and survival of natural killer (NK) and $CD8^+$ T cells. In vivo, results showed that OV-IL15C significantly prolongs mice survival compared to control groups. The anti-tumor activities of OV-IL15C treatment were closely associated with intracranial and splenic infiltration of NK and T cells. To improve the anti-tumor efficiency of OV-IL15C, NK cells were engineered with a chimeric antigen receptor (CAR) targeting EGFR and EGFRvIII, referred to as EGFR-CAR, in order to perform combination therapy. In vitro, frozen and readily available off-the-shelf EGFR-CAR NK cells show enhanced, antigen-dependent killing of tumor cells compared to empty vector-transduced NK cells. In vivo, OV-IL15C and off-the-shelf EGFR-CAR NK cells synergistically suppressed tumor growth and significantly improved survival compared to OV-IL15C or EGFR-CAR alone. Collectively, results described herein demonstrate the combination treatment with OV-IL15C and off-the-shelf EGFR-CAR NK cells represent a promising therapeutic strategy for GBM.

The combination of an OV expressing human IL-15/IL-15Rα sushi domain fusion protein (OV-IL15C) with off-the-shelf CAR NK cells was investigated for the purpose of improving anti-tumor efficacy in GBM. The frozen and readily available off-the-shelf CAR NK cells were produced from the blood of a single donor and armed with an anti-EGFR signal-chain variable fragment (referred to as EGFR-CAR), which is able to target both wild-type EGFR and EGFRvIII. Both OV-IL15C and EGFR-CAR NK cells demonstrated better cytotoxicity activity compared to control OV or empty vector (EV)-transduced NK cells in vitro, respectively. In vivo, the anti-tumor activities of OV-IL15C were closely associated with intracranial and splenic infiltration of NK and T cells. The combination of OV-IL15C and EGFR-CAR NK cells produced a synergistic anti-tumor effect and a significant prolongation of survival over either therapy alone.

Results

Generation of OV-IL15C and Quantification of IL-15/IL-15Rα Complex Secreted from Virally-Infected GBM Cells.

Figure 4A:
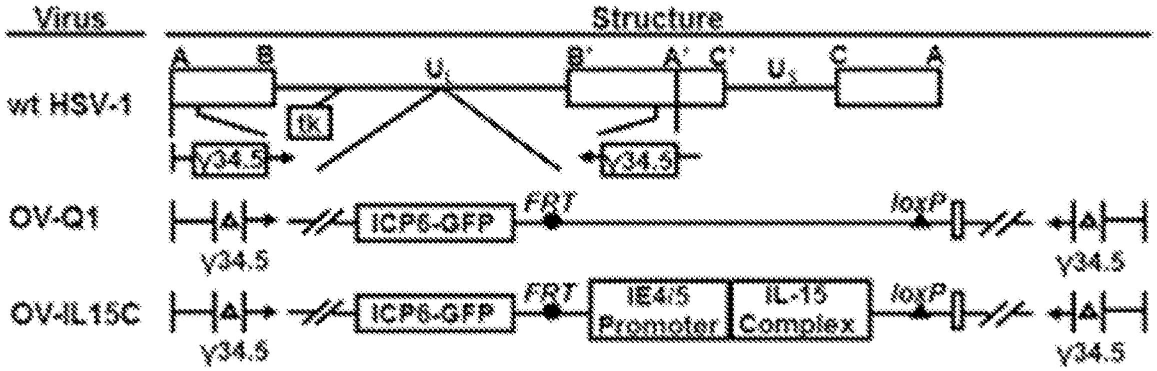
FIGS. 4A-4D show generation of OV-IL15C and quantification of the IL-15/IL-15Rα complex produced by OV-IL15C infection of GBM cells.
Figure 4B:
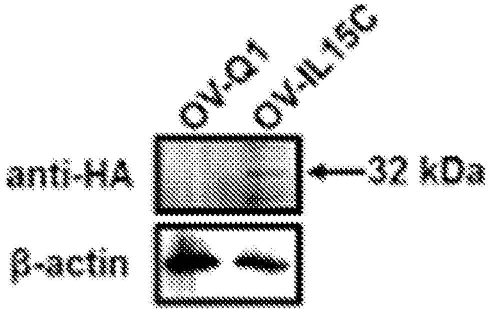
Figure 4C:
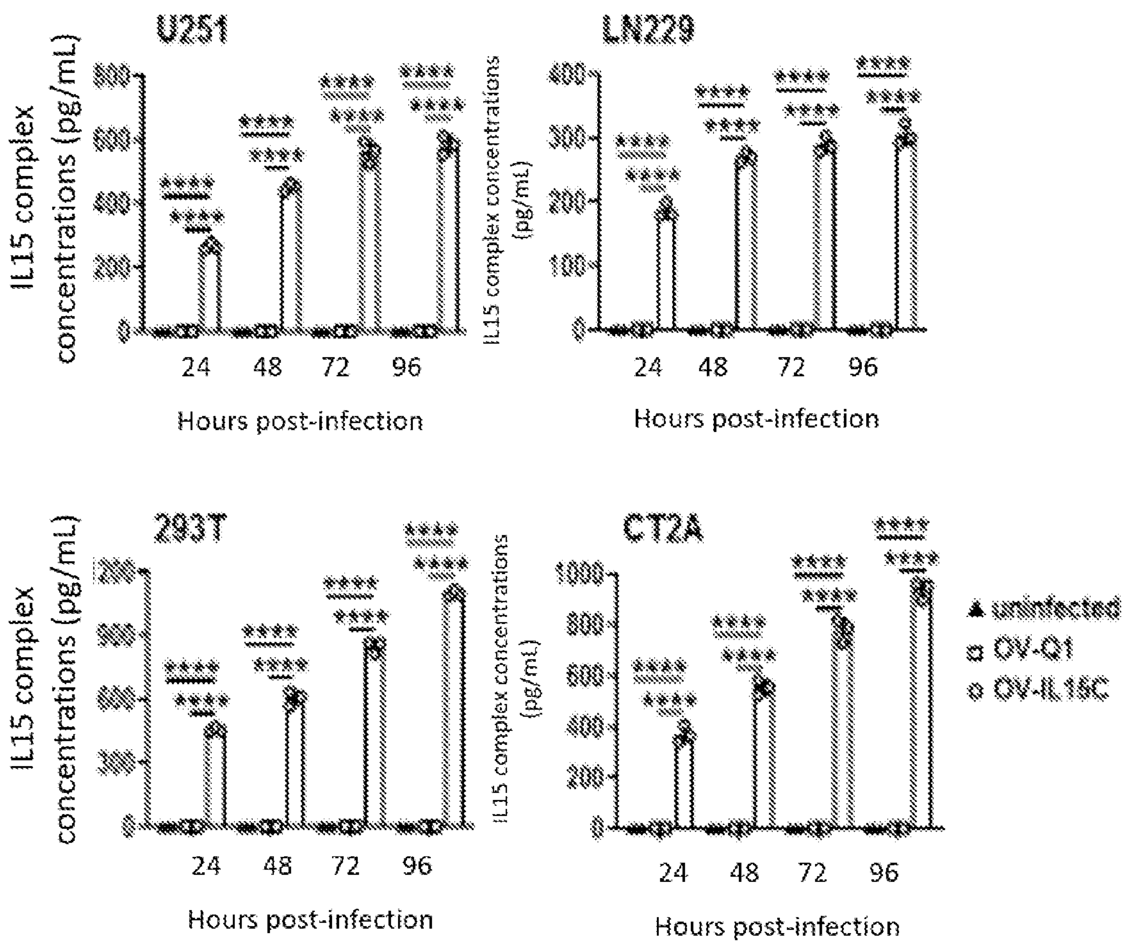
Figure 4D:
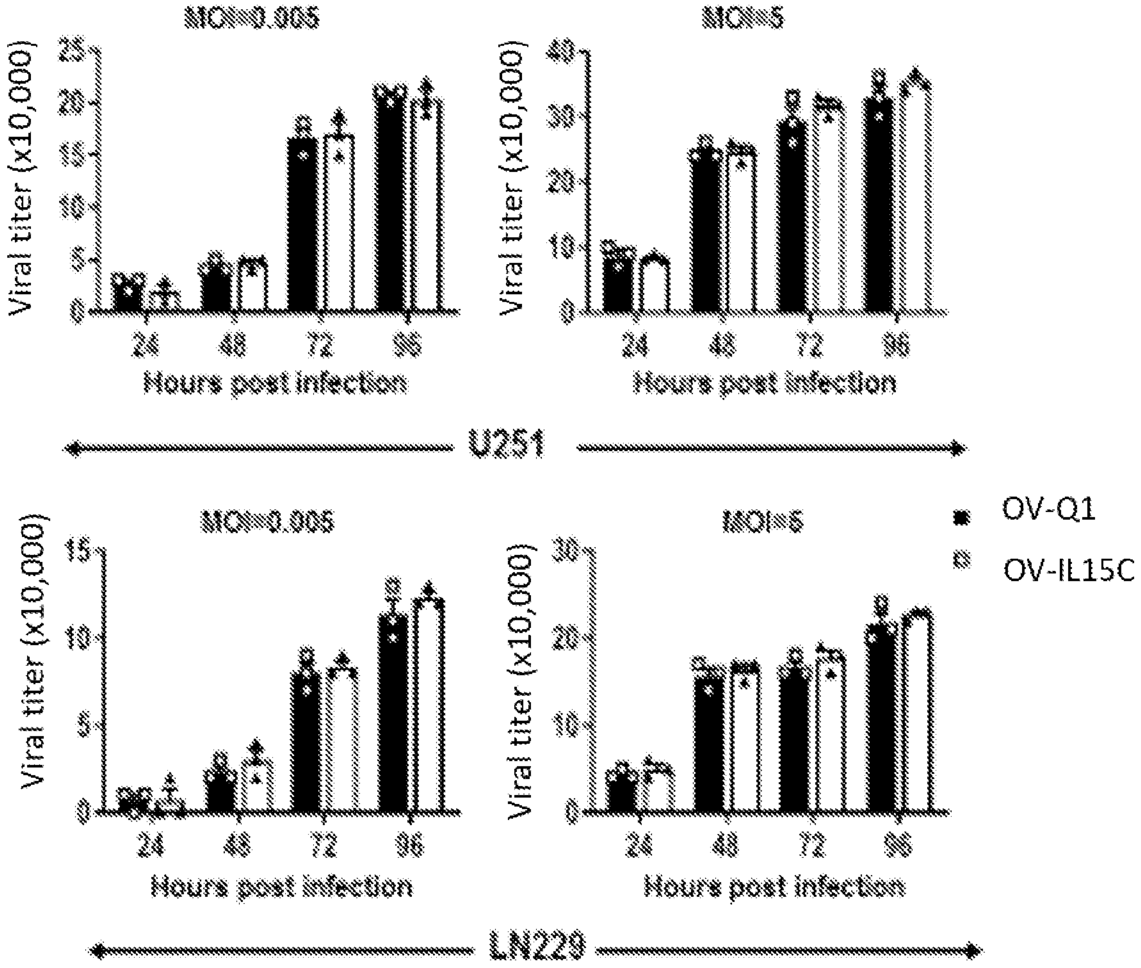

Described herein is an engineered oHSV, OV-IL15C, which expresses a fusion protein containing human IL-15 and an IL-15Rα sushi domain. The genetic maps of wild-type human HSV-1, parental oHSV control OV-Q1, and OV-IL15C are shown in FIG. 4A. Immunoblotting analysis showed the IL-15/IL-15Rα complex tagged with HA was the correct size of 32 kDa (FIG. 4B). ELISA results indicated that secretion of the IL-15/IL-15Rα complex occurred in a time-dependent manner with approximately 600 pg/ml, 300 pg/ml, 1,200 pg/ml and 1,000 pg/ml secreted by U251 cells, LN229 cells, 293T cells and CT2A cells, respectively, 96 h after OV-IL15C infection, while the IL-15/IL-15Rα complex was undetectable in uninfected and OV-Q1-infected cells (FIG. 4C). In order to investigate the capacity of viral production by OV-IL15C, the GBM cell lines were infected with the OVs at different MOIs. The OV-IL15C-infected U251 and LN229 cells produced a similar amount of virus compared to the same cells infected with the control OV-Q1 under either unsaturated or saturated conditions (FIG. 4D), suggesting OV-IL15C engineering does not affect the capacity for viral production.

Enhancement of NK and $CD8^+$ T cells cytotoxicity and survival by the secreted IL-15/IL-15Rα complex in vitro.

Figure 5A:
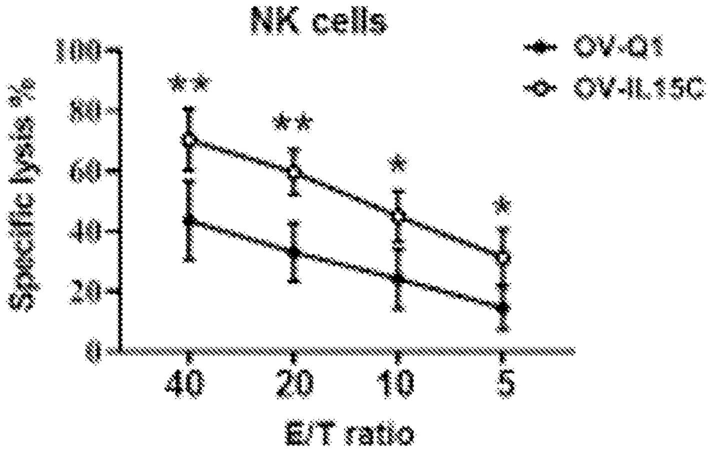
FIGS. 5A-5F illustrate IL-15/IL-15Rα complex secreted by OV-IL15C-infected GBM cells enhances cytotoxicity and improves survival of NK cells and CD8+ T cells in vitro.
Figure 5B:
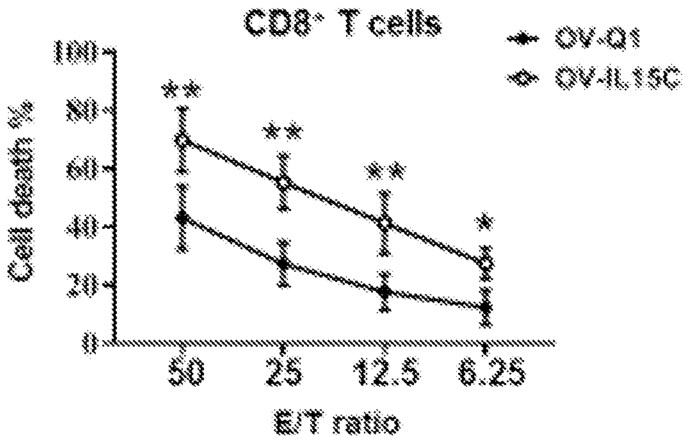
Figure 5C:
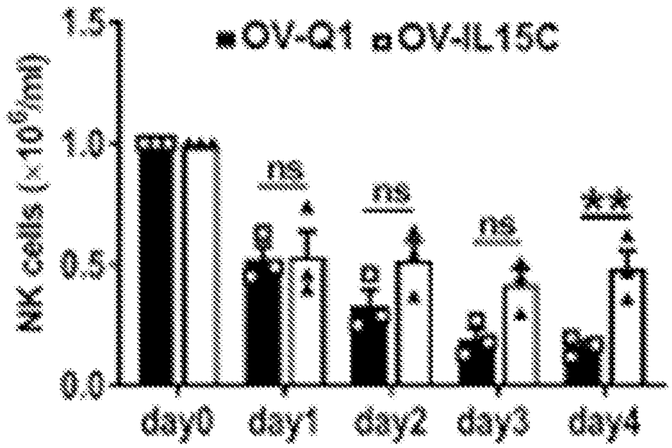
Figure 5D:
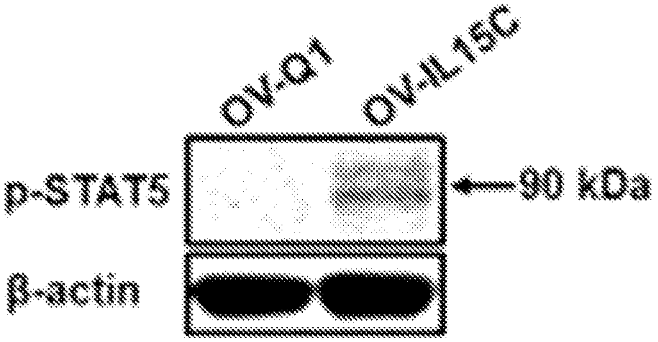
Figure 5E:
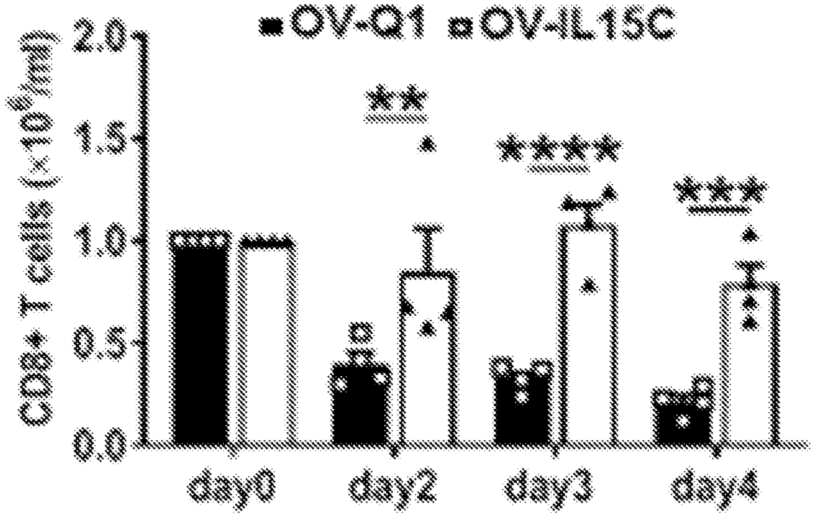
Figure 5F:
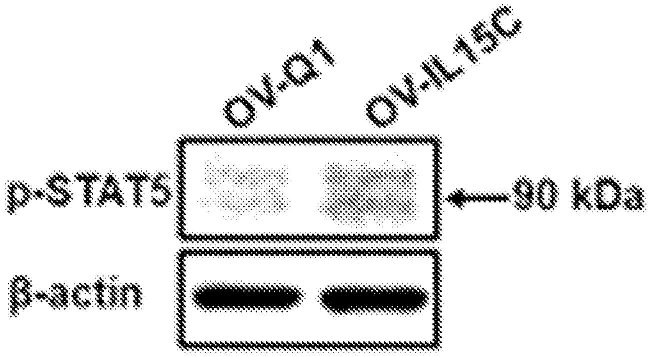

Both NK cells and $CD8^+$ T cells are cytolytic lymphocytes and their activation by cytokines are critical for their anti-tumor activities. NK cells cytotoxicity against GBM30 cells were found significantly increased in the presence of supernatants from OV-IL15C-infected GBM cells compared to supernatants from OV-Q1-infected GBM cells (FIG. 5A). Similarly, the killing ability of $CD8^+$ T cells against GBM30 cells also significantly increased in the presence of supernatants from OV-IL15C-infected GBM cells compared to supernatants from OV-Q1-infected GBM cells (FIG. 5B). Furthermore, the supernatants from OV-IL15C-infected GBM cells significantly prolonged the survival of NK and $CD8^+$ T cells compared to supernatants from OV-Q1-infected GBM cells, correlating to increased levels of phosphorylated STATS in both NK cells and $CD8^+$ T cells (FIGS. 5C-5F).

OV-IL15C Prolongs Survival and Enhances GBM Virotherapy In Vivo in a Xenograft Model.

Figure 6A:
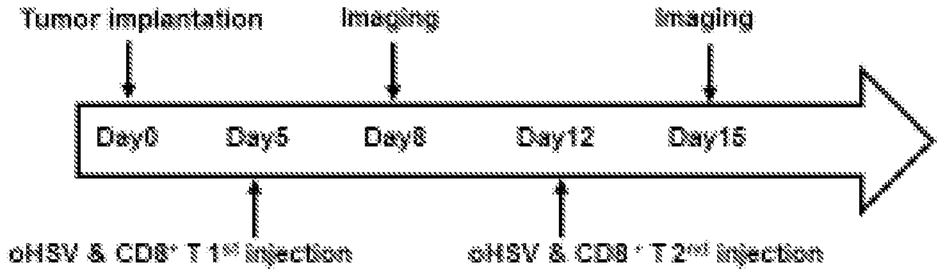
FIGS. 6A-6F illustrate enhancement of GBM virotherapy in vivo by OV-IL15C in a xenograft GBM mouse model.
Figure 6B:
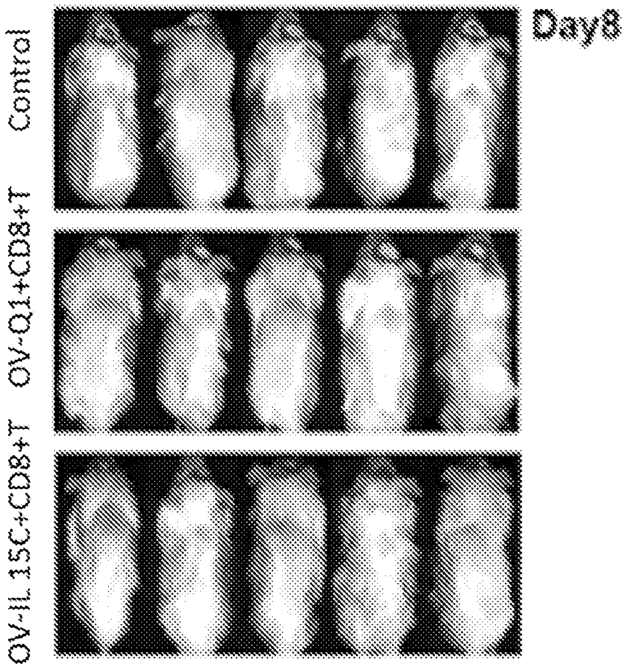
Figure 6C:
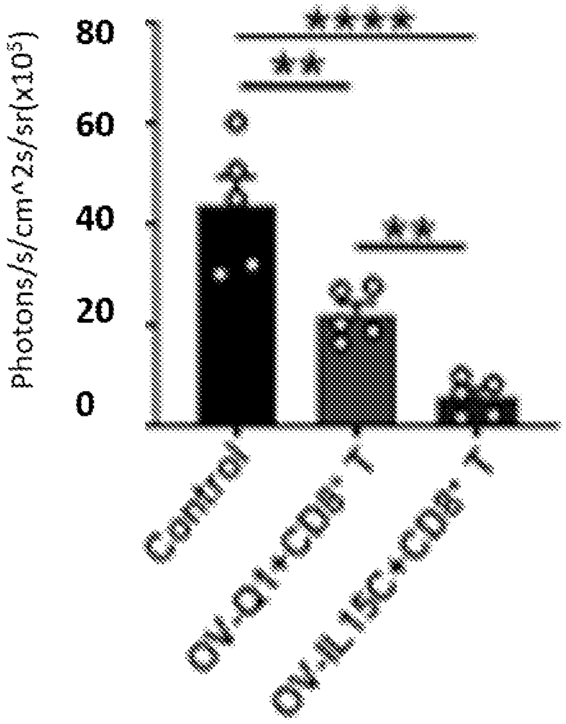
Figure 6D:
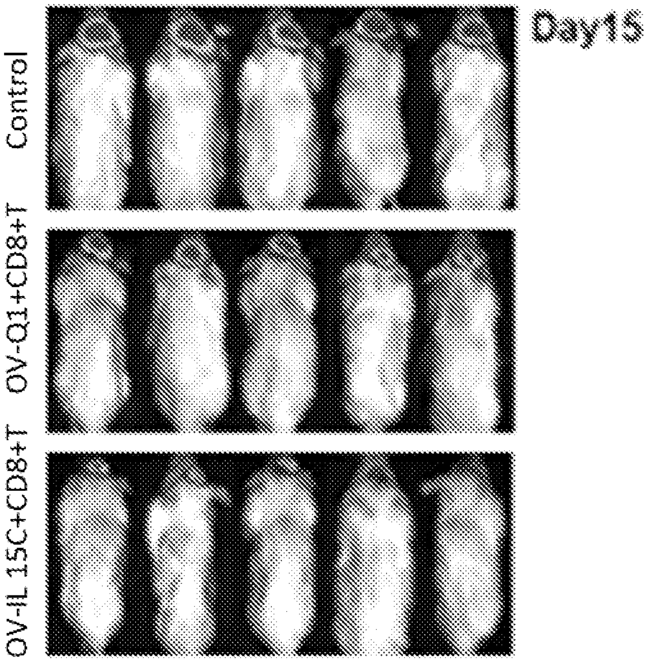
Figure 6E:
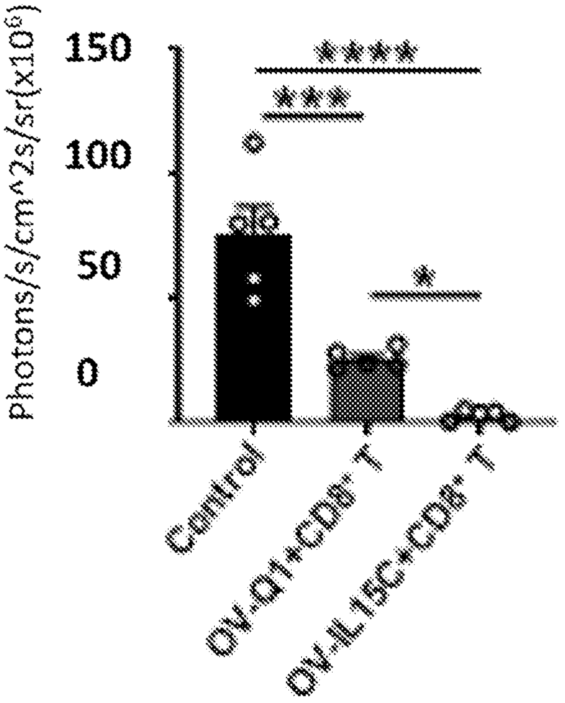
Figure 6F:
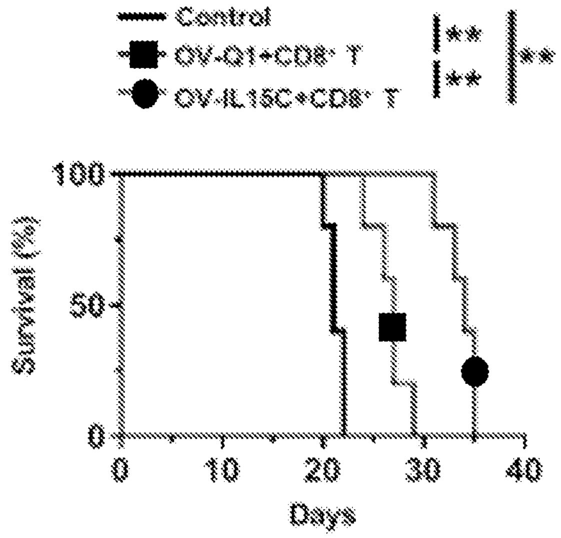

To evaluate the efficacy of OV-IL15C on GBM therapy in vivo, a xenograft GBM mouse model was established by intracranially injecting luciferase-expressing GBM30 cells into NSG mice (FIG. 6A). Five and 12 days after tumor implantation, mice received an intratumoral injection of OV-Q1 or OV-IL15C on each day, both of which were co-injected with $CD8^+$ T cells pre-activated by anti-CD3/anti-CD28 beads or saline, follow by serial in vivo imaging. Mice treated with OV-IL15C and $CD8^+$ T cells showed a significant reduction in tumor burden compared to mice treated with OV-Q1 and $CD8^+$ T cells, and survived significantly longer than all other groups (FIGS. 6B-6F). To validate the ability of OV-IL15C to enhance NK cells survival and cytotoxicity in vivo, a xenograft GBM model was established with intratumoral injection of OV-IL15C and primary human NK cells. However, there were no significant differences in tumor burden or survival between the OV-IL15C and OV-Q1 groups (FIGS. 11A-11D).

Improved Outcome of Off-the-Shelf EGFR-CAR NK Cells In Vitro and an In Vivo Xenograft Model.

Figure 7A:
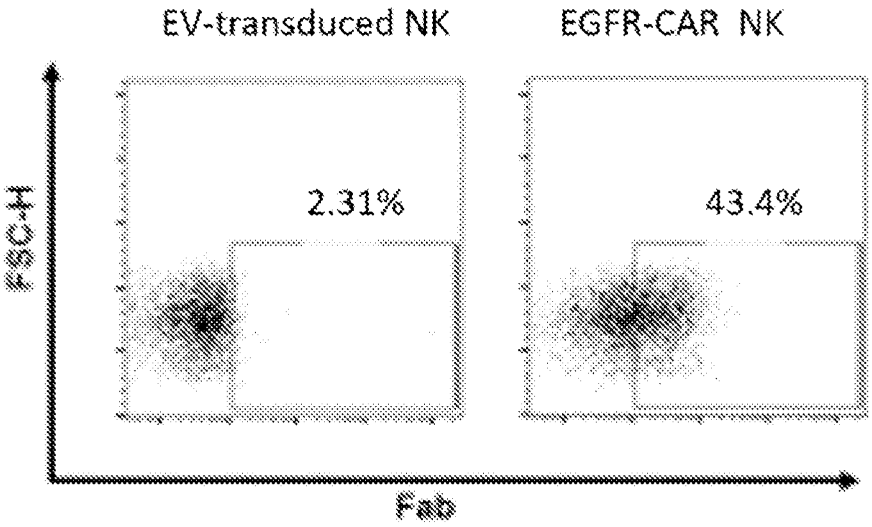
FIGS. 7A-7G illustrate EGFR-CAR NK cells enhance eradication of GBM cells and prolongs survival in an in vivo xenograft model.
Figure 7B:
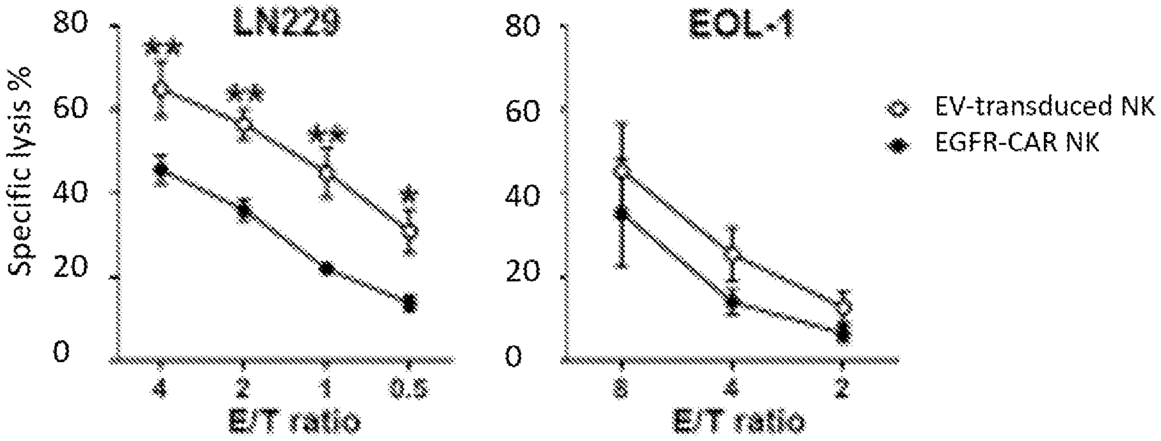
Figure 7C:
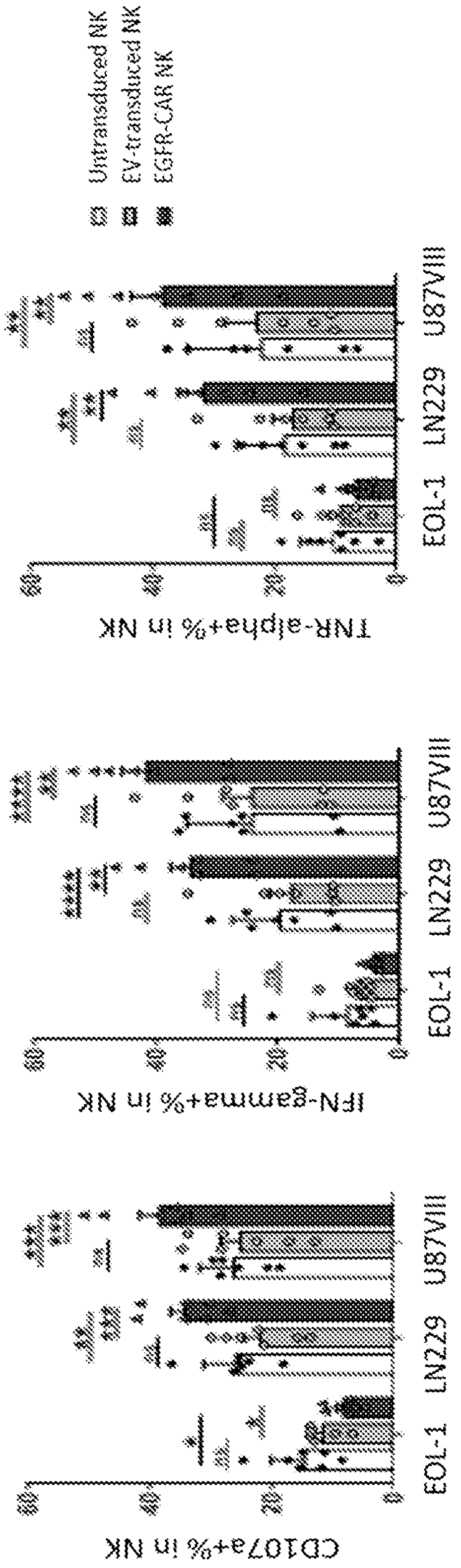
Figure 7D:
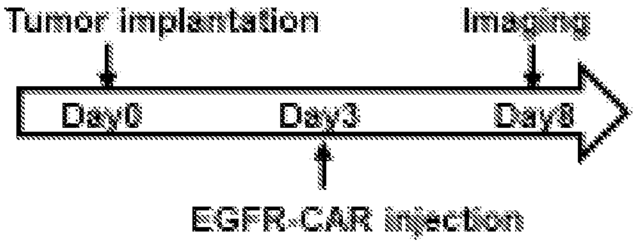
Figure 7E:
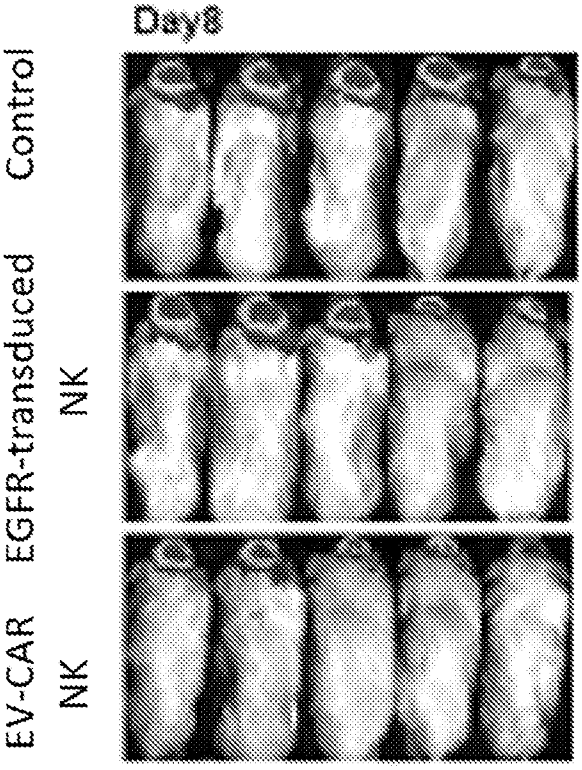
Figure 7F:
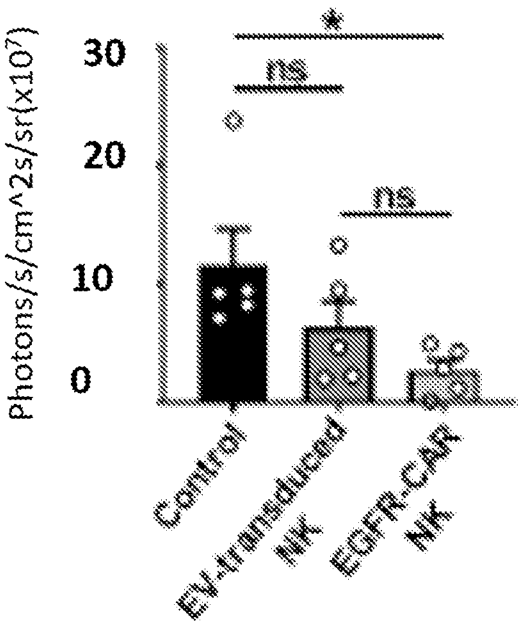
Figure 7G:
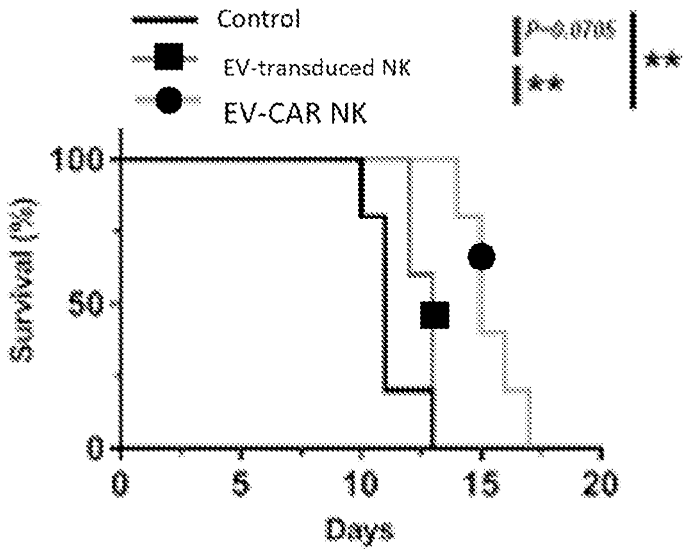

In order to improve NK cells anti-tumor activity in immunotherapy, CAR NK cells targeting wild-type EGFR and EGFRvIII GBM cells were generated. For this, human peripheral blood NK cells were transduced with an EGFR- CAR retroviral vector (FIG. 7A) followed by expansion. Over $1\times10^{11}$ EGFR-CAR NK cells were generated from peripheral blood of a single donor. Cells were frozen down and ready, so called off-the-shelf, for both in vitro and in vivo experiments after thawing. Cytotoxicity of EGFR-CAR NK cells against the EGFR+LN229 GBM cell line (19) or the $EGFR^-$ EOL-1 (20) cell line was assessed at different effector/target (E/T) ratios. Across all E/T ratios, EGFR-CAR NK cells exerted superior killing of LN229 cells compared to EV-transduced NK cells (FIG. 7B, left panel). The EGFR-CAR NK cells were equally efficient as EV-transduced NK cells in killing $EGFR^-$ EOL-1 target cells (FIG. 7B, right panel), indicating that the enhanced killing of $EGFR^+$ targets by the transduced cells is mediated by the CAR and unrelated to a non-specific enhancement in NK cells cytotoxicity. Furthermore, CD107a degranulation and IFN-γ and TNF-α secretion was measured in response to LN229, U87vIII (an $EGFRvIII^+$ cell line), and EOL-1 target cell lines, and all were significantly increased against CAR target cells compared to the EV-transduced NK cells, while the EGFR-CAR NK cells and EV-transduced NK cells showed similar effector function against the $EGFR^-$ EOL-1 cells (FIG. 7C). Next, the luciferase-expressing U87vIII orthotopic GBM model was established, results showed that EGFR-CAR NK cells showed better anti-GBM activity and improved survival of mice bearing GBM tumor compared to EV-transduced NK or control groups (FIGS. 7D-7G).

Combination of OV-IL15C and EGFR-CAR shows synergistic effects relative to corresponding monotherapies in a xenograft GBM model.

Figure 8A:
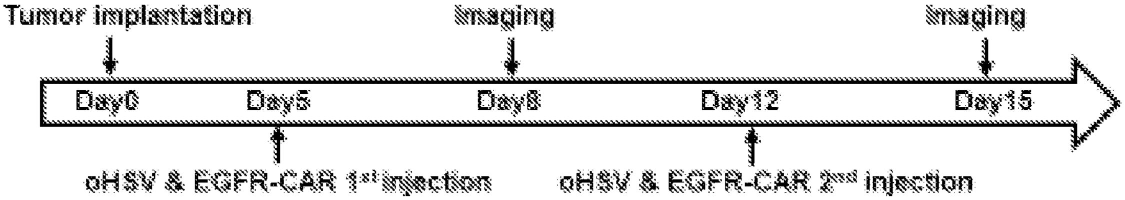
FIGS. 8A-8G demonstrate that the combination of OV-IL15C and EGFR-CAR NK cells show better effects than corresponding monotherapies in a xenograft GBM model.
Figure 8B:
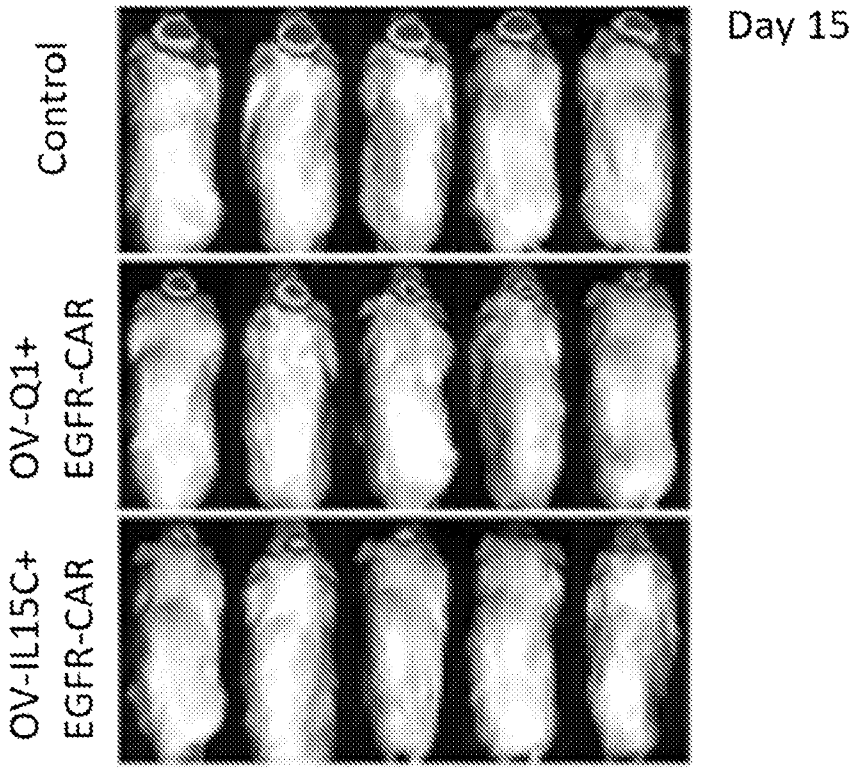
Figure 8C:
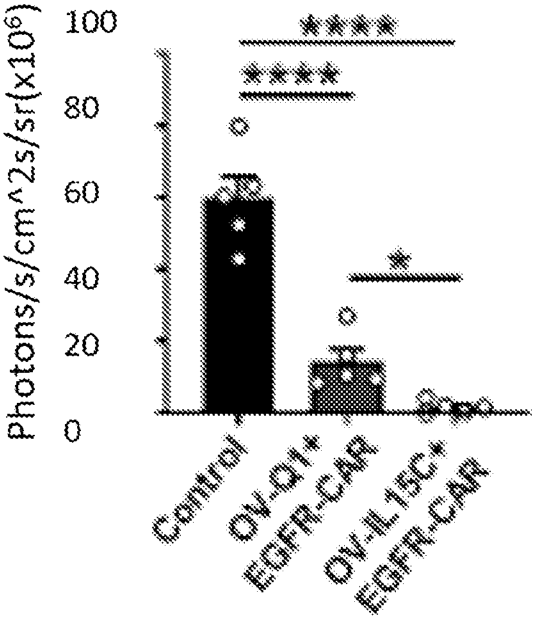
Figure 8D:
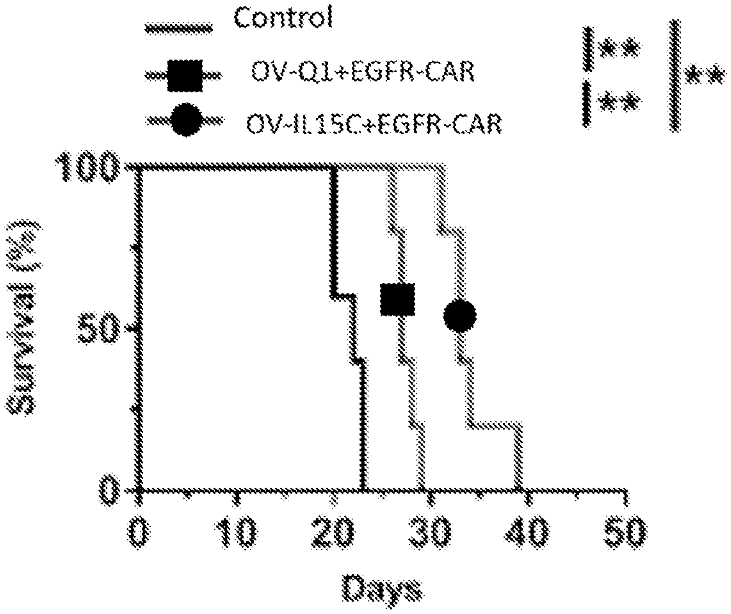
Figure 8E:
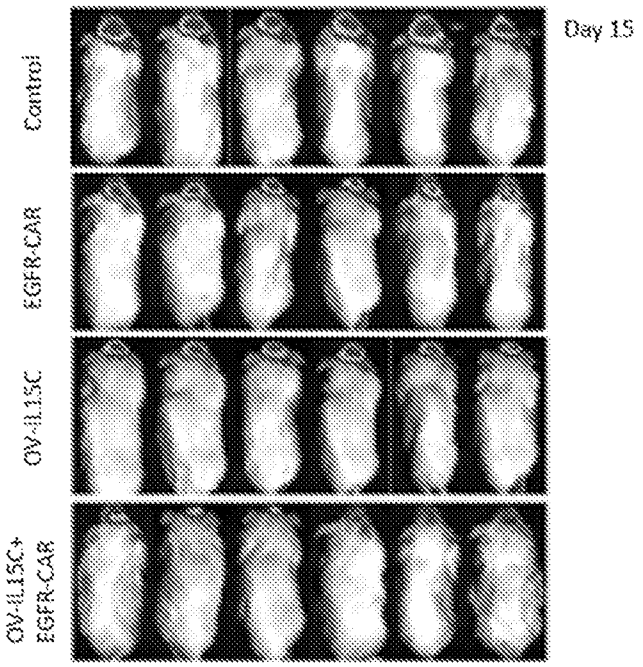
Figure 8F:
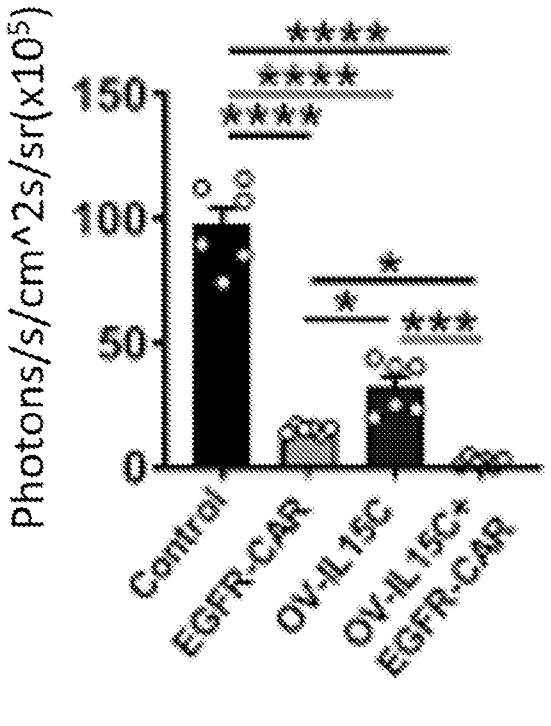
Figure 8G:
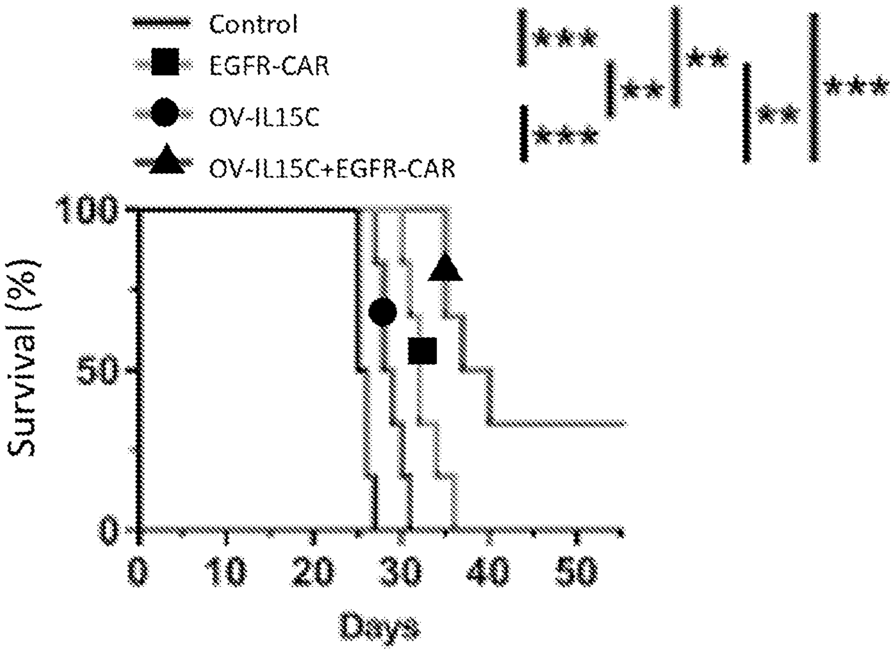
Figure 12:
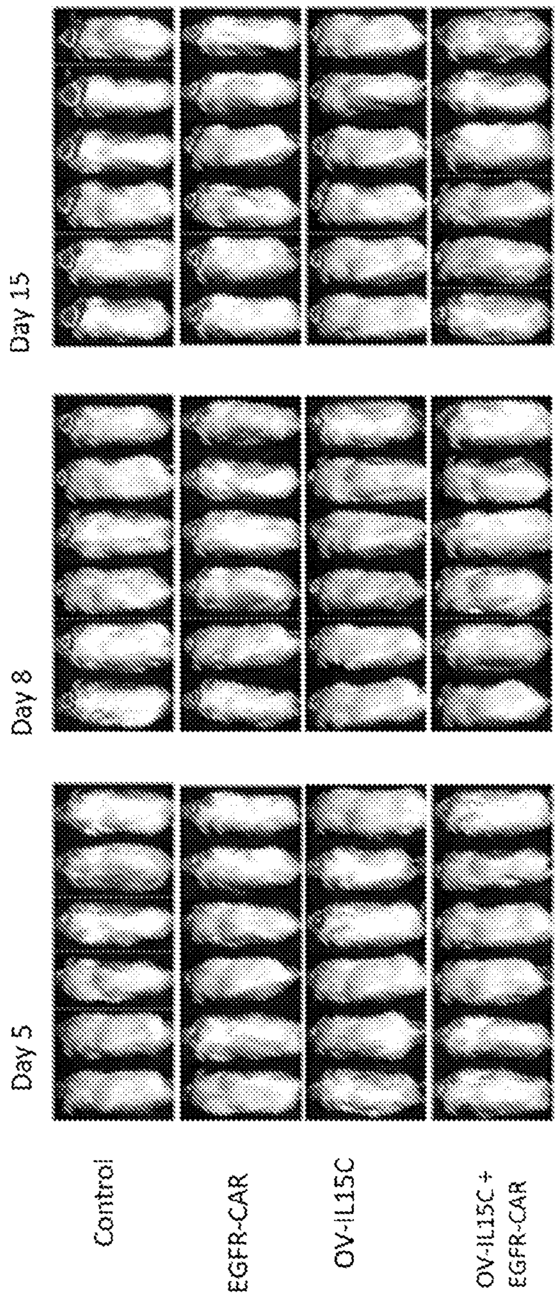
FIG. 12 is imaging data for the combination therapy of OV-IL15C and EGFR-CAR NK cells compared to each monotherapy in a xenograft GBM model.

The above results showed EGFR-CAR NK cells are superior to EV-transduced NK cells. The GBM30 xenograft model was used to test whether the combination of EGFR-CAR NK cells with OV-IL15C is superior to its combination with OV-Q1. Indeed, the combination of OV-IL15C and EGFR-CAR NK cells resulted in more significant reduction in tumor burden and prolonged survival compared to the combination of OV-Q1 and EGFR-CAR NK cells (FIGS. 8A-8D). These in vivo data provide a proof of concept for combination immunotherapy of OV with CAR NK cells. Next, OV-IL15C and EGFR-CAR was investigated for whether the combination shows a synergistic effect. The orthotopic GBM30 xenograft model was re-established and treatment timeline was shown in FIG. 8A. Luciferase-based in vivo imaging showed the mice that received either OV-IL15C alone, EGFR-CAR NK cells alone or combination of both had significantly reduced tumor growth compared to injection with saline control (FIG. 8E). Importantly, the suppression of tumor growth showed a synergistic effect after treatment with combination of OV-IL15C and EGFR-CAR NK cells compared to each monotherapy (FIG. 8F). The combination of two regimens also rendered mice to survive significantly longer than those in all other groups (FIG. 8G). Consistent data from in vivo imaging analysis on tumor at days 5, 8, and 15 for all the four groups are shown in FIG. 12.

OV-IL15C increases NK and T cells infiltration and improves GBM therapy in immunocompetent models in the presence or absence of EGFR-CAR NK cells.

Figure 9A:
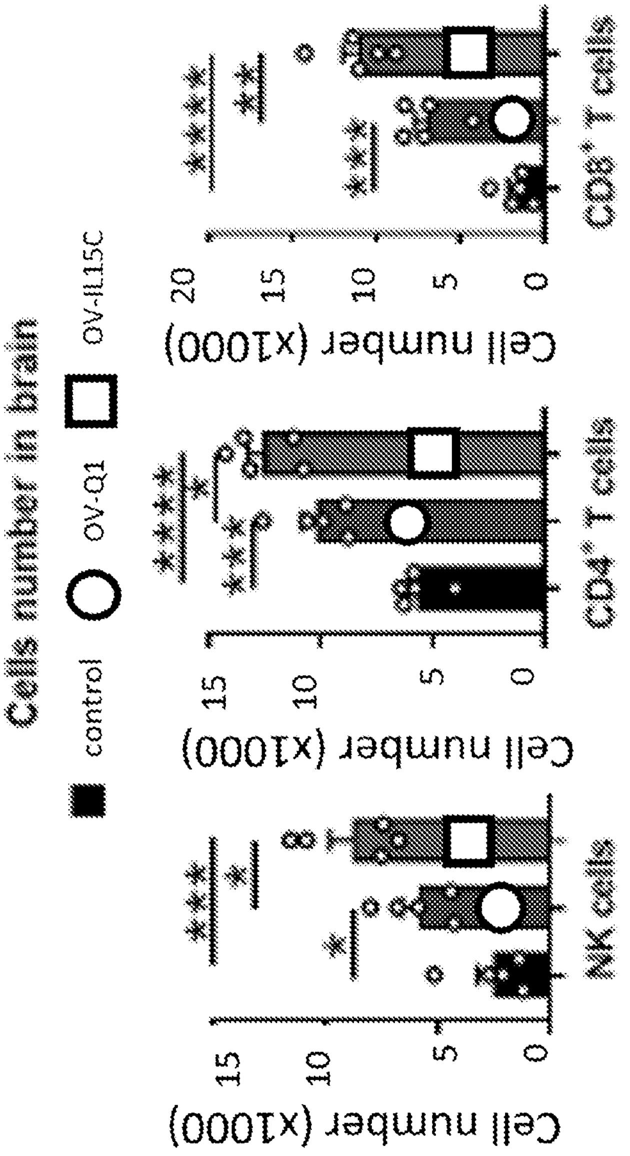
FIGS. 9A-9D illustrate that OV-IL15C enhances in vivo intracranial NK and T cell infiltration and prolongs survival in an immunocompetent GBM model.
Figure 9B:
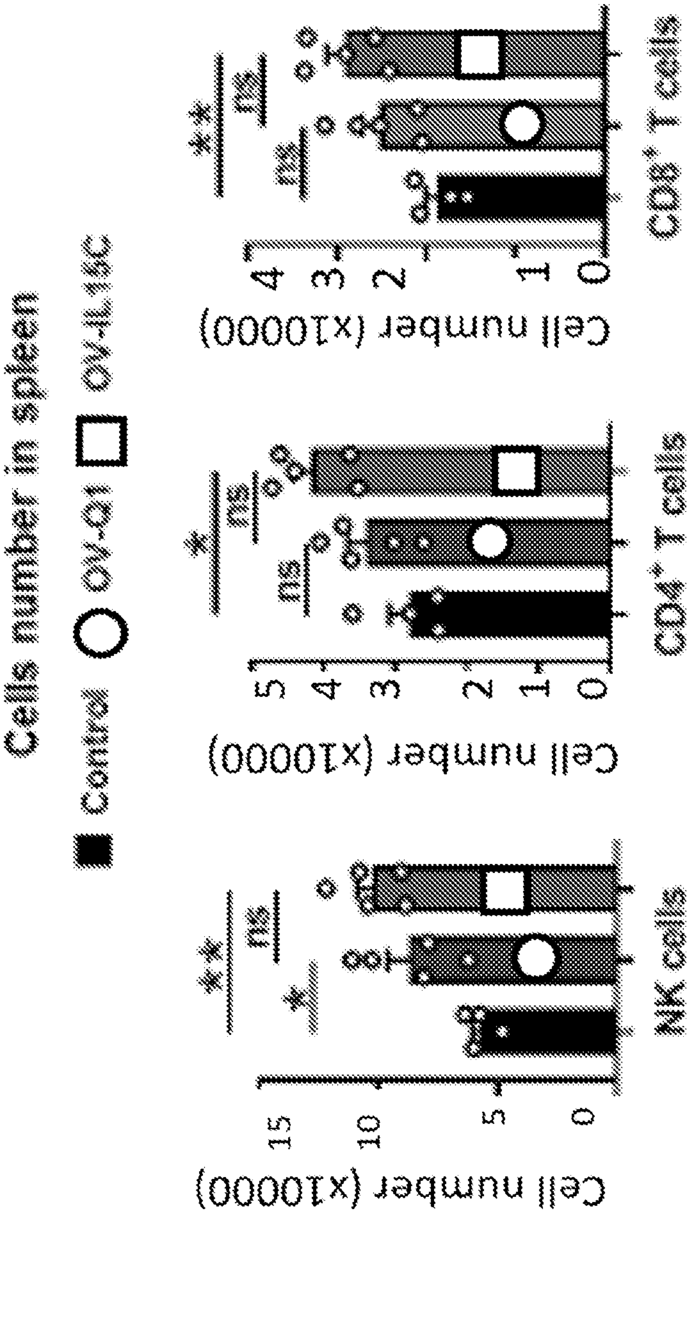
Figure 9C:
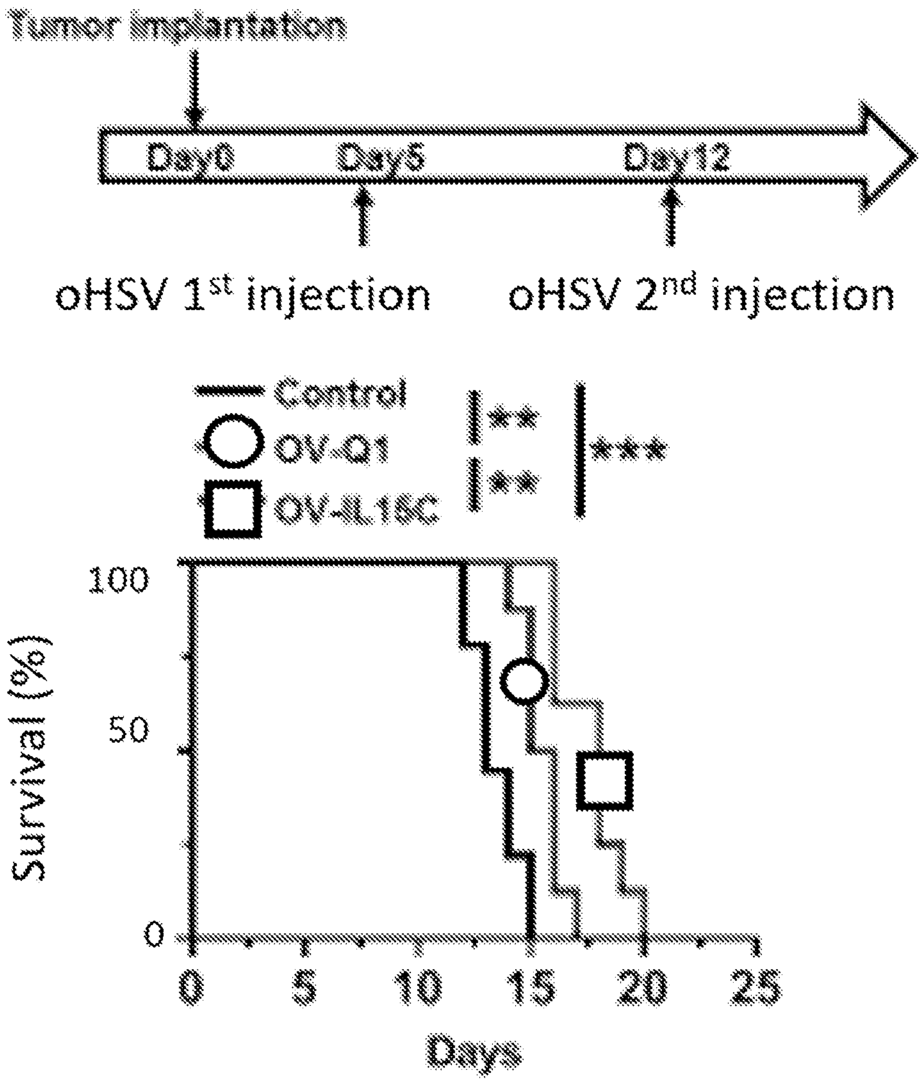
Figure 9D:
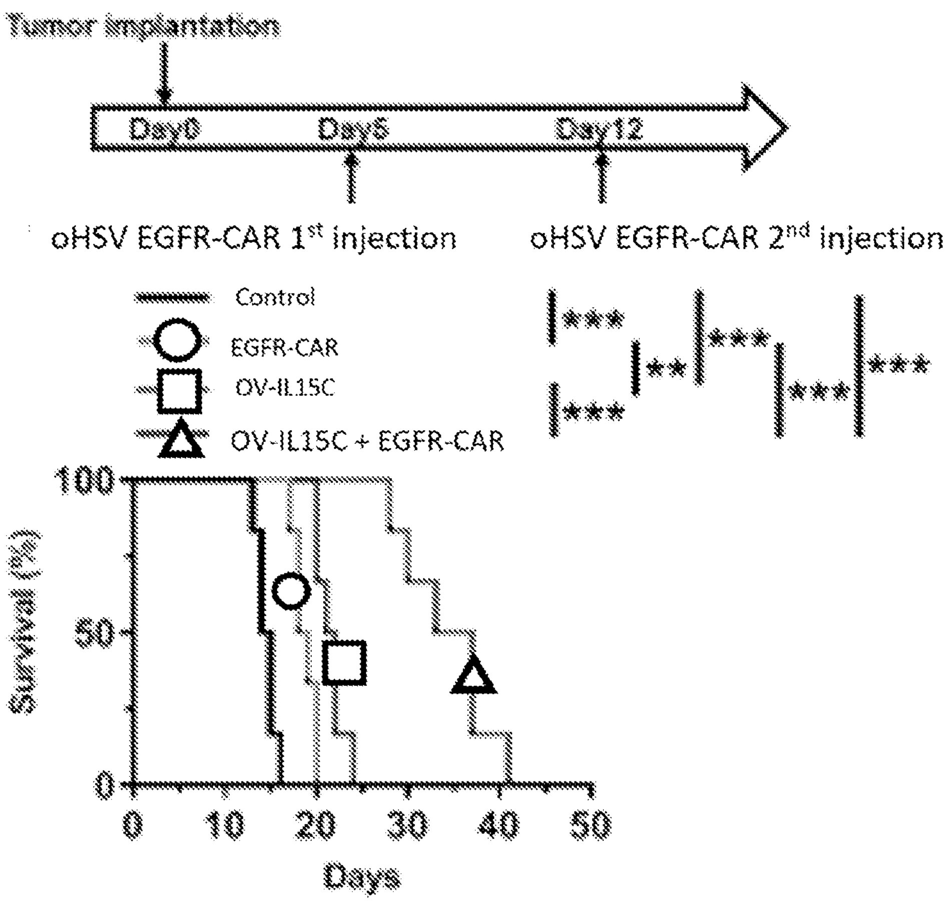
Figure 10A:
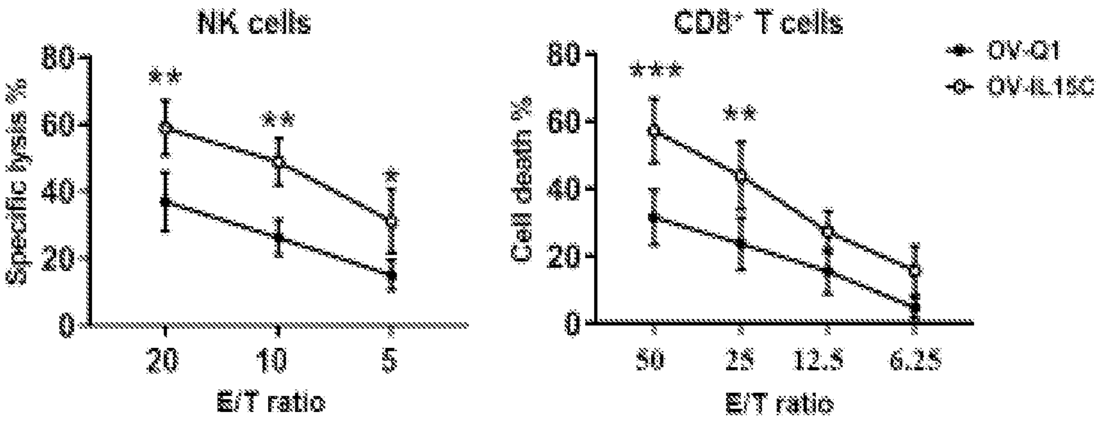
FIGS. 10A and 10B demonstrate that IL15C produced by OV-IL15C-infected GBM cells enhances cytotoxicity of NK and $CD8^+$ T as well as proliferation of $CD8^+$ T cells in vitro.
Figure 10B:
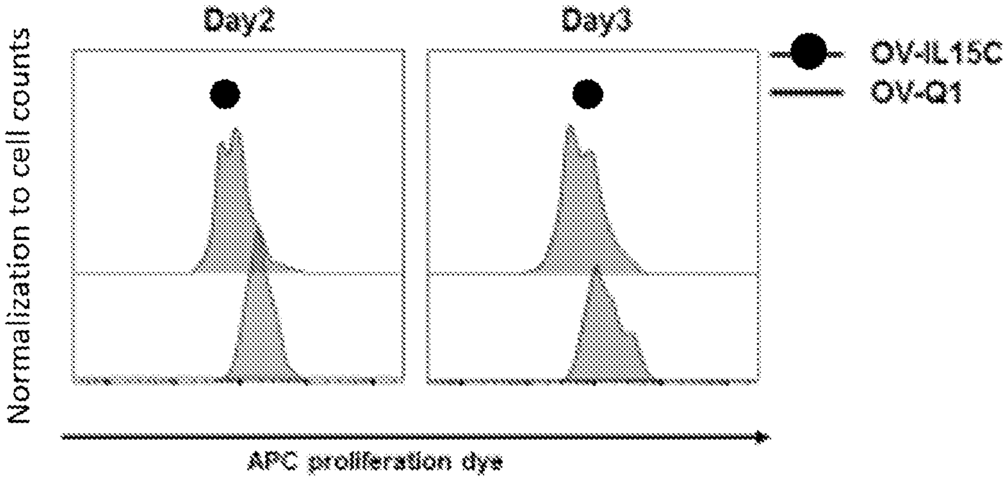
Figure 11A:
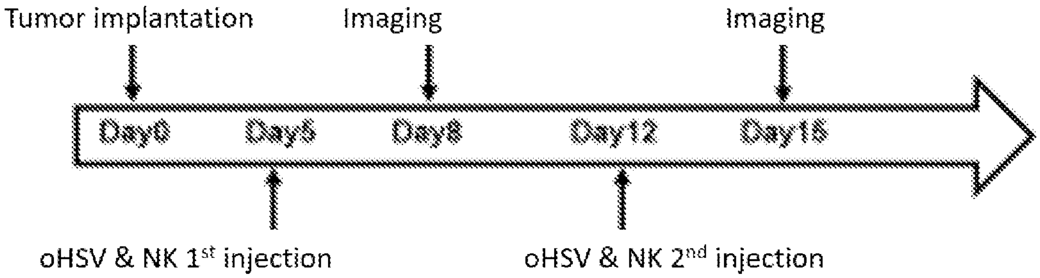
FIGS. 11A-11D show that there is negligible benefit of combination therapy with OV-IL15C and primary human NK cells in a xenograft GBM model.
Figure 11B:
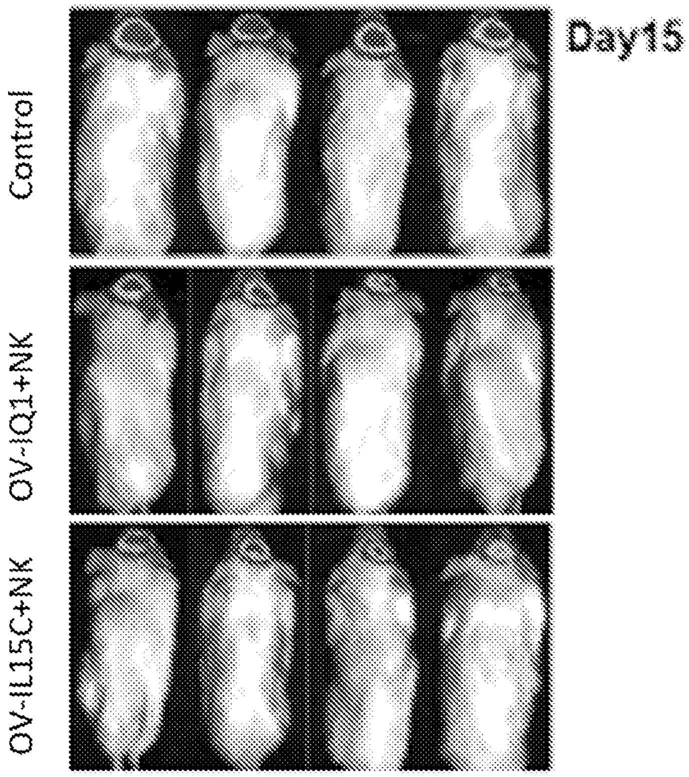
Figure 11C:
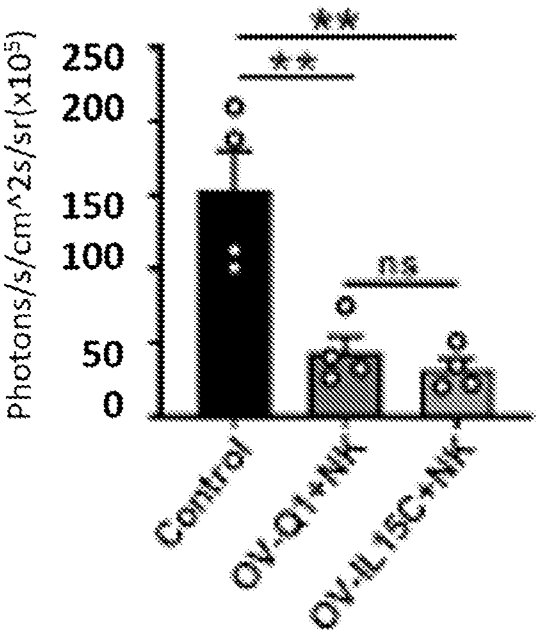
Figure 11D:
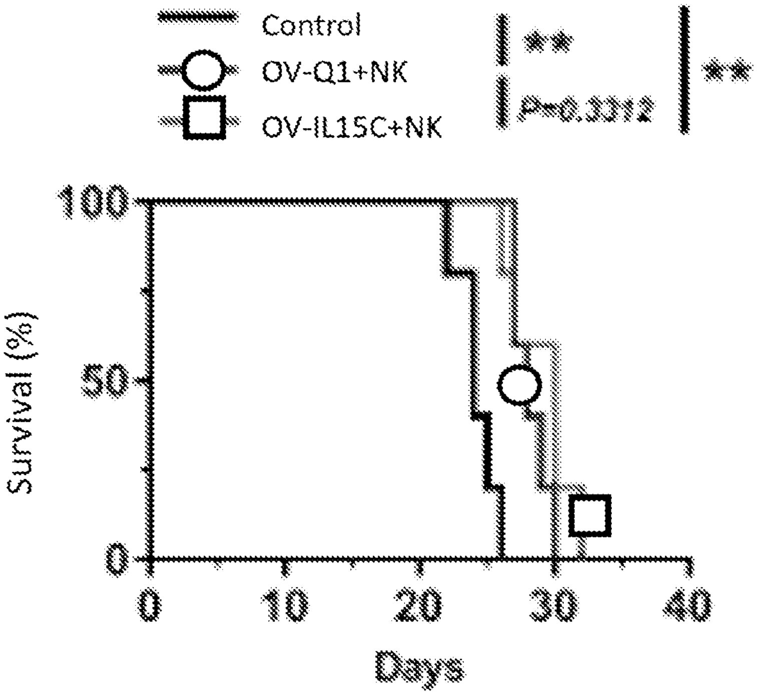

To study whether the use of OV-IL15C in GBM correlates with an improved immune response in the tumor microenvironment when compared to OV-Q1, the murine GBM cell line CT2A was intracranially injected into immunocompetent wild-type C57BL/6 mice to establish a GBM immunocompetent mouse model. CT2A-implanted GBM mice were randomly grouped and intratumorally treated with OV-Q1, OV-IL15C, or saline control. Three days after treatment, mice were euthanized to collect brain and splenic tissues. Results showed that OV-IL15C treatment recruited significantly more NK and both $CD4^+$ and $CD8^+$ T cells compared to OV-Q1 and saline treatment in the brain but not significantly more when compared to OV-Q1 treatment in the spleen (FIGS. 9A and 9B). Results further showed that OV-IL15C treatment significantly prolonged survival in the immunocompetent syngeneic mouse model when compared to the OV-Q1 or saline control groups (FIG. 9C). Based on the survival benefit of combining OV-IL15C with human EGFR-CAR NK cells in the xenograft model shown in FIGS. 8E-8G, the murine GBM cell line CT2A was engineered to overexpress human EGFR (named CT2A-hEGFR) and established the immunocompetent model following the schedule shown in FIG. 9D, up panel, then intratumorally treated with saline, OV-IL15C alone, human EGFR-CAR NK cells alone, or the combination OV-IL15C and human EGFR-CAR NK cells. The combination treatment also significantly prolonged mouse survival compared to the other groups (FIG. 9D).

Safe Profiling of OV-IL15C Both In Vitro and In Vivo.

Figure 13B:
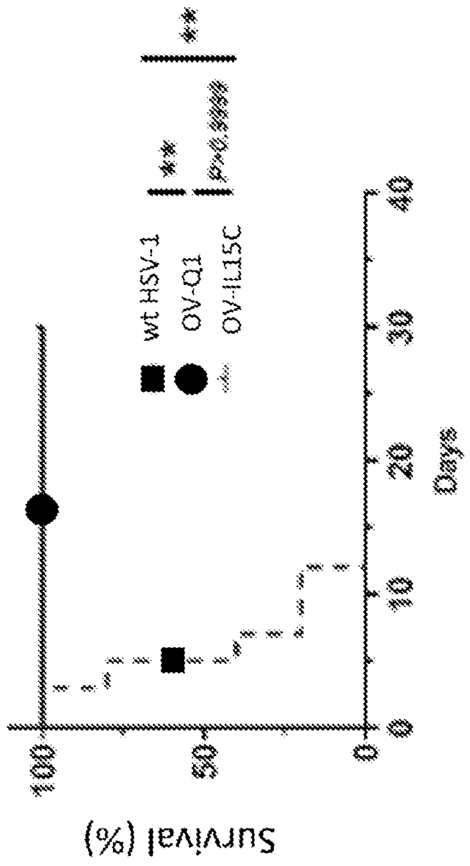
FIGS. 13A and 13B show results from the safety test of OV-IL15C in vitro and in vivo.
Figure 13A:
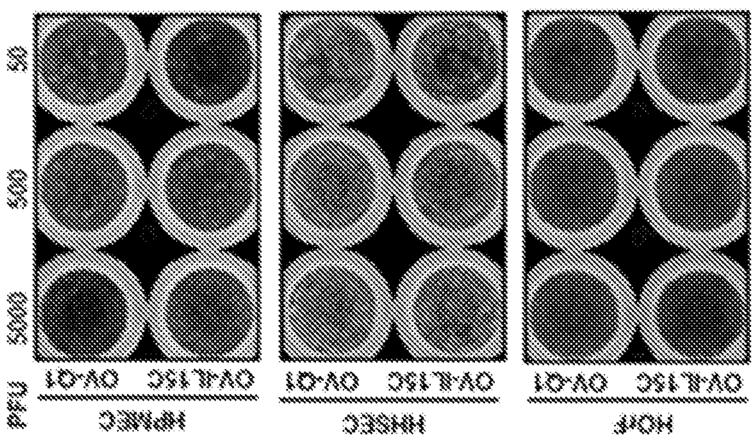

To evaluate the safety profile of OV-IL15C, an in vitro tropism change assay and an in vivo safety assay were established. No discernible change in tropism was observed following an infection with either OV-Q1 or OV-IL15C in primary human oral fibroblasts, primary human pulmonary microvascular endothelial cells, and or primary human hepatic sinusoidal endothelial cells (FIG. 13A). To assess in vivo safety, BALB/c mice were intracranially injected with wild-type HSV-1 (as a negative control for safety), OV-Q1, or OV-IL15C at a high dose of $1\times10^6$ pfu. Mice injected with wild-type HSV-1 died rapidly (less than 12 d), while all mice treated with OV-Q1 or OV-IL15C survived for several weeks (FIG. 13B).

Discussion

GBM is the most common and aggressive primary malignant brain tumor in humans and remains without curative therapy in its advanced stages (21). OV is a good approach to treat GBM as its local administration can induce immune infiltration and activation as well as direct lysis of GBM cells (22). OV can also serve as a cargo for local delivery of anti-GBM arsenals. Therefore, an OV expressing IL-15/IL-15Rα (OV-IL15C) was engineered to further improve anti-GBM immune responses. Among OVs, oHSV has been approved by the U.S. FDA for cancer treatment and is the furthest along in the clinic (23). As the cytokine is released locally, it can avoid systemic inflammation and produces strong locoregional anti-tumor immunity (24). The OV-IL15C engineered for this study is based on HSV-1, and studies demonstrated that it secretes a human IL-15/IL-15Rα complex and is safe in a BALB/c model in vivo. Accordingly, the complex secreted from OV-IL15C-infected GBM cells could prolong survival and activate both NK and $CD8^+$ T cells in vitro. Consistent with this, the combination therapy of OV-IL15C with $CD8^+$ T cells or EGFR-CAR NK cells significantly improves the therapeutic outcome in the xenograft and/or immunocompetent GBM mouse models in vivo.

IL-15 is an essential cytokine for NK cells and $CD8^+$ T cells development and function (25). Applicant originally discovered that this cytokine is critical in regulating NK cells survival (26). IL-15 complexed with its high affinity receptor alpha (IL-15Rα) has showed promising advantages over IL-15 alone (27). This may occur because the complex can significantly enhance the half-life and bioavailability of IL-15, thereby maximizing the activity of IL-15 in vivo (28-30). IL-15/IL-15Rα complex has a prolonged half-life time in serum (~20 hours) compared to IL-15 (~1 hour) (31-33). This might be more critical in the brain, as historically the brain was recognized as an immune-privileged site (34). Some in vivo mouse models found that IL-15/IL-15Rα complex could cause a rapid and significant regression of glioblastoma and melanoma, however, IL-15 alone could not (35, 36). Based on such advantages, engineered cells expressing IL-15/IL-15Rα complex for preclinical and clinical studies have been explored (9). Transfection of tumor cells with IL-15/IL-15Rα displays a high-level surface expression and improves NK cells as well as $CD8^+$ T cells-mediated tumor cells lysis (37). Tumor cells transferred to express IL-15/IL-15Rα could be used as a vaccine to provide a long-term protection compared to non-transfected tumor cells (38). Furthermore, $CD8^+$ T cells or dendritic cells (DC) transfected with IL-15/IL-15Rα could also enhance the anti-tumor response in vivo (39, 40). However, using an oHSV to express human IL-15/IL-15Rα and the study of how it alone or its combination with another effective therapy modulates the immune response in the tumor microenvironment and the subsequent therapeutic efficacy have not been explored.

$CD8^+$ T cells play an important role in regulating the anti-tumor immune response. Results show that the IL-15/IL-15Rα complex secreted by OV-IL15C-infected GBM cells significantly enhances $CD8^+$ T cells cytotoxicity and survival in vitro. An in vivo xenograft GBM model also showed a better therapeutic outcome of OV-IL15C plus $CD8^+$ T cells compared to OV-Q1 plus $CD8^+$ T cells. However, effector cytotoxic T lymphocytes (CTLs) eliminate tumor cells mainly by recognizing tumor-associated antigens presented on major histocompatibility complex class (MHC) through their expressed T cell receptors (TCR), triggering strong T cell activation. However, T cell responses belong to the adaptive immune response which needs time to ready. In contrast, NK cells belong to the innate immune response and can quickly respond to target cells including tumor cells without prior activation. In vitro, the IL-15/IL-15Rα complex secreted by OV-IL15C-infected GBM cells enhances anti-GBM activity of both $CD8^+$ T cells and NK cells, while in vivo Applicant only observed improved survival by OV-IL15C when combined with $CD8^+$ T cells instead of NK cells. One reason to explain these results may be due to the fact primary human NK cells have limited survival period and/or effector function, especially when they are not armed with a CAR targeting a tumor-associated antigen.

Engineering NK cells with a CAR to effectively treat cancer is necessary, as previously shown in several cancer models including GBM (41-43). A recent clinical phase 1 and 2 trial administered anti-CD19 CAR NK cells to successfully target CD19 positive lymphoid malignancies such as non-Hodgkin's lymphoma and chronic lymphocytic leukemia (18). However, using NK cells to treat patients with solid tumors remains very limited, in large part due to the inability of NK cells to traffic into tumor tissue as well as the immunosuppressive microenvironment of the tumor. Previous studies demonstrated the efficacy and safety of an intracranial injection of EGFR-CAR modified NK-92 cells in a GBM orthotopic xenograft model (44). However, NK-92 cells were derived from a lymphoma cell line and it should be irradiated before their infusion into patients and the irradiation may cause the loss of some anti-tumor activity (45). Primary CAR NK cells could have several advantages for clinical applications as reviewed elsewhere (46). In the current study described herein, primary human NK cells were obtained from peripheral blood mononuclear cells (PBMCs) to engineer EGFR-CAR NK cells. Results show EGFR-CAR NK cells derived from peripheral blood and manufactured with expansion by an autologous PBMC condition successfully recognize the EGFR antigen on GBM cells and lead to enhanced anti-GBM activity both in vitro and in vivo. Applicant was able to generate up to $1\times10^{11}$ frozen and ready to use, so called off-the-shelf EGFR-CAR products under good laboratory practices-like conditions for all in vitro and in vivo studies.

NK cells are good to make "off-the-shelf" CAR cell products with no need to wait to treat patients. Off-the-shelf CARs are made from cells from healthy volunteers and should be more effective than a product that is generated from cancer patients who may not have an ideal minimum number of functional T or NK cells to start with. Another benefit of an off-the-shelf CAR is the opportunity to scale up, thus a single healthy volunteer can generate enough cells to treat multiple patients. In clinical trials, one of the off-the-shelf CAR T-cell products is UCART19 that targets CD19 with encouraging results (47). The first-in-man, dose-escalation phase 1 UCART19 in Advanced Lymphoid Malignancies (CALM) trial is the first study of an off-the-shelf product in adult patients with relapsed adult B-cell ALL. The Pediatric Acute Lymphoblastic Leukemia (PALL) trial is evaluating UCART19 in pediatric patients with acute lymphoblastic leukemia. In contrast to T cells, primary NK cells are more difficult to isolate, purify, and transduce. Therefore, it is more challenging to generate off-the-shelf CAR NK products. However, NK cells possess a better advantage to generate "off-the-shelf" CAR cells compared to T cells, as further engineering to remove TCR is required for generating "off-the-shelf" CAR products for T cells, while the modification is not required for NK cells. A recent study has demonstrated induced pluripotent stem cell (iPSCs) could offer a safe and renewable source of NK cells that may be standardized as an off-the-shelf therapy (48). Another study demonstrate UCB has a very good potential to generate off-the-shelf CAR NK cells (18). Both CART and CAR NK cell therapies have similar issues in treating solid tumors, such as heterogeneous tumor populations, off-target tumor effects and the immunosuppressive tumor microenvironment. Combination with OVs armed with cytokines improve their function.

GBM is a very heterogenous cancer. Even in a same individual patient, some tumor cells express wild-type EGFR, some express EGFRvIII, some express both genes, and some do not express either (49). EGFR-CAR NK cells directly target EGFR and EGFRvIII positive tumor cells, while OVs have selectivity for tumor cells vs normal cells and can therefore kill tumor cells lacking EGFR and EGFRvIII expression. EGFR-CAR NK cells and OVs both can launch endogenous immune responses to tumor cells (50-54). As noted above in the tumor models described herein, OV may not be very effective as a single agent, yet combination therapies of OV with chemotherapy such as rapamycin (55, 56) or temozolomide (TMZ) (57, 58), or combinations with immune checkpoint inhibitors such as anti-PD-L1 (59) and anti-CTLA-4 (60), or with a CAR therapy (61, 62) may improve oncolytic virotherapy. The combination of chemotherapy and OV leads to a higher response rate due to increased tumor cell death and enhanced entry of virus into the chemotherapy-exposed tumor cells compared to the use of OV alone (63). OV infection stimulates anti-tumor immune responses and transforms a "cold" tumor microenvironment with few immune effector cells into a "hot" tumor microenvironment with increased immune cells (64). In addition, CAR-modified NK cells may quickly destroy the tumor tissue structure, generate permissible space, and thus likely increase the permeability of virus distribution and replication in cancer cells when combined with OV.

REFERENCES FOR EXAMPLES 1-3

1. Martuza, R. L., Malick, A., Markert, J. M., Ruffner, K. L. & Coen, D. M. Experimental therapy of human glioma by means of a genetically engineered virus mutant. *Science* (New York, N.Y.) 252, 854-856 (1991).
2. Todo, T. et al. Systemic antitumor immunity in experimental brain tumor therapy using a multimutated, replication-competent herpes simplex virus. *Human gene therapy* 10, 2741-2755 (1999).
3. Xu, B. et al. An oncolytic herpesvirus expressing E-cadherin improves survival in mouse models of glioblastoma. *Nature biotechnology* (2018).
4. Xia, Z. J. et al. [Phase III randomized clinical trial of intratumoral injection of E1B gene-deleted adenovirus (H101) combined with cisplatin-based chemotherapy in treating squamous cell cancer of head and neck or esophagus]. *Ai Zheng* 23, 1666-1670 (2004).
5. Kiyokawa, J. & Wakimoto, H. Preclinical And Clinical Development Of Oncolytic Adenovirus For The Treatment Of Malignant Glioma. *Oncolytic Virother* 8, 27-37 (2019).
6. Jiang, H., Gomez-Manzano, C., Lang, F. F., Alemany, R. & Fueyo, J. Oncolytic adenovirus: preclinical and clinical studies in patients with human malignant gliomas. *Curr. Gene Ther.* 9, 422-427 (2009).
7. Kuruppu, D. & Tanabe, K. K. HSV-1 as a novel therapy for breast cancer meningeal metastases. *Cancer gene therapy* 22, 506-508 (2015).
8. Garber, K. China approves world's first oncolytic virus therapy for cancer treatment. *Journal of the National Cancer Institute* 98, 298-300 (2006).
9. Coffin, R. Interview with Robert Coffin, inventor of T-VEC: the first oncolytic immunotherapy approved for the treatment of cancer. *Immunotherapy* 8, 103-106 (2016).
10. Andtbacka, R. H. et al. Talimogene Laherparepvec Improves Durable Response Rate in Patients With Advanced Melanoma. *Journal of clinical oncology: official journal of the American Society of Clinical Oncology* 33, 2780-2788 (2015).
11. Todo, T., Martuza, R. L., Rabkin, S. D. & Johnson, P. A. Oncolytic herpes simplex virus vector with enhanced MHC class I presentation and tumor cell killing. *Proceedings of the National Academy of Sciences of the United States of America* 98, 6396-6401 (2001).
12. Kim, D. H. & Thorne, S. H. Targeted and armed oncolytic poxviruses: a novel multi-mechanistic therapeutic class for cancer. *Nature reviews. Cancer* 9, 64-71 (2009).
13. Kim, J. H. et al. Systemic armed oncolytic and immunologic therapy for cancer with JX-594, a targeted poxvirus expressing GM-CSF. *Molecular therapy: the journal of the American Society of Gene Therapy* 14, 361-370 (2006).
14. Parato, K. A. et al. The oncolytic poxvirus JX-594 selectively replicates in and destroys cancer cells driven by genetic pathways commonly activated in cancers. *Molecular therapy: the journal of the American Society of Gene Therapy* 20, 749-758 (2012).
15. Park, B. H. et al. Use of a targeted oncolytic poxvirus, JX-594, in patients with refractory primary or metastatic liver cancer: a phase I trial. *The Lancet. Oncology* 9, 533-542 (2008).
16. Breitbach, C. J. et al. Intravenous delivery of a multi-mechanistic cancer-targeted oncolytic poxvirus in humans. *Nature* 477, 99-102 (2011).
17. Heo, J. et al. Randomized dose-finding clinical trial of oncolytic immunotherapeutic vaccinia JX-594 in liver cancer. *Nature medicine* 19, 329-336 (2013).
18. Ramesh, N. et al. CG0070, a conditionally replicating granulocyte macrophage colony-stimulating factor—armed oncolytic adenovirus for the treatment of bladder cancer. *Clinical cancer research: an official journal of the American Association for Cancer Research* 12, 305-313 (2006).
19. Burke, J. M. et al. A first in human phase 1 study of CG0070, a GM-CSF expressing oncolytic adenovirus, for the treatment of nonmuscle invasive bladder cancer. *The Journal of urology* 188, 2391-2397 (2012).
20. Zhan, Y., Lew, A. M. & Chopin, M. The Pleiotropic Effects of the GM-CSF Rheostat on Myeloid Cell Differentiation and Function: More Than a Numbers Game. *Frontiers in immunology* 10, 2679 (2019).
21. Grivennikov, S. et al. IL-6 and Stat3 are required for survival of intestinal epithelial cells and development of colitis-associated cancer. *Cancer cell* 15, 103-113 (2009).
22. Bradford, E. M. et al. Epithelial TNF Receptor Signaling Promotes Mucosal Repair in Inflammatory Bowel Disease. *Journal of immunology* (Baltimore, Md.: 1950) 199, 1886-1897 (2017).
23. Geng, H. et al. In Inflamed Intestinal Tissues and Epithelial Cells, Interleukin 22 Signaling Increases Expression of H19 Long Noncoding RNA, Which Promotes Mucosal Regeneration. *Gastroenterology* 155, 144-155 (2018).
24. Grabstein, K. H. et al. Cloning of a T cell growth factor that interacts with the beta chain of the interleukin-2 receptor. *Science* (New York, N.Y.) 264, 965-968 (1994).
25. Waldmann, T. A. & Tagaya, Y. The multifaceted regulation of interleukin-15 expression and the role of this cytokine in NK cell differentiation and host response to intracellular pathogens. *Annual review of immunology* 17, 19-49 (1999).
26. Carson, W. E. et al. Interleukin (IL) 15 is a novel cytokine that activates human natural killer cells via components of the IL-2 receptor. *The Journal of experimental medicine* 180, 1395-1403 (1994).
27. Jakobisiak, M., Golab, J. & Lasek, W. Interleukin 15 as a promising candidate for tumor immunotherapy. *Cytokine & growth factor reviews* 22, 99-108 (2011).
28. Dubois, S., Mariner, J., Waldmann, T. A. & Tagaya, Y. IL-15Ralpha recycles and presents IL-15 In trans to neighboring cells. *Immunity* 17, 537-547 (2002).
29. Burkett, P. R. et al. Coordinate expression and trans presentation of interleukin (IL)-15Ralpha and IL-15 supports natural killer cell and memory CD8+ T cell homeostasis. *The Journal of experimental medicine* 200, 825-834 (2004).
30. Mortier, E. et al. Macrophage- and dendritic-cell-derived interleukin-15 receptor alpha supports homeostasis of distinct CD8+ T cell subsets. *Immunity* 31, 811-822 (2009).
31. Wu, Z. et al. The IL-15 receptor {alpha} chain cytoplasmic domain is critical for normal IL-15Ralpha function but is not required for trans-presentation. *Blood* 112, 4411-4419 (2008).

32. Anderson, D. M. et al. Functional characterization of the human interleukin-15 receptor alpha chain and close linkage of IL15RA and IL2RA genes. *The Journal of biological chemistry* 270, 29862-29869 (1995).
33. Dubois, S. et al. Natural splicing of exon 2 of human interleukin-15 receptor alpha-chain mRNA results in a shortened form with a distinct pattern of expression. *The Journal of biological chemistry* 274, 26978-26984 (1999).
34. Kobayashi, H. et al. Role of trans-cellular IL-15 presentation in the activation of NK cell-mediated killing, which leads to enhanced tumor immunosurveillance. *Blood* 105, 721-727 (2005).
35. Morris, J. C. et al. Vaccination with tumor cells expressing IL-15 and IL-15Ralpha inhibits murine breast and prostate cancer. *Gene therapy* 21, 393-401 (2014).
36. Guo, Y., Luan, L., Patil, N. K. & Sherwood, E. R. Immunobiology of the IL-15/IL-15Ralpha complex as an antitumor and antiviral agent. *Cytokine & growth factor reviews* 38, 10-21 (2017).
37. Han, J. et al. TGFbeta Treatment Enhances Glioblastoma Virotherapy by Inhibiting the Innate Immune Response. *Cancer research* 75, 5273-5282 (2015).
38. Klebanoff, C. A. et al. IL-15 enhances the in vivo antitumor activity of tumor-reactive CD8+ T cells. *Proceedings of the National Academy of Sciences of the United States of America* 101, 1969-1974 (2004).
39. Yu, P. et al. Simultaneous inhibition of two regulatory T-cell subsets enhanced Interleukin-15 efficacy in a prostate tumor model. *Proceedings of the National Academy of Sciences of the United States of America* 109, 6187-6192 (2012).
40. Yu, P., Bamford, R. N. & Waldmann, T. A. IL-15-dependent CD8+CD122+ T cells ameliorate experimental autoimmune encephalomyelitis by modulating IL-17 production by CD4+ T cells. *European journal of immunology* 44, 3330-3341 (2014).
41. Becker, T. C. et al. Interleukin 15 is required for proliferative renewal of virus-specific memory CD8 T cells. *The Journal of experimental medicine* 195, 1541-1548 (2002).
42. Bergamaschi, C. et al. Secretion and biological activity of short signal peptide IL-15 is chaperoned by IL-15 receptor alpha in vivo. *Journal of immunology* (Baltimore, Md.: 1950) 183, 3064-3072 (2009).
43. Stonier, S. W., Ma, L. J., Castillo, E. F. & Schluns, K. S. Dendritic cells drive memory CD8 T-cell homeostasis via IL-15 transpresentation. *Blood* 112, 4546-4554 (2008).

REFERENCES FOR EXAMPLE 4

1. T. Todo et al., Systemic antitumor immunity in experimental brain tumor therapy using a multimutated, replication-competent herpes simplex virus. *Hum Gene Ther* 10, 2741-2755 (1999).
2. H. Rehman, A. W. Silk, M. P. Kane, H. L. Kaufman, Into the clinic: Talimogene laherparepvec (T-VEC), a first-in-class intratumoral oncolytic viral therapy. *Journal for ImmunoTherapy of Cancer* 4, 53 (2016).
3. T. A. Waldmann, Y. Tagaya, The multifaceted regulation of interleukin-15 expression and the role of this cytokine in NK cell differentiation and host response to intracellular pathogens. *Annu Rev Immunol* 17, 19-49 (1999).
4. S. Dubois, J. Mariner, T. A. Waldmann, Y. Tagaya, IL-15Ralpha recycles and presents IL-15 In trans to neighboring cells. *Immunity* 17, 537-547 (2002).
5. J. M. J. Van den Bergh, E. Lion, V. F. I. Van Tendeloo, E. L. J. M. Smits, IL-15 receptor alpha as the magic wand to boost the success of IL-15 antitumor therapies: The upswing of IL-15 transpresentation. *Pharmacology & Therapeutics* 170, 73-79 (2017).
6. J. Wu, IL-15 Agonists: The Cancer Cure Cytokine. *J Mol Genet Med* 7, 85 (2013).
7. H. Kobayashi et al., Role of trans-cellular IL-15 presentation in the activation of NK cell-mediated killing, which leads to enhanced tumor immunosurveillance. *Blood* 105, 721-727 (2005).
8. J. C. Morris et al., Vaccination with tumor cells expressing IL-15 and IL-15Ralpha inhibits murine breast and prostate cancer. *Gene Ther* 21, 393-401 (2014).
9. Y. Guo, L. Luan, N. K. Patil, E. R. Sherwood, Immunobiology of the IL-15/IL-15Ralpha complex as an antitumor and antiviral agent. *Cytokine Growth Factor Rev* 38, 10-21 (2017).
10. S. Spencer et al., Loss of the interleukin-6 receptor causes immunodeficiency, atopy, and abnormal inflammatory responses. *J Exp Med* 216, 1986-1998 (2019).
11. Y. Zhan, A. M. Lew, M. Chopin, The Pleiotropic Effects of the GM-CSF Rheostat on Myeloid Cell Differentiation and Function: More Than a Numbers Game. *Front Immunol* 10, 2679 (2019).
12. E. M. Bradford et al., Epithelial TNF Receptor Signaling Promotes Mucosal Repair in Inflammatory Bowel Disease. *J Immunol* 199, 1886-1897 (2017).
13. H. Geng et al., In Inflamed Intestinal Tissues and Epithelial Cells, Interleukin 22 Signaling Increases Expression of H19 Long Noncoding RNA, Which Promotes Mucosal Regeneration. *Gastroenterology* 155, 144-155 (2018).
14. A. Karnowski et al., B and T cells collaborate in antiviral responses via IL-6, IL-21, and transcriptional activator and coactivator, Oct2 and OBF-1. *J Exp Med* 209, 2049-2064 (2012).
15. M. Sadelain, R. Brentjens, I. Rivière, The Basic Principles of Chimeric Antigen Receptor Design. *Cancer Discovery* 3, 388-398 (2013).
16. C. E. Brown et al., Regression of Glioblastoma after Chimeric Antigen Receptor T-Cell Therapy. *N Engl J Med* 375, 2561-2569 (2016).
17. D. M. O'Rourke et al., A single dose of peripherally infused EGFRvIII-directed CAR T cells mediates antigen loss and induces adaptive resistance in patients with recurrent glioblastoma. *Science Translational Medicine* 9, eaaa0984 (2017).
18. E. Liu et al., Use of CAR-Transduced Natural Killer Cells in CD19-Positive Lymphoid Tumors. *N Engl J Med* 382, 545-553 (2020).
19. J. A. J. M. van de Water et al., Therapeutic stem cells expressing variants of EGFR-specific nanobodies have antitumor effects. *Proceedings of the National Academy of Sciences* 109, 16642-16647 (2012).
20. H. Mahmud et al., Epidermal growth factor receptor is expressed and active in a subset of acute myeloid leukemia. *J Hematol Oncol* 9, 64-64 (2016).
21. D. N. Louis et al., The 2016 World Health Organization Classification of Tumors of the Central Nervous System: a summary. *Acta Neuropathol* 131, 803-820 (2016).
22. G. Wollmann, K. Ozduman, A. N. van den Pol, Oncolytic virus therapy for glioblastoma multiforme: concepts and candidates. *Cancer J*18, 69-81 (2012).

23. P. K. Bommareddy, A. Patel, S. Hossain, H. L. Kaufman, Talimogene Laherparepvec (T-VEC) and Other Oncolytic Viruses for the Treatment of Melanoma. *Am J Clin Dermatol* 18, 1-15 (2017).

24. T. M. Pearl, J. M. Markert, K. A. Cassady, M. G. Ghonime, Oncolytic Virus-Based Cytokine Expression to Improve Immune Activity in Brain and Solid Tumors. *Molecular Therapy—Oncolytics* 13, 14-21 (2019).

25. N. D. Huntington et al., IL-15 trans-presentation promotes human NK cell development and differentiation in vivo. *J Exp Med* 206, 25-34 (2009).

26. W. E. Carson et al., A potential role for interleukin-15 in the regulation of human natural killer cell survival. *J Clin Invest* 99, 937-943 (1997).

27. E. Mortier et al., Soluble interleukin-15 receptor alpha (IL-15R alpha)-sushi as a selective and potent agonist of IL-15 action through IL-15R beta/gamma. Hyperagonist IL-15×IL-15R alpha fusion proteins. *J Biol Chem* 281, 1612-1619 (2006).

28. J. M. Van den Bergh, E. Lion, V. F. Van Tendeloo, E. L. Smits, IL-15 receptor alpha as the magic wand to boost the success of IL-15 antitumor therapies: The upswing of IL-15 transpresentation. *Pharmacol Ther* 170, 73-79 (2017).

29. T. A. Stoklasek, K. S. Schluns, L. Lefrancois, Combined IL-15/IL-15Ralpha immunotherapy maximizes IL-15 activity in vivo. *J Immunol* 177, 6072-6080 (2006).

30. M. Epardaud et al., Interleukin-15/Interleukin-15Rα Complexes Promote Destruction of Established Tumors by Reviving Tumor-Resident CD8<sup>+</sup> T Cells. *Cancer Research* 68, 2972-2983 (2008).

31. M. P. Rubinstein et al., Converting IL-15 to a superagonist by binding to soluble IL-15R{alpha}. *Proc Natl Acad Sci USA* 103, 9166-9171 (2006).

32. T. A. Stoklasek, K. S. Schluns, L. Lefrancois, Combined IL-15/IL-15Ralpha immunotherapy maximizes IL-15 activity in vivo. *J Immunol* 177, 6072-6080 (2006).

33. A. I. Kokaji, D. L. Hockley, K. P. Kane, IL-15 transpresentation augments CD8+ T cell activation and is required for optimal recall responses by central memory CD8+ T cells. *J Immunol* 180, 4391-4401 (2008).

34. M. J. Carson, J. M. Doose, B. Melchior, C. D. Schmid, C. C. Ploix, CNS immune privilege: hiding in plain sight. *Immunol Rev* 213, 48-65 (2006).

35. D. C. Gaston et al., Production of bioactive soluble interleukin-15 in complex with interleukin-15 receptor alpha from a conditionally-replicating oncolytic HSV-1. *PLoS One* 8, e81768 (2013).

36. M. Epardaud et al., Interleukin-15/interleukin-15R alpha complexes promote destruction of established tumors by reviving tumor-resident CD8+ T cells. *Cancer Res* 68, 2972-2983 (2008).

37. J. Rowley, A. Monie, C. F. Hung, T. C. Wu, Inhibition of tumor growth by NK1.1+ cells and CD8+ T cells activated by IL-15 through receptor beta/common gamma signaling in trans. *J Immunol* 181, 8237-8247 (2008).

38. J. C. Morris et al., Vaccination with tumor cells expressing IL-15 and IL-15Rα inhibits murine breast and prostate cancer. *Gene Ther* 21, 393-401 (2014).

39. J. Rowley, A. Monie, C. F. Hung, T. C. Wu, Expression of IL-15RA or an IL-15/IL-15RA fusion on CD8+ T cells modifies adoptively transferred T-cell function in cis. *Eur J Immunol* 39, 491-506 (2009).

40. J. C. Steel et al., Interleukin-15 and its receptor augment dendritic cell vaccination against the neu oncogene through the induction of antibodies partially independent of CD4 help. *Cancer Res* 70, 1072-1081 (2010).

41. X. Chen et al., A combinational therapy of EGFR-CAR NK cells and oncolytic herpes simplex virus 1 for breast cancer brain metastases. *Oncotarget* 10.18632/oncotarget.8526 (2016).

42. J. Chu et al., CS1-specific chimeric antigen receptor (CAR)-engineered natural killer cells enhance in vitro and in vivo antitumor activity against human multiple myeloma. *Leukemia* 28, 917-927 (2014).

43. J. Han et al., CAR-Engineered NK Cells Targeting Wild-Type EGFR and EGFRvIII Enhance Killing of Glioblastoma and Patient-Derived Glioblastoma Stem Cells. *Sci Rep* 5, 11483 (2015).

44. J. Han et al., CAR-Engineered NK Cells Targeting Wild-Type EGFR and EGFRvIII Enhance Killing of Glioblastoma and Patient-Derived Glioblastoma Stem Cells. *Sci Rep* 5, 11483 (2015).

45. X. Tang et al., First-in-man clinical trial of CAR NK-92 cells: safety test of CD33-CAR NK-92 cells in patients with relapsed and refractory acute myeloid leukemia. *Am J Cancer Res* 8, 1083-1089 (2018).

46. Y. Hu, Z.-G. Tian, C. Zhang, Chimeric antigen receptor (CAR)-transduced natural killer cells in tumor immunotherapy. *Acta Pharmacol Sin* 39, 167-176 (2018).

47. R. Benjamin et al., Preliminary Data on Safety, Cellular Kinetics and Anti-Leukemic Activity of UCART19, an Allogeneic Anti-CD19 CAR T-Cell Product, in a Pool of Adult and Pediatric Patients with High-Risk CD19+ Relapsed/Refractory B-Cell Acute Lymphoblastic Leukemia. *Blood* 132, 896-896 (2018).

48. Y. Li, D. L. Hermanson, B. S. Moriarity, D. S. Kaufman, Human iPSC-Derived Natural Killer Cells Engineered with Chimeric Antigen Receptors Enhance Anti-tumor Activity. *Cell Stem Cell* 23, 181-192.e185 (2018).

49. Q. W. Fan et al., EGFR phosphorylates tumor-derived EGFRvIII driving STAT3/5 and progression in glioblastoma. *Cancer Cell* 24, 438-449 (2013).

50. C. Zhang et al., Chimeric Antigen Receptor-Engineered NK-92 Cells: An Off-the-Shelf Cellular Therapeutic for Targeted Elimination of Cancer Cells and Induction of Protective Antitumor Immunity. *Frontiers in immunology* 8, 533-533 (2017).

51. M. C. Burger et al., CAR-Engineered NK Cells for the Treatment of Glioblastoma: Turning Innate Effectors Into Precision Tools for Cancer Immunotherapy. *Frontiers in immunology* 10, 2683-2683 (2019).

52. J. P. van Vloten, S. T. Workenhe, S. K. Wootton, K. L. Mossman, B. W. Bridle, Critical Interactions between Immunogenic Cancer Cell Death, Oncolytic Viruses, and the Immune System Define the Rational Design of Combination Immunotherapies. *The Journal of Immunology* 200, 450-458 (2018).

53. B. Xu et al., An oncolytic herpesvirus expressing E-cadherin improves survival in mouse models of glioblastoma. *Nat Biotechnol* 10.1038/nbt.4302 (2018).

54. X. Chen et al., A combinational therapy of EGFR-CAR NK cells and oncolytic herpes simplex virus 1 for breast cancer brain metastases. *Oncotarget* 7, 27764-27777 (2016).

55. C. Comins et al., Synergistic antitumour effects of rapamycin and oncolytic reovirus. *Cancer Gene Therapy* 25, 148-160 (2018).

56. B. Tang et al., Synergistic Combination of Oncolytic Virotherapy and Immunotherapy for Glioma. *Clinical Cancer Research* 26, 2216-2230 (2020).

57. A. Kleijn et al., The Sequence of Delta24-RGD and TMZ Administration in Malignant Glioma Affects the Role of CD8(+) T Cell Anti-tumor Activity. *Mol Ther Oncolytics* 5, 11-19 (2017).
58. R. Garza-Morales et al., Temozolomide renders murine cancer cells susceptible to oncolytic adenovirus replication and oncolysis. *Cancer Biol Ther* 19, 188-197 (2018).
59. C. Y. Chen, B. Hutzen, M. F. Wedekind, T. P. Cripe, Oncolytic virus and PD-1/PD-L1 blockade combination therapy. *Oncolytic Virother* 7, 65-77 (2018).
60. Anonymous, An Oncolytic Adenovirus Targeting Transforming Growth Factor β Inhibits Protumorigenic Signals and Produces Immune Activation: A Novel Approach to Enhance Anti-PD-1 and Anti-CTLA-4 Therapy. *Human Gene Therapy* 30, 1117-1132 (2019).
61. A. K. Park et al., Effective combination immunotherapy using oncolytic viruses to deliver CAR targets to solid tumors. *Science Translational Medicine* 12, eaaz1863 (2020).
62. L. Evgin et al., Oncolytic virus-derived type I interferon restricts CAR T cell therapy. *Nature Communications* 11, 3187 (2020).
63. X. Q. Lun et al., Efficacy of systemically administered oncolytic vaccinia virotherapy for malignant gliomas is enhanced by combination therapy with rapamycin or cyclophosphamide. *Clin Cancer Res* 15, 2777-2788 (2009).
64. V. Sivanandam, C. J. LaRocca, N. G. Chen, Y. Fong, S. G. Warner, Oncolytic Viruses and Immune Checkpoint Inhibition: The Best of Both Worlds. *Mol Ther Oncolytics* 13, 93-106 (2019).

INFORMAL SEQUENCE LISTING

IL-15 of Complex (IL-15 and IL-15Rα) (SEQ ID NO: 1):
ATGAGAATTTCGAAACCACATTTGAGAAGTATTTCCATCCAGTGCTACTTGTGTTTACTT
CTAAACAGTCATTTTCTAACTGAAGCTGGCATTCATGTCTTCATTTTGGGCTGTTTCAGT
GCAGGGCTTCCTAAAACAGAAGCCAACTGGGTGAATGTAATAAGTGATTTGAAAAAAA
TTGAAGATCTTATTCAATCTATGCATATTGATGCTACTTTATATACGGAAAGTGATGTTC
ACCCCAGTTGCAAAGTAACAGCAATGAAGTGCTTTCTCTTGGAGTTACAAGTTATTTCA
CTTGAGTCCGGAGATGCAAGTATTCATGATACAGTAGAAAATCTGATCATCCTAGCAAA
CAACAGTTTGTCTTCTAATGGGAATGTAACAGAATCTGGATGCAAAGAATGTGAGGAA
CTGGAGGAAAAAAATATTAAAGAATTTTTGCAGAGTTTTGTACATATTGTCCAAATGTT
CATCAACACTTCT IL-15Rα of Complex (IL-15 and IL-15Rα) (SEQ ID NO: 2):
atgaccgaggcttggagatgtctcgtcctgtccaatgtcaccgctagacctgagaatctgcacttgggagcttacagacccggttctcaggcttca
cttgagaccccaagaaagaaaaaaacccaccagccaaagaggaggatggcagcctggaagaacctaaggaagcgaggctcagagtgggga
caccggaccgagtgcacactggaggtcccagagcacgacgagcgcggaggaccgggaggctcccgggcttgcgtgggcatcacgtgccct
ccccccatgtccgtggaacacgcagacatctgggtcaagagctacagcttgtactccagggagcggtacatttgtaactctggtttcaagcgtaaa
gccggcacgtccagcctgacggagtgcgtgttgaacaaggccacgaatgtcgcccactggacaacccccagtctcaaatgcattaagcccgca
gcttcatctcccagctcaaacaacacagcggccacaacagcagctattgtcccgggctcccagctgatgccttcaaaatcaccttccacaggaac
cacagagataagcagtcatgagtcctcccacggcacccccctctcagacaacagccaagaactgggaactcacagcatccgcctcccaccagc
cgccaggtgtgtatccacagggccacagcgacaccactgtggctatctccacgtccactgtcctgctgtgtgggctgagcgctgtgtctctcctgg
catgctacctcaagtcaagggcctctgtctgctcctgccatccccgcagtgctggacatacatgctcagtgggaagcgtctgttga Soluble IL-15/IL-15Rα in OV-IL15C (SEQ ID NO: 3):
GCTAGCGCCACCATGTACAGGATGCAACTCCTGTCTTGCATTGCACTAAGTCTTGCACT
TGTCACAAACAGTATGAGAATTTCGAAACCACATTTGAGAAGTATTTCCATCCAGTGCT
ACTTGTGTTTACTTCTAAACAGTCATTTTCTAACTGAAGCTGGCATTCATGTCTTCATTT
TGGGCTGTTTCAGTGCAGGGCTTCCTAAAACAGAAGCCAACTGGGTGAATGTAATAAG
TGATTTGAAAAAAATTGAAGATCTTATTCAATCTATGCATATTGATGCTACTTTATATAC
GGAAAGTGATGTTCACCCCAGTTGCAAAGTAACAGCAATGAAGTGCTTTCTCTTGGAGT
TACAAGTTATTTCACTTGAGTCCGGAGATGCAAGTATTCATGATACAGTAGAAAATCTG
ATCATCCTAGCAAACAACAGTTTGTCTTCTAATGGGAATGTAACAGAATCTGGATGCAA
AGAATGTGAGGAACTGGAGGAAAAAAATATTAAAGAATTTTTGCAGAGTTTTGTACAT
ATTGTCCAAATGTTCATCAACACTTCTAGCGGCGGTGGCAGCGGCGGTGGCGGTAGCG
GCGGTGGCGGTAGCGGCGGTGGCGGTAGCGGCGGTGGCAGCCTGCAGATCACCTGCCC
CCCCCCCATGAGCGTGGAGCACGCCGACATCTGGGTGAAGAGCTACAGCCTGTACAGC
AGAGAGAGATACATCTGCAACAGCGGCTTCAAGAGAAAGGCCGGCACCAGCAGCCTG
ACCGAGTGCGTGCTGAACAAGGCCACCAACGTGGCCCACTGGACCACCCCCAGCCTGA
AGTGCATCAGATACCCATACGATGTTCCAGATTACGCTTGAGAATTC IL-2 signal peptide (SEQ ID NO: 4):
ATGTACAGGATGCAACTCCTGTCTTGCATTGCACTAAGTCTTGCACTTGTCACAAACAG
T HAtag (SEQ ID NO: 5):
TACCCATACGATGTTCCAGATTACGCT HSV pIE4/5 promoter (SEQ ID NO: 6):
ttcgcacttcgtcccaatatatatatattattagggcgaagtgcgagcactggcgccgtgcccgactccgcgccggccccgggggcgggcccg
ggcggcggggggcgggtctctccggcgcacataaaggcccggcgcgaccga anti-EGFR variable light chain (SEQ ID NO: 7):
gacattctaatgacccaatctccactctccctgcctgtcagtcttggagatcaagcctccatctcttgcagatctagtcagaacattgtacataat
aatggaatcacctatttagaatggtacctgcaaaggccaggccagtctccaaagctcctgatctacaaagtttccgaccgattttctggggtccca
gacaggttcagtggcagtggatcagggacagatttcacactcaagatcagcagagtagaggctgaggatctgggaatttattactgctttcaaggt
tcacatattcctcccacgttcggagggggggaccaagctggaaatcaaacgtgcggcc -continued

INFORMAL SEQUENCE LISTING anti-EGFR variable heavy chain (SEQ ID NO: 8):
caggtccagctgcagcagtctgggtctgagatggcgaggcctggagcttcagtgaagctgccctgcaaggcttctggcgacacattcaccagtt
actggatgcactgggtgaagcagaggcatggacatggccctgagtggatcggaaatatttatccaggtagtggtggtactaactacgctgagaa
gttcaagaacaaggtcactctgactgtagacaggtcctcccgcacagtctacatgcacctcagcaggctgacatctgaggactctgcggtctatta
ttgtacaagatcgggggtccctacttctttgactactggggccaaggcaccactctcacagtctcctcc G4S linker (SEQ ID NO: 9):
ggcgggggcggtagcggcggtggcgggtcgggcggtggcggatcc

What is claimed is:

1. A recombinant oncolytic herpes simplex virus (HSV) comprising: an expression cassette comprising a nucleic acid encoding a human IL-15 domain and a nucleic acid encoding a human IL-15Rα sushi domain, wherein the nucleic acid encoding the human IL-15Rα sushi domain comprises SEQ ID NO:2.

2. The recombinant oncolytic virus of claim 1, wherein the expression cassette further comprises a nucleic acid encoding an IL-2 signal peptide sequence.

3. The recombinant oncolytic virus of claim 1, wherein the recombinant oncolytic virus does not comprise a nucleic acid encoding a γ34.5 gene or does not comprise a nucleic acid encoding a functional ICP6 gene.

4. The recombinant oncolytic virus of claim 1, wherein the nucleic acid encoding the IL-15 domain and the nucleic acid encoding the IL-15Rα sushi domain are under the control of a viral or tumor specific gene promoter.

5. The recombinant oncolytic virus of claim 4, wherein the nucleic acid encoding the IL-15 domain and the nucleic acid encoding the IL-15Rα sushi domain are under the control of herpes simplex virus (HSV) immediate early (IE) promoter.

6. A pharmaceutical composition comprising: the recombinant oncolytic virus of claim 1, and a pharmaceutically acceptable carrier.

7. A combination therapy comprising the pharmaceutical composition of claim 6 and a checkpoint inhibitor.

8. A method of treating a patient having cancer comprising administering to the patient an effective amount of the recombinant oncolytic virus of claim 1.

9. The method of claim 8, wherein the cancer is selected from glioblastoma, ovarian cancer, pancreatic cancer, leukemia, myeloma, and lymphoma.

10. A method of treating a subject with an overactive immune system or an autoimmune disease, comprising administering to the subject an effective amount of the recombinant oncolytic virus of claim 1.

11. A method for increasing cytotoxicity of natural killer (NK) cells and/or CD8 T cells in a subject, comprising administering an effective amount of the recombinant oncolytic virus of claim 1.

12. A method for increasing survival and/or proliferation of immune cells in a subject, comprising administering an effective amount the recombinant oncolytic virus of claim 1.

13. The method of claim 12, wherein the immune cells are natural killer (NK) cells or CD8 T cells.

14. A pharmaceutical composition comprising a first pharmaceutical dosage unit of the recombinant oncolytic virus of claim 1, a second pharmaceutical dosage unit comprising Epidermal Growth Factor Receptor-Chimeric Antigen Receptor Natural Killer (EGFR-CAR NK) cells, and a pharmaceutically acceptable carrier.

15. A combination therapy comprising the pharmaceutical composition of claim 14 and a checkpoint inhibitor.

16. The method of claim 8, further comprising administering to the patient an effective amount of an Epidermal Growth Factor Receptor-Chimeric Antigen Receptor Natural Killer (EGFR-CAR NK) cell.

17. The method of claim 8, further comprising administering to the patient a checkpoint inhibitor.

18. The recombinant oncolytic virus of claim 1, wherein the nucleic acid encoding the human IL15 domain comprises SEQ ID NO:1.

19. The pharmaceutical composition of claim 14, wherein the EGFR-CAR NK cells comprise an anti-EGFR antibody, wherein the anti-EGFR antibody comprises a variable light chain domain encoded by SEQ ID NO:7 and a variable heavy chain domain encoded by SEQ ID NO:8.

20. A recombinant oncolytic herpes simplex virus (HSV) comprising: an expression cassette encoding a human IL15 domain and a human IL-15Rα sushi domain, wherein the expression cassette comprises SEQ ID NO:3.

* * * * *